United States Patent
Heller et al.

(10) Patent No.: US 6,329,161 B1
(45) Date of Patent: Dec. 11, 2001

(54) SUBCUTANEOUS GLUCOSE ELECTRODE

(75) Inventors: Adam Heller; Michael V. Pishko, both of Austin, TX (US)

(73) Assignee: TheraSense, Inc., Alameda, CA (US)

( * ) Notice: Subject to any disclaimer, the term of this patent is extended or adjusted under 35 U.S.C. 154(b) by 0 days.

(21) Appl. No.: 09/668,221

(22) Filed: Sep. 22, 2000

Related U.S. Application Data

(63) Continuation of application No. 09/477,053, filed on Jan. 3, 2000, which is a continuation of application No. 09/356,102, filed on Jul. 16, 1999, now Pat. No. 6,121,009, which is a continuation of application No. 08/767,110, filed on Dec. 4, 1996, which is a continuation-in-part of application No. 08/299,526, filed on Sep. 1, 1994, now Pat. No. 5,593,852, and a continuation-in-part of application No. 08/161,682, filed on Dec. 2, 1993, now Pat. No. 5,356,786.

(51) Int. Cl.⁷ .............................. C12Q 1/54; C12Q 1/28; C12Q 1/32
(52) U.S. Cl. ............................ 435/14; 435/28; 435/26; 435/24; 435/288; 435/291; 204/403; 204/157.1; 204/153.1
(58) Field of Search ................................ 435/14, 28, 26, 435/24, 288, 291; 204/403, 157.15, 153.1

(56) References Cited

U.S. PATENT DOCUMENTS

| | | | |
|---|---|---|---|
| Re. 32,947 | 6/1989 | Dorner et al. | 435/14 |
| 3,260,656 | 7/1966 | Ross, Jr. | 435/14 |
| 3,653,841 | 4/1972 | Klein | 435/14 |
| 3,719,564 | 3/1973 | Lilly, Jr. et al. | 435/14 |
| 3,776,832 | 12/1973 | Oswin et al. | 435/14 |
| 3,837,339 | 9/1974 | Aisenberg et al. | 435/14 |
| 3,926,760 | 12/1975 | Allen et al. | 435/14 |
| 3,972,320 | 8/1976 | Kalman | 435/14 |
| 3,979,274 | 9/1976 | Newman | 435/14 |
| 4,008,717 | 2/1977 | Kowarski | 435/14 |
| 4,016,866 | 4/1977 | Lawton | 435/14 |

(List continued on next page.)

FOREIGN PATENT DOCUMENTS

| | | |
|---|---|---|
| 29 03 216 | 8/1979 | (DE) . |
| 227 029 A3 | 9/1985 | (DE) . |
| 3934299 | 10/1990 | (DE) . |
| 44 01 400 A1 | 7/1995 | (DE) . |
| 0 010 375 A1 | 4/1980 | (EP) . |

(List continued on next page.)

OTHER PUBLICATIONS

Abruna, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1): 1–5 (Jan. 14, 1981)

Abstract from Korf, J. et al., "Monitoring of Glucose and Lactate Using Microdialysis: Applications in Neonates and Rat Brain", *Developmental Neuroscience*, vol. 15, No. 3–5, pp. 240–46 (1993).

(List continued on next page.)

*Primary Examiner*—Louise N. Leary
(74) *Attorney, Agent, or Firm*—Merchant & Gould P.C.

(57) ABSTRACT

A small diameter flexible electrode designed for subcutaneous in vivo amperometric monitoring of glucoses is described. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

48 Claims, 10 Drawing Sheets

U.S. PATENT DOCUMENTS

| | | | |
|---|---|---|---|
| 4,055,175 | 10/1977 | Clemens et al. | 435/14 |
| 4,059,406 | 11/1977 | Fleet | 435/14 |
| 4,076,596 | 2/1978 | Connery et al. | 435/14 |
| 4,098,574 | 7/1978 | Dappen | 435/14 |
| 4,100,048 | 7/1978 | Pompei et al. | 435/14 |
| 4,151,845 | 5/1979 | Clemens | 435/14 |
| 4,168,205 | 9/1979 | Danninger et al. | 435/14 |
| 4,172,770 | 10/1979 | Semersky et al. | 435/14 |
| 4,178,916 | 12/1979 | McNamara | 435/14 |
| 4,206,755 | 6/1980 | Klein | 435/14 |
| 4,224,125 | 9/1980 | Nakamura et al. | 435/14 |
| 4,240,438 | 12/1980 | Updike et al. | 435/14 |
| 4,247,297 | 1/1981 | Berti et al. | 435/14 |
| 4,340,458 | 7/1982 | Lerner et al. | 435/14 |
| 4,352,960 | 10/1982 | Dorner et al. | 435/14 |
| 4,356,074 | 10/1982 | Johnson | 435/14 |
| 4,365,637 | 12/1982 | Johnson | 435/14 |
| 4,366,033 | 12/1982 | Richter et al. | 435/14 |
| 4,375,399 | 3/1983 | Havas et al. | 435/14 |
| 4,384,586 | 5/1983 | Christiansen | 435/14 |
| 4,390,621 | 6/1983 | Bauer | 435/14 |
| 4,401,122 | 8/1983 | Clark, Jr. | 435/14 |
| 4,404,066 | 9/1983 | Johnson | 435/14 |
| 4,418,148 | 11/1983 | Oberhardt | 435/14 |
| 4,427,770 | 1/1984 | Chen et al. | 435/14 |
| 4,431,004 | 2/1984 | Bessman et al. | 435/14 |
| 4,436,094 | 3/1984 | Cerami | 435/14 |
| 4,440,175 | 4/1984 | Wilkins | 435/14 |
| 4,450,842 | 5/1984 | Zick et al. | 435/14 |
| 4,458,686 | 7/1984 | Clark, Jr. | 435/14 |
| 4,461,691 | 7/1984 | Frank | 435/14 |
| 4,469,110 | 9/1984 | Stama | 435/14 |
| 4,477,314 | 10/1984 | Richter et al. | 435/14 |
| 4,484,987 | 11/1984 | Gough | 435/14 |
| 4,522,690 | 6/1985 | Venkatasetty | 435/14 |
| 4,524,114 | 6/1985 | Samuels et al. | 435/14 |
| 4,526,661 | 7/1985 | Steckhan et al. | 435/14 |
| 4,534,356 | 8/1985 | Papadakis | 435/14 |
| 4,538,616 | 9/1985 | Rogoff | 435/14 |
| 4,543,955 | 10/1985 | Schroeppel | 435/14 |
| 4,545,382 | 10/1985 | Higgins et al. | 435/14 |
| 4,552,840 | 11/1985 | Riffer | 435/14 |
| 4,560,534 | 12/1985 | Kung et al. | 435/14 |
| 4,571,292 | 2/1986 | Liu et al. | 435/14 |
| 4,573,994 | 3/1986 | Fischell et al. | 435/14 |
| 4,581,336 | 4/1986 | Malloy et al. | 435/14 |
| 4,595,011 | 6/1986 | Phillips | 435/14 |
| 4,619,754 | 10/1986 | Niki et al. | 435/14 |
| 4,627,445 | 12/1986 | Garcia et al. | 435/14 |
| 4,627,908 | 12/1986 | Miller | 435/14 |
| 4,633,878 | 1/1987 | Bombardieri | 435/14 |
| 4,637,403 | 1/1987 | Garcia et al. | 435/14 |
| 4,650,547 | 3/1987 | Gough | 435/14 |
| 4,654,197 | 3/1987 | Lilja et al. | 435/14 |
| 4,655,880 | 4/1987 | Liu | 435/14 |
| 4,655,885 | 4/1987 | Hill et al. | 435/14 |
| 4,671,288 | 6/1987 | Gough | 435/14 |
| 4,679,562 | 7/1987 | Luksha | 435/14 |
| 4,680,268 | 7/1987 | Clark, Jr. | 435/14 |
| 4,682,602 | 7/1987 | Prohaska | 435/14 |
| 4,684,537 | 8/1987 | Graetzel et al. | 435/14 |
| 4,685,463 | 8/1987 | Williams | 435/14 |
| 4,703,756 | 11/1987 | Gough et al. | 435/14 |
| 4,711,245 | 12/1987 | Higgins et al. | 435/14 |
| 4,717,673 | 1/1988 | Wrighton et al. | 435/14 |
| 4,721,601 | 1/1988 | Wrighton et al. | 435/14 |
| 4,721,677 | 1/1988 | Clark, Jr. | 435/14 |
| 4,726,378 | 2/1988 | Kaplan | 435/14 |
| 4,726,716 | 2/1988 | McGuire | 435/14 |
| 4,757,022 | 7/1988 | Shults et al. | 435/14 |
| 4,758,323 | 7/1988 | Davis et al. | 435/14 |
| 4,759,371 | 7/1988 | Pranetzki | 435/14 |
| 4,759,828 | 7/1988 | Young et al. | 435/14 |
| 4,764,416 | 8/1988 | Ueyama et al. | 435/14 |
| 4,776,944 | 10/1988 | Janata et al. | 435/14 |
| 4,777,953 | 10/1988 | Ash et al. | 435/14 |
| 4,781,798 | 11/1988 | Gough | 435/14 |
| 4,784,736 | 11/1988 | Lonsdale et al. | 435/14 |
| 4,795,707 | 1/1989 | Niiyama et al. | 435/14 |
| 4,796,634 | 1/1989 | Huntsman et al. | 435/14 |
| 4,805,624 | 2/1989 | Yao et al. | 435/14 |
| 4,813,424 | 3/1989 | Wilkins | 435/14 |
| 4,815,469 | 3/1989 | Cohen et al. | 435/14 |
| 4,820,399 | 4/1989 | Senda et al. | 435/14 |
| 4,822,337 | 4/1989 | Newhouse et al. | 435/14 |
| 4,830,959 | 5/1989 | McNeil et al. | 435/14 |
| 4,832,797 | 5/1989 | Vadgama et al. | 435/14 |
| 4,840,893 | 6/1989 | Hill et al. | 435/14 |
| 4,848,351 | 7/1989 | Finch | 435/14 |
| 4,854,322 | 8/1989 | Ash et al. | 435/14 |
| 4,871,351 | 10/1989 | Feingold | 435/14 |
| 4,871,440 | 10/1989 | Nagata et al | 435/14 |
| 4,874,500 | 10/1989 | Madou et al. | 435/14 |
| 4,890,620 | 1/1990 | Gough | 435/14 |
| 4,894,137 | 1/1990 | Takizawa et al. | 435/14 |
| 4,897,162 | 1/1990 | Lewandowski et al | 435/14 |
| 4,897,173 | 1/1990 | Nankai et al. | 435/14 |
| 4,909,908 | 3/1990 | Ross et al. | 435/14 |
| 4,911,794 | 3/1990 | Paroc et al. | 435/14 |
| 4,917,800 | 4/1990 | Lonsdale et al. | 435/28 |
| 4,919,141 | 4/1990 | Zier et al. | 435/28 |
| 4,919,767 | 4/1990 | Vadgama et al. | 435/28 |
| 4,923,586 | 5/1990 | Katayama et al. | 435/28 |
| 4,927,516 | 5/1990 | Yamaguchi et al. | 435/28 |
| 4,934,369 | 6/1990 | Maxwell | 435/28 |
| 4,935,105 | 6/1990 | Churchouse | 435/28 |
| 4,935,345 | 6/1990 | Guilbeau et al. | 435/28 |
| 4,938,860 | 7/1990 | Wogoman | 435/14 |
| 4,944,299 | 7/1990 | Silvian | 435/14 |
| 4,950,378 | 8/1990 | Nagata | 435/14 |
| 4,953,552 | 9/1990 | DeMarzo | 435/14 |
| 4,954,129 | 9/1990 | Giuliani et al. | 435/14 |
| 4,969,468 | 11/1990 | Byers et al. | 435/14 |
| 4,970,145 | 11/1990 | Bennetto et al. | 435/14 |
| 4,974,929 | 12/1990 | Curry | 435/14 |
| 4,986,271 | 1/1991 | Wilkins | 435/14 |
| 4,994,167 | 2/1991 | Shuls et al. | 435/14 |
| 5,001,054 | 3/1991 | Wagner | 435/14 |
| 5,002,054 | 3/1991 | Ash et al. | 435/14 |
| 5,058,592 | 10/1991 | Whisler | 435/14 |
| 5,070,535 | 12/1991 | Hochmair et al. | 435/14 |
| 5,082,550 | 1/1992 | Rishpon et al. | 435/14 |
| 5,082,786 | 1/1992 | Nakamoto | 435/14 |
| 5,089,112 | 2/1992 | Skotheim et al. | 435/14 |
| 5,095,904 | 3/1992 | Seligman et al. | 435/14 |
| 5,101,814 | 4/1992 | Palti | 435/14 |
| 5,106,365 | 4/1992 | Hernandez | 435/14 |
| 5,108,564 | 4/1992 | Szuminsky et al. | 435/14 |
| 5,109,850 | 5/1992 | Blanco et al. | 435/14 |
| 5,120,420 | 6/1992 | Nankai et al. | 435/14 |
| 5,126,034 | 6/1992 | Carter et al. | 435/14 |
| 5,133,856 | 7/1992 | Yamaguchi et al. | 435/14 |
| 5,135,003 | 8/1992 | Souma | 435/14 |
| 5,141,868 | 8/1992 | Shanks et al. | 435/14 |
| 5,161,532 | 11/1992 | Joseph | 435/14 |
| 5,165,407 | 11/1992 | Wilson et al. | 435/14 |
| 5,174,291 | 12/1992 | Schoonen et al. | 435/14 |
| 5,190,041 | 3/1993 | Palti | 435/14 |
| 5,192,416 | 3/1993 | Wang et al. | 435/14 |
| 5,198,367 | 3/1993 | Aizawa et al. | 435/14 |
| 5,202,261 | 4/1993 | Musho et al. | 435/14 |

| | | | | | | |
|---|---|---|---|---|---|---|
| 5,205,920 | 4/1993 | Oyama et al. | 435/14 | 0 096 288 A1 | 12/1983 | (EP) . |
| 5,208,154 | 5/1993 | Weaver et al. | 435/14 | 0 125 139 A2 | 11/1984 | (EP) . |
| 5,209,229 | 5/1993 | Gilli | 435/14 | 0 127 958 A2 | 12/1984 | (EP) . |
| 5,217,595 | 6/1993 | Smith et al. | 435/14 | 0 136 362 A1 | 4/1985 | (EP) . |
| 5,229,282 | 7/1993 | Yoshioka et al. | 435/14 | 0 170 375 A2 | 2/1986 | (EP) . |
| 5,250,439 | 10/1993 | Musho et al. | 435/14 | 0 177 743 A2 | 4/1986 | (EP) . |
| 5,262,035 | 11/1993 | Gregg et al. | 435/14 | 0 080 304 B1 | 5/1986 | (EP) . |
| 5,262,305 | 11/1993 | Heller et al. | 435/14 | 0 184 909 A2 | 6/1986 | (EP) . |
| 5,264,103 | 11/1993 | Yoshioka et al. | 435/14 | 0 206 218 A2 | 12/1986 | (EP) . |
| 5,264,104 | 11/1993 | Gregg et al. | 435/14 | 0 230 472 A1 | 8/1987 | (EP) . |
| 5,264,106 | 11/1993 | McAleer et al. | 435/14 | 0 241 309 A3 | 10/1987 | (EP) . |
| 5,271,815 | 12/1993 | Wong | 435/14 | 0 245 073 A2 | 11/1987 | (EP) . |
| 5,279,294 | 1/1994 | Anderson et al. | 435/14 | 0 278 647 A2 | 8/1988 | (EP) . |
| 5,286,362 | 2/1994 | Hoenes et al. | 435/14 | 0 359 831 A2 | 3/1990 | (EP) . |
| 5,286,364 | 2/1994 | Yacynych et al. | 435/14 | 0 368 209 A1 | 5/1990 | (EP) . |
| 5,288,636 | 2/1994 | Pollmann et al. | 435/14 | 0 390 390 A1 | 10/1990 | (EP) . |
| 5,293,546 | 3/1994 | Tadros et al. | 435/14 | 0 400 918 A1 | 12/1990 | (EP) . |
| 5,320,098 | 6/1994 | Davidson | 435/14 | 0 453 283 A1 | 10/1991 | (EP) . |
| 5,320,725 | 6/1994 | Gregg et al. | 435/14 | 0 470 290 A1 | 2/1992 | (EP) . |
| 5,322,063 | 6/1994 | Allen et al. | 435/14 | 0 127 958 B2 | 3/1992 | (EP) . |
| 5,337,747 | 8/1994 | Neftel | 435/14 | 0 255 291 B1 | 6/1992 | (EP) . |
| 5,352,348 | 10/1994 | Young et al. | 435/14 | 1394171 | 5/1975 | (GB) . |
| 5,356,786 * | 10/1994 | Heller et al. | 435/14 | 1599241 A | 9/1981 | (GB) . |
| 5,368,028 | 11/1994 | Palti | 435/14 | 2 073 891 A | 10/1981 | (GB) . |
| 5,372,133 | 12/1994 | Esch | 435/14 | 2 154 003 B | 2/1988 | (GB) . |
| 5,376,251 | 12/1994 | Kaneko et al. | 435/14 | 2 204 408 A | 11/1988 | (GB) . |
| 5,378,628 | 1/1995 | Gratzel et al. | 435/14 | 2 254 436 A | 10/1992 | (GB) . |
| 5,387,327 | 2/1995 | Khan | 435/14 | 54-41191 | 4/1979 | (JP) . |
| 5,390,671 | 2/1995 | Lord et al. | 435/14 | 55-10581 | 1/1980 | (JP) . |
| 5,391,250 | 2/1995 | Cheney, II et al. | 435/14 | 55-10583 | 1/1980 | (JP) . |
| 5,395,504 | 3/1995 | Saurer et al. | 435/14 | 55-10584 | 1/1980 | (JP) . |
| 5,411,647 | 5/1995 | Johnson et al. . | | 55-12406 | 1/1980 | (JP) . |
| 5,437,999 | 8/1995 | Diebold et al. . | | 56-163447 | 12/1981 | (JP) . |
| 5,462,645 | 10/1995 | Albery et al. . | | 60-173457 | 9/1985 | (JP) . |
| 5,469,846 | 11/1995 | Khan . | | 60-173458 | 9/1985 | (JP) . |
| 5,494,562 | 2/1996 | Maley et al. . | | 60-173459 | 9/1985 | (JP) . |
| 5,496,453 | 3/1996 | Uenoyama et al. . | | 61-90050 | 5/1986 | (JP) . |
| 5,497,772 | 3/1996 | Schulman et al. . | | 62-85855 | 4/1987 | (JP) . |
| 5,531,878 | 7/1996 | Vadgama et al. . | | 62-114747 | 5/1987 | (JP) . |
| 5,545,191 | 8/1996 | Mann et al. . | | 63-58149 | 3/1988 | (JP) . |
| 5,560,357 | 10/1996 | Faupel et al. | 435/14 | 57-70448 | 4/1988 | (JP) . |
| 5,565,085 | 10/1996 | Ikeda et al. | 435/14 | 63-128252 | 5/1988 | (JP) . |
| 5,567,302 | 10/1996 | Song et al. | 435/14 | 63-139246 | 6/1988 | (JP) . |
| 5,568,806 | 10/1996 | Cheney, II et al. | 435/14 | 63-294799 | 12/1988 | (JP) . |
| 5,569,186 | 10/1996 | Lord et al. | 435/14 | 63-317757 | 12/1988 | (JP) . |
| 5,582,184 | 12/1996 | Erickson et al. | 435/14 | 63-317758 | 12/1988 | (JP) . |
| 5,582,697 | 12/1996 | Ikeda et al. | 435/14 | 1-114746 | 5/1989 | (JP) . |
| 5,582,698 | 12/1996 | Flaherty et al. | 435/14 | 1-114747 | 5/1989 | (JP) . |
| 5,586,553 | 12/1996 | Halili et al. | 435/14 | 1-124060 | 5/1989 | (JP) . |
| 5,589,326 | 12/1996 | Deng et al. | 435/14 | 1-134244 | 5/1989 | (JP) . |
| 5,593,852 * | 1/1997 | Heller et al. | 435/14 | 1-156658 | 6/1989 | (JP) . |
| 5,596,150 | 1/1997 | Arndt et al. | 435/14 | 2-62958 | 3/1990 | (JP) . |
| 5,617,851 | 4/1997 | Lipkover | 435/14 | 2-120655 | 5/1990 | (JP) . |
| 5,628,890 | 5/1997 | Carter et al. | 435/14 | 2-287145 | 11/1990 | (JP) . |
| 5,651,869 | 7/1997 | Yoshioka et al. | 435/14 | 2-310457 | 12/1990 | (JP) . |
| 5,660,163 | 8/1997 | Schuylman et al. | 435/14 | 3-26956 | 2/1991 | (JP) . |
| 5,670,031 | 9/1997 | Hintsche et al. | 435/14 | 3-28752 | 2/1991 | (JP) . |
| 5,680,858 | 10/1997 | Hansen et al. | 435/14 | 3-202764 | 9/1991 | (JP) . |
| 5,682,233 | 10/1997 | Brinda | 435/14 | 5-72171 | 3/1993 | (JP) . |
| 5,695,623 | 12/1997 | Michel et al. | 435/14 | 5-196595 | 8/1993 | (JP) . |
| 5,708,247 | 1/1998 | McAleer et al. | 435/14 | 6-190050 | 7/1994 | (JP) . |
| 5,711,861 | 1/1998 | Ward et al. | 435/14 | 7-72585 | 3/1995 | (JP) . |
| 5,711,862 | 1/1998 | Sakoda et al. | 435/14 | 1281988 A1 | 1/1987 | (SU) . |
| 5,741,211 | 4/1998 | Renirie et al. | 435/14 | WO 85/05199 | 11/1985 | (WO) . |
| 5,791,344 | 8/1998 | Schulman et al. | 435/14 | WO 89/08713 | 9/1989 | (WO) . |
| 6,121,009 * | 9/2000 | Heller et al. | 435/14 | WO 90/05300 | 5/1990 | (WO) . |
| | | | | WO 90/05910 | 5/1990 | (WO) . |
| | FOREIGN PATENT DOCUMENTS | | | WO 91/01680 | 2/1991 | (WO) . |
| 0 026 995 A1 | 4/1981 | (EP) . | | WO 91/04704 | 4/1991 | (WO) . |
| 0 048 090 A2 | 3/1982 | (EP) . | | WO 91/15993 | 10/1991 | (WO) . |
| 0 078 636 A1 | 5/1983 | (EP) . | | WO 92/13271 | 8/1992 | (WO) . |

| | | |
|---|---|---|
| WO 94/20602 | 9/1994 | (WO) . |
| WO 94/27140 | 11/1994 | (WO) . |
| WO 96/30431 | 10/1996 | (WO) . |
| WO 97/02847 | 1/1997 | (WO) . |
| WO 97/19344 | 5/1997 | (WO) . |
| WO 97/42882 | 11/1997 | (WO) . |
| WO 97/42883 | 11/1997 | (WO) . |
| WO 97/42886 | 11/1997 | (WO) . |
| WO 97/42888 | 11/1997 | (WO) . |
| WO 97/43962 | 11/1997 | (WO) . |

OTHER PUBLICATIONS

Aisenberg et al., "Blood glucose, level monitoring alarm system," Great Britain Patent GB 1394171, issued May 14, 1975. (Abstract only).

Albery, W. J. et al., "Amperometric Enzyme Electrodes," *Phil. Trans. R. Soc. Lond.*B316:107–119 (1987).

Albery, W. J. et al., "Amperometric enzyme electrodes. Part II. Conducting salts as electrode materials for the oxidation of glucose oxidase," *J. Electroanal Chem. Interfacial Electrochem.*, 194(2) (1 page–Abstract only) (1985).

Alcock et al., "Continuous Analyte Monitorning in Aid Clinical Practice," *IEEE Engineering in Medicine and Biology*, pp. 319–325 (Jun./Jul. 1994).

Anderson, L. B. et al., "Thin–Layer Electrochemistry: Steady–State Methods fo Studying Rate Processes, " *J. Electroanal. Chem.*, 10:295–395 (1965).

Bartlett, P. N. et al., "Covalent Binding of Electron Relays to Glucose Oxidation," *J. Chem. Commun.*, 1603–1604 (1987).

Bartlett, P. N. et al., "Modification of glucose oxidase by tetrathiafulvalene," *J. Chem. Soc. Chem. Commun.*16(1 page –Abstract only) (1990).

Bartlett, P. N. et al., "Strategies for the Development of Amperometric Enzyme Electrodes." *Biosensors.* 3 359–379 (1987/1988).

Bindra, D. S. et al., "Design and in Vitro Studies of a Needle–Type Glucose Sensor for Subcutaneous Monitoring", *Anal. Chem.*, 63(17): 1692–1696 (Sep. 1, 1991).

Bobbioni–Harsch et al., "Lifespan of subcutaneous glucose sensors and their performances during dynamic glycaemia changes in rats," *J. Biomed. Eng.*, vol. 15, pp. 457–463 (Nov. 1993).

Brandt, J. et al., "Covalent attachment of proteins to polysaccharide carriers by means of benzoqinone," *Biochim. Biophys. Acta.*386(1) (1 page Abstract only) (1975).

Brownlee, M. et al., "A Glucose–Controlled Insulin–Delivery System: Semisynthetic Insulin Bound to Lectin", *Science*, 206(4423): 1190–1191 (Dec. 7, 1979).

Cass, A. E. G. et al., "Ferrocene–Mediated Enzyme Electrode for Amperometric Determination of Glucose", *Anal. Chem*, 56(4): 667–671 (Apr. 1984).

Cass, A. E. G. et al., "Ferricinum Ion As An Electron Acceptor for Oxido–Reductases," *J. Electroanal Chem.*, 190;117–127 (1985).

Csöregi, E. et al., "Design and Optimization of a Selective Subcutaneously Implantable Glucose Electrode Based on "Wired"Glucose Oxidase," *Anal. Chem.*67(7):1240–1241 (Apr. 1, 1995).

Castner, J. F. et al., "Mass Transport and Reaction Kinetic Parameters Determined Electrochemically for Immobilized Glucose Oxidase," *Biochemistry*, 23(10): 2203–2210 (1984).

Cerami, "Monitor for continuous in vivo measurement of glucose concentration," United States Patent 4,436,004, issued Mar. 13, 1984, 2 pages (Abstract only).

Claremeont, D.J. et al., "Biosensors for Continuous In Vivo Glucose Monitoring", *IEEE Engineering in Medicine and Biology Society 10th Annual International Conference*, New Orleans, Louisiana, 3 pages. (Nov. 4–7, 1988).

Clark, L.C., Jr. et al., "Electrode Systems for Continuous Monitoring in Cardiovascular Surgery," *Annals New York Academy of Sciences*, pp. 29–45 (1982).

Clark, L.C. et al., "Differential Anodic Enzyme Polarography for the Measurement of Glucose", *Oxygen Transport to Tissue: Instrumentation, Methods, and Physiology*, 127–132 (1973).

Clark, L.C. et al., "Long term Stability of Electroenzymatic Glucose Sensors Implanted in Mice," *Trans Am. Soc. Artif. Intern. Organs.*XXXIV:259–265 (1988).

Clarke, W. L., et al., "Evaluating Clinical Accuracy of Systems for Self–Monitoring of Blood Glucose," *Diabetes Care* 10(5): 622–628 (Sep.–Oct. 1987).

Csöregi, E. et al. "Design, Characterization and One–Point in Vivo Calibration in a Subcutaneously Implanted Glucose Electrode," *Anal. Chem.*66(19):3131–3138 (Oct. 1, 1994).

Csöregi, E. et al., "Design and Optimization of a Selective Subcutaneously Implantable Glucose Electrode Based on "Wired"Glucose Oxidase," *Anal. Chem.*67(7): 1240–1244 (Apr. 1, 1995).

Csöregi, E. et al., "On–Line Glucose Monitoring by Using Microdialysis Sampling and Amperometric Detection Based on "Wired"Glucose Oxidase in Carbon Paste," *Mikrochim. Acta*121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer From Glucose Oxidase to Metal Electrodes via Electron Relays. Bound Covalently to the Enzyme," *J. Phys. Chem.*, 91(6): 1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8): 2615–2620 (1988).

Degani, Y. et al. "Electrical Communcation between Redox Centers of Glucose Oxidase and Electrodes via Electrostatically and Covalently Bound Redox Polymers, " *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosensors," *Ann. Biol. Clin.*, 47:607–619 (1989).

Ellis, C. D., "Selectivity and Directed Charge Transfer through an Electroactive Metallopolymer Film, " *J. Am. Chem. Soc.*103(25): 7480–7483 (1981).

Engstrom, R.C., "Electrochemical Pretreatment of Glassy Carbon Electrodes," *Anal. Chem.*, 54(13): 2310–2314 (Nov. 1982).

Engstrom, R.C. et al., "Characterization of Electrochemically Pretreated Glassy Carbon Electrodes", *Anal. Chem.*, 56(2): 136–141 (Feb. 1984).

Feldman, B.J. et al., "Electron Transfer Kinetics at Redox Polymer/Solution Interaces Using Microelectrodes and Twin Electrode Thin Layer Cells", *J. Electroanal. Chem.*, 194(1):63–81 (Oct. 10, 1985).

Fischer, H. et al., "Intramolecular Electron Transfer Mediated by 4,4'–Biyridine and Related Bridging Groups" *J. Am. Chem. Soc.*, 98(18):5512–5517 (Sep. 1, 1976).

Flentge, F. et al., "An Enzyme–Reactor for Electrochemical Monitoring of Choline and Acetylcholine: Applications in High–Performance Liquid Chromatrography, Drain Tissue, Microdialysis and Cerebrospinal Fluid", *Analytical Biochemistry*, vol. 204, No. 2, pp. 305–310 (Aug. 1, 1992).

Foulds, N.C. et al., "Enzyme Entrapment in Electrically Conducting Polymers, " *J. Chem. Soc., Parady Trans. J.*, 82:1259–1264 (1986).

Foulds, N.C. et al., "Immobilization of Glucose Oxidase in Ferrocene–Modified Pyrrole Polymers," *Anal. Chem.*60(22):2473–2478 (Nov. 15, 1988).

Franetzki, "Implantable, calibrateable measuring instrument for a body substance and a calibrating method," United States Patent 4,759,371, issue Jul. 26, 1988, 2 pages (Abstract only).

Frew, J.E. et al., "Electron–Transfer Biosensors", *Phil Trans. R. Soc. Lond.*, B316:95–106 (1987).

Gilli, "Apparatus and method employing plural electrode configurations for cardioversi on atrial fibrillation in an arrhythmia control system,", United States Patent 5,209,229, issued May 11, 1993, 2 pages (Abstract only).

Gordon, L. et al., "Selective detection in flow analysis based on the combination of immobilized enzymes and chemically modified electrodes, " *Analytical Chimica Acta.*, 250:203–248 (1991).

Gregg, B. A. et al., "Cross–Linked Redox Gels Containing Oxidase for Amperometric Biosensor Applications", *Analytical Chemistry*, 62(3):258–265 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone, " *J. Phys. Chem.*, 95(15):5970–5975 (1991).

Hale, P.D. et al., "A New Class of Amperometric Biosensor Incorporating a Polymeric Electron–Transfer Mediator," *J. Am. Chem. Soc.*, 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.*, 60(19):2002–2007 (Oct. 1, 1988).

Hawkbridge, F. M. et al., "Indirect Coulomietric Titration of Biological Electron Transport Components, " *Analytical Chemistry*, 45(7):1021–1027 (Jun. 1973).

Heller, A., "Amperometric Insensors based on three–dimensionaal hydrogel–forming epoxy networks, " *Sensors and Actuators*, 13–14:180–183 (1993).

Heller, A., "Electrical Connection of Enzyme Redox Centers to Electrodes," *J. Phys. Chem.*, 96(9):3579–3587 (1992).

Ianniello, R.M. et al., "Differential Pulse Voltammetric Study of Direct Electron Transfer in Glucose Oxidase Chemically Modified Graphite Electrodes", *Anal. Chem.*, 54:(7):1098–1101 (Jun. 1981).

Ianniello, R.M. et al., "Immobilized Enzyme Chemically Modified Electrod as an Amperometric Sensor", *Anal. Chem.*, 53(13):2090–2095 (Nov. 1981).

Ikeda, T. et al., "Kinetics of Outer–Sphere Electron Transfers Between Metal Complexes in Solutions and Polymeric Films on Modified Electrodes", *J. Am. Chem. Soc.*, 103(25):7422–7425 (Dec. 16, 1981).

Ikeda, T. et al., "Glucose oxidase–immobilized benzoquinone–carbon paste electrode as a glucose sensor," *Agric. Biol. Chem.*, 49(2) (1 page –Abstract only)1985).

Johnson, J. M. et al., "Potential–Dependent Enzymatic Activity in an Enzyme Thin–Layer Cell." *Anal. Chem.*54: 1377–1383 91983):

Johnson K. W., "Reproducible Electrodeposition of Biomolecules for the Fabrication of Miniature Electroenzymatic Biosensors", *Sensors and Actuators & Chemical*, B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors*, 1:355–368 (1985).

Josowicz, M. et al., "Electrochemical Pretreatment of Thin Film Platinum Electrodes", *J. Electrochem. Soc.*, 135(1): 112–115 (January 1988).

Katakis, I. et al., "Lα–Glycerophosphate and L–Lactate Electrodes Based on the Electrochemical "Wiring"of Oxidases, " *Analytical Chemistry*, 64(9): 1008–1013 (May 1, 1992).

Katakis, I. et al. "Electrostatic Control of the Electron Transfer Enabling Binding of Recombinant Glucose Oxidase and Redox Polyelectrolytes," *J. Am. Chem. Soc.*, 116(8):3617–3618 (1994).

Kenausis, G. et al., "Wiring of glucose oxidase and lactate oxidase within a hydrogel made with poly(vinyl pyridine) complexed with $[Os(4,4-domethoxy-2,2-bipyridine)_2-Cl]^{+/2+}$, " *J. Chem. Soc., Faraday Trans.*92(20):4131–4136 (1996).

Klein, "Method and apparatus for the control and regulation of glycemia," U.S. Patent 4,206,755, issued Jun. 10, 1980, 2 pages (Abstract only).

Klein, "Control and regulation device for glycemia, " Great Britain Patent 1599241A, issued Sep. 30, 1981 (Abstract only).

Koudelka, M. et al., "In–Vivo Behaviour of Hypodermically Implanted Microfabricated Glcusoe Sensors", *Biosensors & Bioelectronics*, 6(1):31–36 (1991).

Kulys, J. et al., "Mediatorless peroxidase electrode and preparation of bioenzyme sensors," *Bioelectrochemistry and Bioelectronics*, 6(1):31–36 (1990).

Lager, W. et al., "Implantable Electrocatalytic Glucose Sensor," *Horm. Metab. Res.*, 26: 526–530 (November 1994).

Laurell, T., "A Continuous Glucose Monitoring System Based on Microdialysis", *Journal of Med Eng. & Tech.*, vol. 16, No. 5, pp. 187–193 (September/October 1992).

Lawton, "Implantable electrochemical sensor," U.S. Patent 4,016,866 issued Apr. 12, 1977 2 pages (Abstract only).

Lindner, E. et al. "Flexible (Kapton–Based) Microsensor Arrays of High Stability for Cardiovascular Applications",*J. Chem. Soc. Faraday Trans.*, 89(2):361–367 (Jan. 21, 1993).

Maidan, R. et al. "Eliminatio of Electrooxidizabel Interferon–Produced Currents in Amperometric Biosensors," *Analytical Chemistry*, 64(23):2889–2896 (Dec. 1, 1992).

Marko–Varga, G. et al., "Enzyme–Based Biosensor as a Selective Detection Unit in Column Liquid Chromatography", *Journal of Chromatography*, vol. 660, pp. 153–167 (1994).

Mastrololaro, J.J. et al., "An Electroenzymatic Glucose Sensor Fabricated on a Flexible Substrate", *Sensors and Biosensors B Chemicals*, B5:139–144 (1991).

McNeil, C. J. et al., "Thermostable Reduced Nicotinamide Aenine Dinucleotide Oxidase: Application to Amperometric Enzyme Assay," *Anal. Chem.*, 61(1).25–29 (1989),.

Miyawaki, O. et al., "Electrochemical and Glucose Oxidase Coenzyme Activity of Flaven Adenine Dinucleotide Covalently Attached to Glassy Carbon at the Adenine Amino Group," *Biochimica et Biophysica Acta*, 838:60–68 (1985).

Moati–Sirat, D. et al., "Towards continuous glucose monitoring: in vivo evaluation of a miniaturized glucose sensor impolanted for several days in a rat subcutaneous tissue,"(1 page–Abstract only) *Diabetologia*35(3): 224–30 (March 1992).

Moati–Sirat, D. et al., "Evaluating in vitro and in vivo the interference of ascorbate and acetaminophen on glucose detection by a needle–type glucose sensor," *Biosensors & Bioelectronics*, 7(5):345–352 (1992).

Nagy, G. et al., "A New Type of Enzyme Electrode: The Acorbic Acid Eliminator Electrode,", *Life Sciences*, 31(23): 2611–2616 (1982).

Nakamura, S. et al., "Effect of Periodate Oxidation on the Structure and Properties of Glucose Oxidase, " *Biochimica et Biophysica Acta.*, 445:294–308 (1976).

Narazimhan, K. et al., p–Benzoquinone activation of metal oxide electrodes for attachment of enzymes, *Enzyme Microb. Technol.*, 7(6): 1 page –Abstract only) (1985).

Ohara, T. J. et al., "Glucose Electrodes Based on Cross–Linked $[Os(bpy)_2Cl]^{+/2+}$Complexed Poly (l–vinylimadazole) Films," *Analytical Chemistry*, 65(23):3512–3516 (Dec. 1, 1993).

Ohara, T. J. et al., ""Wired"Electrodes for Amperometric Determination of Glucose or Lactate in the Presence of Intefering Substances," *Analytical Chemistry*, 66(15): 2451–2457 (Aug. 1, 1994).

Oharta, T. J., "Osmium Bipyridyl Redox Polymers Used in Enzyme Electrodes," *Platinum Metals Rev.*, 39(2):54–62 (April 1995).

Olievier, C. N. et al. "In vivo Measurement of Carbon Dioxide Tension with a Miniature Electrode," *Pfluger Arch*, 373. 269–272 (1978).

Paddock, R. et al., "Electrocatalytic reduction of hydrogen peroxide via direct electron transfer from pyrolytic graphite electrodes to irreversibgle adsorbed cytochrome c peroxidase," *J. Electroanal. Chem.*, 260:487–194 (1989).

Palleschi, G. et al. "A Study of Interferences in Glucose Measurements in Blood by Hydrogen Peroxide Based Gclucose Probes", *Anal. Biochem.*, 159:114–121 (1986).

Pankratov, i. et al. "Sol–gel derived renewable–surface biosensors," *Journal of Electroanalytical Chemistry*, 393:35–41 (1995).

Pathak, C. P. et al., "Rapid Photopolymerization of immunoprotective Gels in Contact with Cells and Tissue, " *J. Am. Chem. Soc.*, 114(21): 8311–8312 (1992).

Pickup, J. "Developing glucose sensors for in vivo use," *TIBTECH*, vol. 11, pp. 285–289 (July 1993).

Pickup, J. et al., "Potentially–implantable, amperometric glucose sensors with meidated electron transfer: improving the operating stability," *Biosensors*, 4(2), 109–19, (Abstract only) (1989).

Pickup, J. C. et al., "In vivo molecular sensing in diabetes mellitus: an implantable glucose sensor with direct electron transfer," *Diabetologia*, 32(3): 213–217 (1989).

Pishko, M. V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V., et al. "In vitro and in vivo evaluation in dogs of a miniaturized glucose sensor,"*ASAIO Transactions*, 37(3) (1 page Abstract only) (July–September 1991).

Poitout, V ET AL., "Calibration in dogs of subcutaneous miniaturized glucose sensor using a glucose meter for blood glucose determination," *Biosensors & Bioelectronics*, 7, pp. 587–592 (1992).

Poitout, V. et al., "A glucose monitoring system for on line estimation in man of blood glucose concentration using a miniaturezed glucose sensor implanted in the subcutaneous tissue and a wearable control unit." (1 page –Abstract only) *Diabetologia*36(7):658–63 (Hykt 1993).

Pollak, A., et al., "Enzyme Immobilization by Condensation Copolymerization into Cross–Linked Polyacrylamide Gels," *J. Am. Chem. Soc.*102(20):6324–6330 (1980).

Reach, G. et al., "Can Continuous Glucose Monitoring Be Used for the Treamtnt of Diabetes" *Analytical Chemistry*, 64(6).381–386 (Mar. 15, 1992).

Rebrin, K. et al., "Automated Feedback Control of Subcutaneous Glucose Concentration in Diabetic Dogs", *Diabetologia*, 32(8):573–576 (August 1989).

Sakakida, M. et al., "Ferrocene–mediate needle–type glucose sensor covered with newly designed biocompatible membrane." *Sensors and Actuators B*, 13–14:319–322 (1993).

Samuels, G. J. et al., "An Electrode–Supported Oxidation Catalyst Based on Ruthenium (IV) pH "Encapsulation"in a Polymer Film." *J. Am. Chem. Soc.*, 103(2):307–312 (1981).

Sasso, S.V. et al., "Electropolymerized 1,2–Diaminobenzene as a Means to Prevent Interferences and Fouling and Stabilize Immobilized Enzyme in Electrochemical Biosensors", *Anal. Chem.*, 62(1): 1111–1117 (Jun. 1, 1990).

Scheller, F. et al., "Enzyme electrodes and their application," *Phil. Trans. R. Soc. Lond.*, B 316. 85–94 (1987).

Schmehl, R.H. et al., "The Effect of Redox Site Concentration on the Rate of Mediated Oxidation of Solution Substrates by a Redox Copolymer Film",*J. Electroanal. Chem.*, 152:97–109 (Aug. 25, 1983).

Schmidt, F.J. et al., "Calibration of a Wearable Glucose Sensor", *The International Journal of Artificial Organs*, vol. 15 No. 1, pp. 55–61 (1992).

Shichiri, M. et al., "Glycaemic Control in Pancreatotomized Dogs with a Wearable Artificial Endocrine Pancreas", *Diabetologia*, 24(3): 179–184 (March 1983).

Sitampalam, G. et al., "Surface–Modified Electrochemical Detector for Liquid Chromatography", *Anal. Chem.*55(9):1608–1610 (August 1983).

Soegijoko, S. et al., *Horm. Metab. Res., Suppl. Ser.*, 12, pp. 165–169 (1982) (Abstract).

Sprules, S. D. et al., "Evaluation of a New Disposable Screen–Printed Sensor Strip for the Measurement of NADH and Its Modification to Produce a Lactate Biosensor Employing Microliter Volumes, " *Electroanalysis*, 8(6):539–543 (1996).

Sternberg, F. et al. "Calibration Problems of Subcutaneous Glucosensors when Applied "In–Situ"in Man." *Horm. metabl. Res.*26.524–525 (1994).

Sternberg, R. et al., "Covalent Enzyme Coupling on Cellulose Acetate Membranesw for Glucose Sensor Development," *Analytical Chemistry*, 60(24):2781–2786 (Dec. 15, 1988).

Sternberg, R. et al., "Study and Development of Multilayer Needle–type Enzyme–based Glucose Microsensors," *Biosensors*, 4:27–40 (1988).

Suekane, M., "Immobiization of glucose isomeerase," *Zeitschrift für Allgemeine Mikrobiologie*, 22(8):565–576 (1982).

Tajima, S. et al., "Simultaneous Determination of Glucose and 1,5–Anydroglucitol", *Chemcal Abstracts*, 111(25):394 111:228556g (Dec. 18, 1989).

Tarasevbich, M.R. "Bioelectrocatalysis", *Comprehensive Treatise of Electrofhemistry*, 10 (Ch. 4) 231–295 (1985).

Tatsuma, T. et al., "Enzyme Monolayer–and Bilayer–Modified Tin Oxide Electroes for the Determination of Hydrogen Peroxide and Glucose, " Anal. Chem. 61(21);2352–2355 (Nov. 1, 1989).

Taylor, C. et al., "Wiring of glcuose oxidase within a hydrogel made withy polyvinyl imidazole complexed with [(Os 4,4'–dimethoxy–,2–bipyridine)C1]+/2 +, " Journal of Electroanalytical Chemistry, 396:511–515 (1995).

Trojanowicz, M. et al., "Enzyme Entrapped Polypyrrole Modified Electrode for Flow–Injection Determination of Glucose," *Biosensors & Bielectronics*, 5:149–156 (1990).

Turner, A.P.F. et al., "Diabetes Mellitus; Biosensors for Research and Management", *Biosensors*, 1:85–115 (1985).

Turner, R. F. B. et al., "A Biocompatible Enzyme Electrode for Continuous in vio Glucose Monitoring in Whole Blood," *Sensors and Actuators*, B1 (1–6): 56–564 (January 1990).

Tuzhi, P. et al., "Constant Potential Pretreatment of Carbon Fiber Electrodes for In Vivo Electrochemistry", *Analytical Letters*, 24(6): 935–945 (1991).

Umaha, M., "Protein–Modified Electrochemically Active Biomaterial Surface", *U.S. Army Research Office Report*, (12 pages) (December 1988).

Urban, G. et al., "Miniaturized Thin–Film Biosensors Using Covalently Immobilized Glucose Oxidase," *Biosensors & Bioelectronics*, 6(7): 555–562 (1991).

Vadgama et al., "Sensor devices, " U.S. Patent 5,531,878, issued Jul. 2, 1996, 2 pages (Abstract only).

Velho et al., "Strategies for calibrating a subcutaneous glucose sensor," *Biomedica Biochimica Acta*.vol. 48, Issue 11–12, pp. 957–964 (1989).

Velho, G. et al., "In Vitro and In Vivo Stability of Electrode Potentials in Needle–Type Glucose Sensors", *Diabetes*, 38(2) 164–171 (February 1989).

Vreeke, M. et al., "Hydrogen Peroxide and β–Nicotinamide Adenine Dincucleotide Sensing Amperometric Electrodes Based on Electrical Connection of Horseradish Peroxidase Redox Centers to Electrodes through a Three–Dimensional Electron Relaying Polymer Network", *Analytical Chemistry*, 64(24):3084–3090 (Dec. 15, 1992).

Vrecke, M. S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers*, 7 pages (July 26, 1993).

Wang, D. L. et al., "Miniaturized Flexible Amperometric Lactate Probe," *Analytical Chemistry*, 65(8):1069–1073 (Apr. 15, 1993).

Wang, J. et al., "Activation of Glassy Carbon Electrodes by Alternating Current Electrochemical Treatment," *Analytical Chimica Acta*, 167:325–334 (January 1985).

Wang, J. et al., "Amperometric biosensing of organic peroxides with peroxidase–modified electrodes," *Analytica Chimica Acta*254:81–88 (1991).

Wang, J. et al., "Screen–Printable Sol–Gel Enzyme–Containing Carbon links," *Analytical Chemistry*, 68(15). 275–2708 (Aug. 1, 1996).

Wang, J. et al., "Sol–Gel Derived Metal–Dispersed Carbon Composite Amperometric Biosensors," *Electronalysis*, 9(1):52–53 (1997).

Wiliams, D. L. et al., "Electrochemical–Enzymatic Analysis of Blod Glucose and Lactate," *Anal Chem*, 42(1): 118–121 (January 1970).

Wilson G. S. et al., "Progress toward the Development of an Implantable Sensor for Glucose," *Clinical Chemistry*, 38(9): 161391617 (1992).

Yabuki, S. et al., "Electro–conductive Enzyme Membrane," *J. Chem. Soc. Chem. Commun.*, 945–946 (1989).

Yang, L. et al., "Determination of Oxidase Enzyme Substrate Using Cross–Flow Thin–Layer Amperometry," *Electroanalysis*, 8(8–9):716–721 (1996).

Yao, S.J. et al., "The Interference of Ascorbate and Urca in Low–Potential Electrochemical Glucose Sensing". *Proceedings of the Twelfth Annual International Conference of the IEEE Engineering in Medicine and Biology Society*, 12(2): 487–489 (Nov. 1–4, 1990).

Yao, T. et al., "A Chronically–Modified Enzyme Membrane Electrode As An Amperometric Glucose Sensor," *Analytical Chimica Acta*, 148:27–33 (1983).

Ye, L. et al., "High Current Density "Wired"Ouinoprotein Glucose Dehydrogenase Electrode." *Anal. Chem.*65(3): 2389241 (Feb. 1, 1993).

Yildiz, A. et al., "Evlauation of an Improved Thin–Layer Electrode," *Analytical Chemistry*, 40(70): 1018–1024 (June 1968).

Zamzow, K. et al., New Wearable Continuous Blood Glucose Monitor (BGM) and Artificial Pancreas (AP), *Diabetes*. 39:5A(20)(May 1990).

Zhang, Y. et al., "Application of cell culture toxicity tests to the development of implantable biosensors," *Biosensors & Bioelectronics*, 6:653–661 (1991).

Zhang, Y. et al., "Elimination of ther Acetaminophen Inferference in an Implantable Glucose Sensor," *Anal. Chem.*66:1183–1188 (1994).

\* cited by examiner

SUBCUTANEOUS GLUCOSE ELECTRODE

This application is a Continuation of application Ser. No. 09/477,053, filed Jan. 3, 2000, now U.S. Pat. No. 6,162,611 which is a Continuation of application Ser. No. 09/356,102, filed Jul. 16, 1999, which is a Continuation of application Ser. No. 08/767,110, filed Dec. 4, 1996, which is a continuation of application Ser. No. 08/299,526, filed Sep. 1, 1994, now U.S. Pat. No. 5,593,852, which application(s) are incorporated herein by reference.

This is a continuation in part of U.S. patent application Ser. No. 08/161,682 filed Dec. 2, 1998 now U.S. Pat. No. 5,356,786 which is hereby incorporated by reference for all purposes.

This word was supported in part by the National Institutes of Health (DK42015). Accordingly, the U.S. government may have right in this invention.

FIELD OF THE INVENTION

The present invention relates to in vivo enzyme biosensors and more specifically to miniature glucose sensors for subcutaneous measurement of glucose with one-point calibration.

BACKGROUND

In response to the need for frequent or continuous in vivo monitoring of glucose in diabetics, particularly in brittle diabetes, a range of possible in vivo glucose electrodes have been studied. The desired characteristics of these electrodes include safety, clinical accuracy and reliability, feasibility of in vivo recalibration, stability for at least one hospital shift of eight hours, small size, ease of insertion and removal, and a sufficiently fast response to allow timely intervention. The in vivo recalibration should be based upon withdrawal of a single sample of body fluid, e.g., blood, and measuring its glucose concentration. This is termed "one point calibration".

Keys to safety are absence of leachable components, biocompatibility, and limiting of the potentially hazardous foreign matter introduced into the body to an amount that is inconsequential in a worst case failure. The clinical accuracy must be such that even when the readings are least accurate, the clinical decisions based on these be still correct. Feasibility of prompt confirmation of proper functioning of the sensors and of periodic in vivo recalibration is of essence if a physician is to allow the treatment of a patient to depend on the readings of the sensor. This one-point calibration, relying on the signal at zero glucose concentration being zero and measuring the blood glucose concentration at one point in time, along with the signal, is of essence, but has heretofore been elusive. The sensitivity must be sufficiently stable for the frequency of required in vivo recalibration to not be excessive. The sensor must be small enough to be introduced and removed with minimal discomfort to the patient and for minimal tissue damage. It is preferred that the sensor be subcutaneous and that it be inserted and removed by the patient or by staff in a physician's office. Finally, its response time must be fast enough so that corrective measures, when needed, can be timely.

In response to some of these needs, needle type and other subcutaneous amperometric sensors were considered. The majority of these utilized platinum-iridium, or platinum black to electrooxidize $H_2O_2$ generated by the glucose oxidase (GOX) catalyzed reaction of glucose and oxygen. In these sensors, the GOX was usually in large excess and immobilized, often by crosslinking with albumin and glutaraldehyde. To exclude electrooxidizable interferants, membranes of cellulose acetate and sulfonated polymers including Naflon™ were used. Particular attention was paid to the exclusion of the most common electrooxidizable interferants; ascorbate, urate and acetaminophen. Also to cope with interferants, two-electrode differential measurements were used, one electrode being sensitive to glucose and electrooxidizable interferants and the other only to interferants. One strategy for overcoming the problem of interferants, applicable also to the present invention, involves their preoxidation. Another strategy involves shifting, through chemical changes, the redox potential of the polymer in the sensing layer to more reducing potentials. When the redox potential of the polymer is in the region between about −0.15 V and +0.1 V versus the standard calomel electrode (SCE), and the electrodes are poised in their in vivo operation between about −0.10 and +0.25 V, the rate of electrooxidation of interferants such as ascorbate, urate, and acetaminophen is very slow relative to that of glucose through its physiological concentration range. Thus, also the currents from electrooxidation of interferants are small relative to those of glucose.

To make the electrodes more biocompatible, hydrophilic polyurethanes, poly(vinyl alcohol) and polyHEMA membranes have been used.

Several researchers tested GOX-based glucose sensors in vivo and obtained acceptable results in rats, rabbits, dogs, pigs, sheep and humans. These studies validated the subcutaneous tissue as an acceptable glucose sensing site. Good correlation was observed between intravascular and subcutaneous glucose concentrations. They also demonstrated the need for in vivo sensor calibration. Another approach to in vivo glucose monitoring was based on coupling subcutaneous microdialysis with electrochemical detection. To control and adjust the linear response range, electrodes have been made glucose-diffusion limited, usually through glucose transport limiting membranes.

Diffusional mediators, through which the $O_2$-partial pressure dependence of the signals is reduced, are leached from sensors. Such leaching introduces an unwanted chemical into the body, and also leads to loss in sensitivity, particularly in small sensors. In microsensors, in which outward diffusion of the mediator is radial, the decline in sensitivity is rapid. This problem has been overcome in "wired" enzyme electrodes, i.e., electrodes made by connecting enzymes to electrodes through crosslinked electron-conducting redox hydrogels ("wires"). Glucose oxidase has been "wired" with polyelectrolytes having electron relaying $[Os(bpy)_2Cl]^{+/2+}$ redox centers in their backbones. Hydrogels were formed upon crosslinking the enzyme and its wire on electrodes. These electrodes had high current densities and operated at a potential of 0.3V vs. SCE. The electrooxidizable interferants are eliminated through peroxidase-catalyzed preoxidation in a second, nonwired, hydrogen peroxide generating layer on the "wired" enzyme electrode.

SUMMARY OF THE INVENTION

A small (e.g., 0.29 mm), recessed, non-corroding metal (e.g., gold, platinum, palladium) or carbon wire electrode for subcutaneous in vivo glucose monitoring, approaching in its performance all of the above listed requirements, including in vivo one-point calibration, has been produced. The electrode was constructed by depositing active polymer layers into a recess formed by etching away gold from an insulated gold wire.

The active polymer layers, including a sensing layer, a glucose flux-limiting layer, a biocompatible layer, and optionally a peroxidase-based interferant eliminating layer, were protected within the recess against mechanical damage. (The peroxidase-based interferant eliminating layer is not required when a lower redox potential polymer is used, as described above.) The recess and its polymer layers also reduced the transport of glucose to the wire electrode contacting sensing layer.

By limiting the glucose flux, the desired linear response range, spanning the clinically relevant glucose concentration range was obtained. The inventive biosensors are able to accurately measure, for example, approximately 2–30 m$\mu$ glucose and approximately 0.5–10 m$\mu$ lactate, in vivo. The sensor has no leachable components, and its four crosslinked polymer layers contain only about 5 $\mu$g of immobilized material, and only a few monograms of polymer-bound osmium. Preoxidation of the interferants in one of the four layers makes possible one-point in vivo calibration of the sensor.

DETAILED DESCRIPTION OF THE INVENTION

Figure 1:
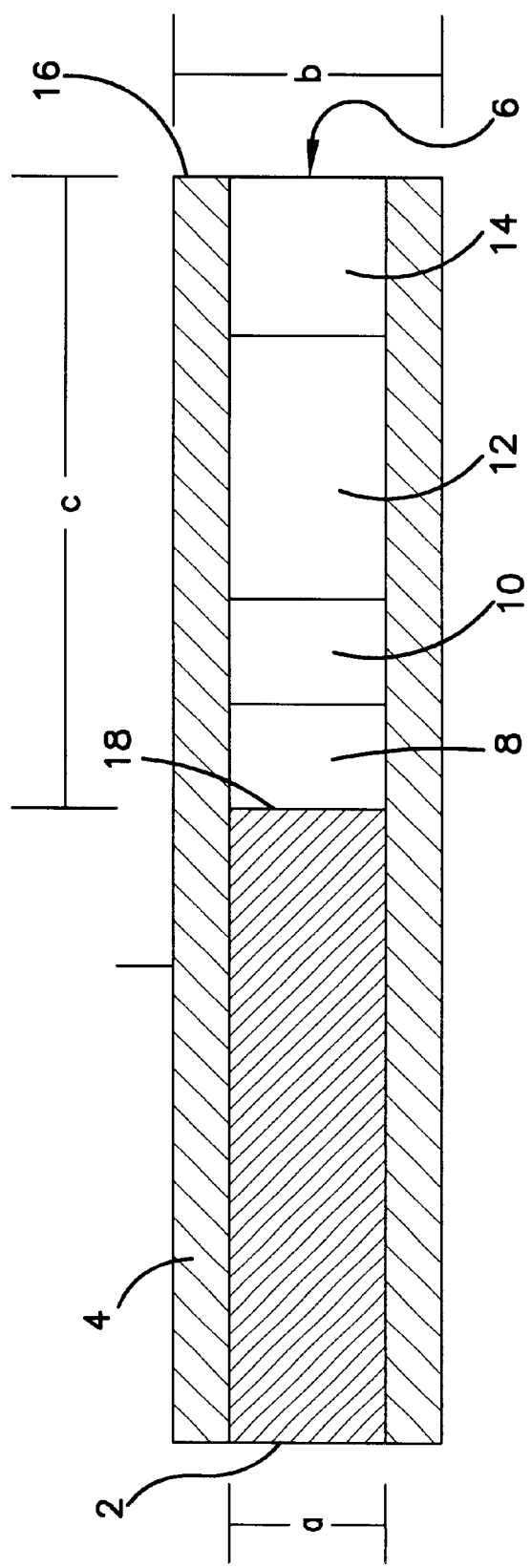
FIG. 1 is a schematic drawing of an electrode of the present invention.

The present invention includes an insulated, non-corroding conducting metal (e.g., gold, platinum, palladium) or carbon wire-based small (e.g., 290 $\mu$m) O.D. subcutaneous glucose sensor, allowing one-point calibration in vivo. As shown in FIG. 1, its construction involves coating a small (e.g., 250 $\mu$m) diameter non-corroding metal or carbon wire 2 with an electrically insulating material 4, e.g., a polyimide, and, layering in a recess 6 formed by etching or removing a portion of the metal or carbon, the following active polymer layers: an immobilized, "wired," glucose oxidase layer 8; an electrically insulating and glucose diffusion limiting layer 10 formed, for example, by crosslinking a polyallylamine (PAL) with a polyaziridine (PAZ); optionally, an interference eliminating layer 12, e.g., of crosslinked horseradish-peroxidase and lactate oxidase; and a biocompatible film 14 e.g., of poly(ethylene oxide) (PEO) derivatized to allow its photo-crosslinking. The outside diameter a of the wire 2 is preferably about 0.25 mm or less, and the outside diameter b of the insulated wire is preferably about 0.3 mm or less. The recess 6 in the insulated electrode extends from the tip 16 of the electrode which is open to the surrounding environment, to the top 18 of the wire 2 in the insulating sheath, generally for a length c of less than about 0.150 mm, and preferably about 0.125 mm.

The electrodes have no leachable components. The total amount of polymers and enzymes is preferably about 5 $\mu$g. The glucose response through the physiologically relevant 2–20 mM concentration range is close to linear. The electrodes do not respond to ascorbate, urate or acetaminophenol for at least about 36 hours. Their 10–90% response time is about 90 seconds at 2 mM glucose and about 30 seconds at 20 mM glucose. Their sensitivity, after about 30 minutes equilibration, is stable for about 72 hours at 37° C. in 10 mM glucose, the current deviating from the average by less than ±5%. The electrodes have substantially no signal output, e.g., current, charge, or potential, when the concentration of the analyte to be measured is zero.

Two electrodes implanted subcutaneously in a rat tracked blood glucose levels, and their absolute, uncorrected current output was proportional to the blood glucose concentration. Analysis of the correlation between the blood glucose levels in the tail vein and the current output of the sensors in the subcutaneous regions of the thorax and between the scapulae of the same rat showed that even when the probed sites and organs differed in the extreme, one point in vivo calibration was valid. The analysis also showed the value of implanting redundant sensors. Had clinical decisions been made based on individual sensor readings, calibrated at one point, 94% would have been clinically correct. By using redundant sensors and accepting only those pairs of readings that were within one standard deviation, the percentage of the clinically correct decisions was increased to 99%.

It is understood that one of skill in the art may substitute various components of the biosensor described above with known materials to obtain an modified biosensor using the principles outlined herein. For example, the following substitutions are contemplated:

Base electrode: The base electrode of the inventive sensor may be formed of a non-corroding metal or carbon wire, for example vitreous carbon, graphite, platinum, palladium, or gold. Gold is preferred, and is used in the following illustrative examples of the invention.

Insulator: The conductive metal or carbon wire is coated with an electrically insulating material, which also forms a wall about the recess which houses the active polymeric components. The insulating material may be, for example, polyurethane, teflon (fluorinated polymers), polyethyleneterephthalate (PET, Dacron) or polyimide. The insulating material is preferably a biocompatible polymer containing less than about 5% water when in equilibrium with physiological body fluids, e.g., subcutaneous tissue.

Recess: In general, the recess at the tip of the electrode is approximately 20 to 150 µm in length c, and preferably is approximately 50 to 125 µm.

Etching method: The method for etching metal from the tip of the electrode described herein may utilize chloride, bromide or iodide in the bath in lieu of cyanide as described. Bromide is preferred, because it is less toxic and, like $Au(CN)_2^-$, $AuBr_4^-$ is a water soluble anion. Thus, in aqueous HBR, the metal, e.g., gold, an be etched by applying a sufficiently oxidizing potential where gold is electrolytically dissolved:

Wired Enzyme Layer: In the sensing enzyme-containing layer, glucose oxidase may be substituted with other redox enzymes to measure other relevant clinical compounds. For example, lactate oxidase may be used for the in vivo detection of lactate, important in determining if an organ is receiving sufficient oxygen through the blood.

Useful redox polymers and methods for producing the sensing layer are described, for example, in U.S. Pat. Nos. 5,264,104; 5,356,786; 5,262,035, and 5,320,725. Additional redox polymers include, for example, poly(1-vinyl imidazole); poly(4-vinyl pyridine); or copolymers of 1-vinyl imidazole such as poly (acrylamide co-1-vinyl imidazole) where the imidazole or pyridine complexes with $[Os (bpy)_2 Cl]^{+/2+}$; $[Os (4,4'\text{-dimethyl bipyridine})_2 Cl]^{-/2+}$; $[Os (4,4'\text{-dimethyl phenanthroline})_2 Cl]^{+2/+}$, $[Os (4,4'\text{-dimethyoxy phenanthroline})_2 Cl]^{+/2+}$; and $[Os (4,4'\text{-dimethoxy bipyridine})_2 Cl]^{+/2+}$; to imidazole rings. The imidazole ring compounds are preferred because their complexes have more reducing redox potentials, i.e., closer to that of the SCE potential. At these more reducing potentials, the rate of electrooxidation of interferants and the current generated thereby.

Barrier Layer: The polymeric barrier layer is electrically insulating and limits diffusion of glucose through to the sensing layer. It may be formed, for example, by crosslinking a polyallylamine (PAL) with a polyaziridine (PAZ). Alternatively, PAL may be replaced wholly or in part with a zwitterionic polymer obtained by quaternizing poly (vinylpyridine) with bromoacetate and dialyzing against 0.15M NaCl or by a polyanion such as a polysulfonic acid.

The barrier layer may contain a polyanionic polymer, in which the rate of permeation of anionic interferants such as ascorbate and urate is slowed. This layer may also contain a polycation that enhances the retention of the polyanion by electrostatic bonds and improves wetting by the biocompatable layer.

Interference Eliminating Layer: As described above, this layer is optional, in that it is not required when a redox polymer having a more reducing potential is used, such as $PVI_{15}\text{-dmeOs}$ (Ohara et al., *Analytical Chemistry*, 1994, 64:2451–2457). At operating potentials of approximately −0.10 to +0.25 for the glucose biosensor, the rate of electrooxidation of interferants such as ascorbate, urate and acetaminophen is very slow relative to that of glucose through its physiological concentration range.

When a separate interferant eliminating layer is used, it preferably contains a peroxidase enzyme which may or may not be preactivated. Such interferant eliminating layers are disclosed, for example, in U.S. Pat. No. 5,356,786 which discloses the structure and function of interferant eliminating biosensors. The glucose biosensor preferably contains lactate oxidase (LOX) in combination with peroxidase in the interferant eliminating layer. However, for biosensors used to detect lactate, glucose oxidase would be used with peroxidase. In a similar manner, the enzyme composition of the interferant eliminating layer may be altered for a specified function.

Biocompatable Layer: In general, the biocompatible layer is comprised of hydrogels, e.g., polymeric compositions which contain more than about 20% by weight of water when in equilibrium with a physiological environment such s living tissue or blood. An example is crosslinked poly (ethylene oxide), e.g., poly(ethylene oxide) tetraacrylate. The polymeric compositions must be non-toxic and compatible with living systems.

Method for making multi-layered recessed biosensors: Insulated non-corroding metal or carbon wires that have been etched as described above to contain a recess at the tip, are placed in a block that serves as an X-Y positioner. The wires vertically traverse the block and are held in place, e.g., by pressure. The blocks with the wires can be formed of elements, each element having multiple half-cylinder grooves running vertically. The wires are placed in these grooves and the elements are assembled into the block using screws. For example, the block may be formed of aluminum having equally spaced holes, (900 for a 30×30 array of wires), each hole to contain one wire. The block is positioned under a fixed micronozzle that ejects a fluid in to the recess of the insulated wire.

To reduce the requirement of precision in the positioning of the block and the micronozzle, the nozzle is electrically charged, with the wire having an opposite charge, or the wire being grounded or at least having a potential such that there is a potential difference between the nozzle and the wire. Because the nozzle is charged, the microdroplets it ejects are also charged with the same type of charge (positive or negative) as the nozzle. The higher the potential on the nozzle (e.g., versus ground potential), the higher the charge on the ejected microdroplets. If the tip of the wire to be coated is at ground potential or has a charge of the opposite type, the charged microdroplets are guided into the recess to deposit on the electrode, even if the jet of microdroplets is not vertical, i.e., even if the micronozzle is not precisely aligned above the wire's tip.

Furthermore, the higher the electrical potential on the nozzle (relative to ground) the greater the charge on the ejected microdroplet. When the charge is high enough, the droplet breaks up into two or more smaller droplets because of electrostatic repulsion of charges on the droplet. Thus, the very small droplets all "drift" (drift meaning transport assisted by an electrical field) to the recessed electrode surface and are collected on it, even if they did not originate in a nozzle precisely aligned with the electrode.

This coating method is useful in making any small biosensor, not only those in recessed zones.

Clinical Use of the Recessed Biosensors:

The recessed biosensors of the present invention have sufficient sensitivity and stability to be used as very small, subcutaneous biosensors for the measurement of clinically relevant compounds such as glucose and lactate. The electrodes accurately measure glucose in the range of about 2–30 μM and lactate in the range of about 0.5–10 mM. One function of the implanted biosensor is to sound an alarm when, for example, a patient's glucose concentration is too low or too high. When pairs of implanted electrodes are used, there are three situations in which an alarm is triggered; low glucose concentration, high glucose concentration; sensor malfunction as determined by a discrepancy between paired readings of the two sensors. A discrepancy sufficient to trigger the alarm may be, for example more than two or three times the standard deviation persisting for a defined period, e.g., not less than ten minutes. Such a system may be useful in sleeping patients, and also in emergency and intensive care hospital rooms, where vital functions are continuously monitored.

Another function of the inventive biosensors in to assist diabetics in maintaining their blood glucose levels near normal. Many diabetics now maintain higher than normal blood glucose levels because of danger of coma and death in severe hypoglycemia. However, maintaining blood glucose levels substantially, e.g., approximately 40% or more above normal leads to retionopathy and blindness as well as to kidney failure. Use of the subcutaneous biosensors to frequently, if not continuously, monitor glucose concentrations is desirable so that glucose concentrations can be maintained closer to an optimum level.

The subcutaneous biosensors can be used to measure the rate of rise and decline of glucose concentrations after a meal or the administration of glucose (e.g., a glucose tolerance test). The sensors are also useful in feedback loops for automatic or manually controlled maintenance of glucose concentrations within a defined range. For example, when used in conjunction with an insulin pump, a specified amount of insulin is delivered from the pump if the sensor glucose reading is above a set value.

In all of these applications, the ability to promptly confirm that the implanted sensor reading is accurate is essential. Prompt confirmation and rapid recalibration are possible only when one-point calibration is valid. Generally, even if a sensor's response is linear through the relevant concentration range, calibration requires at least two blood or fluid samples, withdrawn from the patient at times when the glucose concentration differs. It usually takes several hours for the glucose concentration to change sufficiently to validate proper functioning by two-point calibration. The ability to confirm and recalibrate using only one point is thus a highly desirable feature of the present invention.

Redundant sensors (e.g., at least two) are preferred in the clinical application of the subcutaneous biosensors. Such redundancy permits signaling of failure of any one sensor by recognition of an increase in the discrepancy between the readings of the sensors at one time point, e.g., more than two standard deviations apart. The redundant sensors may be implanted near each other or at remote sites.

It is preferred that the biosensors be implanted in subcutaneous tissue so as to make the sensor relatively unobtrusive, and at a site where they would not be easily dislodged, e.g., with turning or movement. It is also preferred, when readings are not corrected for temperature (which they generally are) that the sensors be implanted where they are likely to be at body temperature, e.g., near 37° C. and preferably covered by clothing. Convenient sites include the abdomen, inner thigh, arm.

Although we described here continuous current measurement for assaying glucose, the electrical measurement by which the glucose concentration is monitored can be continuous or pulsed. It can be a current measurement, a potential measurement or a measurement of charge. It can be a steady state measurement, where a current or potential that does not substantially change during the measurement is monitored, or it can be a dynamic measurement, e.g., one in which the rate of current or potential change in a given time period is monitored. These measurements require at least one electrode in addition to the sensing electrode. This second electrode can be placed on the skin or can be implanted, e.g., subcutaneously. When a current is measured it is useful to have a potentiostat in the circuit connecting the implanted sensing electrode and the second electrode, that can be a reference electrode, such as an Ag/AgCl electrode. When a current is measured the reference electrode may serve also as the counter electrode. The counter electrode can also be a separate, third electrode, such as a platinum, carbon, palladium or gold electrode.

In addition to implanting the sending electrode in the body, fluid from the body, particularly fluid from the subcutaneous region, can be routed to an external sensor, it is preferred in this case to implant in the subcutaneous region a microfiltration given and pull fluid to an evacuated container, the fluid traversing a cell containing the sensing electrode. Preferably this cell also contains a second electrode, e.g., a reference electrode which may serve also as a counter electrode. Alternatively, the reference and counter electrodes may be separate electrodes. In coulometric measurements only two electrodes, the sensing electrode and the counter electrode are required. The flow of body fluid may be pulsed or continuous. Other than an implanted microfiltration fiber, also a microdialysis fiber may be used, preferably in conjunction with a pump.

Increased stability of the biosensors:

To increase the stability and useful life of the inventive biosensors, it is advantageous to use intrinsically more stable enzymes and redox polymers. However, even if the enzyme and redox polymer degrade in the glucose electrooxidation process by which the signal (current) is generated, it is possible to greatly extend and useful life of the implanted electrodes and reduce the frequency of their required recalibration after implantation.

A simple measure by which the life of the implanted electrodes can be extended and the frequency of their required recalibration reduced involves turning the electrodes "on" by applying a bias, i.e., a potential, only during the period of measurement, then turning the biasing potential off or reducing it, so that a lesser current will flow. It is generally sufficient to perform only one measurement every five or even ten minutes, or longer, because glucose concentrations do not change abruptly.

Another measure is to lower the glucose flux to the sensing layer much as possible, consistent with maintaining adequate sensitivity and detectivity. Reduction of the glucose flux to the sensing layer reduces the current. Therefore, even though this stabilizer the electrodes, i.e., slows the loss in sensitivity, the flux dependent current must not be excessively reduced. Usually a current of 3–5 nA at 2 mM glucose concentration is adequate. When the glucose flux is lowered by using one or more glucose-flux reducing polymer slayers, such as the PAL/PAZ layer, the lifetime of the sensor is increased.

EXAMPLES

Example 1

Electrode Preparation

Electrodes were made of a polyamide-insulated 250 μm diameter gold wire, having an outer diameter (O.D.) of 390

μm (California Fine Wire Co., Gover City, Calif.). Heat shrinkable tubing (RNF 100 3/64" BK and 1/16" KB, Thermofit®, Raychem, Menlo Park, Calif.) and a two component silver epoxy (Epo-tek H₂OE, Epxy Tech, Inc., Billerica, Mass.) were used for electrode preparation.

The glucose sensing layer was made by crosslinking a genetically engineered glucose oxidase (rGOX) (35% purity, Chiron Corp., Emergville, Calif.) with a polymer derived of poly(vinylimidazole) (PVI), made by complexing part of the imidazoles to $[Os(bpy)_2Cl]^{+/2+}$. The resulting redox polymer, termed PVI-Os, was synthesized according to a previously published protocol. (Ohara et al., 1993, *Anal. Chem.*, 65:24). Poly(ethylene glycol) diglycidyl ether 400 (PEDGE; Polysciences, Warrington, Pa.) was used as the crosslinker.

The barrier layer between the sensing and interference-eliminating layers was made of polyallylamine (PAL; Polysciences) crosslinked with a polyfunctional aziridine (PAZ) (XAMA-7; Virginia Chemicals, Portsmouth, Va.).

the interference-eliminating layer was prepared by co-immobilizing horseradish peroxidase (HRP) type VI (Cat. no. P-8375, 310 U/mg, denoted herein as HRP-VI, Sigma, St. Louis, Mo.) and HRP for immunological assay (No. 814407, min 1000 U/mg, denoted HRP-BM, Boehringer-Mannheim, Indianapolis, Ind.) with lactate oxidase from *Pediococcus sp.* (Cat. No. 1361, 40 U/mg denoted LOX, Genzyme, Cambridge, Mass.) and a recombinant microbial source (Cat. No. 1381 denoted rLOX, Genzyme). Co-immobilization was performed using sodium periodate (Cat. No. S-1147, Sigma) according to the methods described in Maidan and Heller, 1992, *Anal. Chem.* 64:2889–2896.

The biocompatible layer was made of 10% aqueous poly(ethylene oxide) tetraacrylate (PEO-TA). To form the photocrosslinkable polymer, PEO was acrylated by reaction with acryloyl chloride. The 18,500 g/mol PEO (Polysciences) is a tetrahydroxylated compound by virtue of two hydroxyl groups on a bisphenol A bisepoxide that linked tow $\alpha$, $\omega$-hydroxy-terminated 9,000 g/mol PEO units. Acryloyl chloride (Aldrich, Milwaukee, Wis.) in a 2 to 5 molar excess was used to acrylate the polymer (10% w/v PEO in benzene). Triethylamine (Mallinkrodt, Paris, Ky.) was used as a proton acceptor equimolar with the acryloyl chloride.

Other chemicals used were bovine serum albumin (BSA) fraction V (Cat. No. A-2153), BSA, ascorbic acid, uric acid, 4-acetaminophenol, L(+)=lactic acid, and hydrogen peroxide 30%, all from Sigma. All chemicals were used as received. Solutions (if not otherwise specified) were made with distilled, deionized water. Glucose monitoring was performed in buffer, in bovine serum (Sigma, Cat. No. S-6648) containing antibiotic-antimycotic solution (Sigma, Cat. No. A-8909) at 37° C. and in rats.

Instrumentation

In making the recessed gold electrodes, a potentiostat/galvanostat (PAR Model 173, Princeton Applied Research, Princeton, N.J.) operated in a galvanostatic mode, and a sonicator (Fisher Scientific, Pittsburgh, Pa.) were used. Cyclic voltammograms were recorded with a potentiostat (PAR Model 273A) and a conventional electrochemical cell having a Pt wire counter and a SCE reference electrode and were evaluated with PAR 270 software. Glucose signals were monitored with a bipotentiostat (Biometra EP 30) and a two channel strip-chart recorder. The recessed electrodes were coated under a microscope (Bausch & Lomb) using a micromanipulator (Narishige, Seacliff, N.Y.). The micropipettes were pulled with a micropipette puller (Narishige). Temperature was controlled with an isothermal circulator (Fisher Scientific).

Electrode Preparation:

Five cm lengths of polyamide insulated gold wire were cut with a sharp razor blade. Electrical contact was made at one end with silver epoxy to an insulated stainless steel wire and the junction was covered with insulating heat shrinkable tubing. The recess forming electrochemical etching process was carried out in 10 ml of 3M potassium cyanide, with the gold wire as the working electrode and a platinum or gold wire as the counter electrode. The wires were placed in contact with the bottom of the beaker, all electrodes being equidistant from the counter electrode. The beaker was sonicated during the etching procedure. The ends of the gold wires were bent upwards, so that agitation by the sonicator caused the oxygen bubbles formed during the etching process to rise and escape. The electrodes were then thoroughly washed and immersed in water for 30 minutes.

A recess 6, i.e., channel, in a polyamide insulated gold wire 2 is formed by electrochemical etching of the gold under galvanostatic control. By controlling the charge, the total amount of gold electrooxidized and dissolved as $Au(CN)_2$ is defined. When the conditions were set so that the $CN^-$ transport into the channel and the $Au(CN)_2^-$ transport out of it are not rate limiting, (e.g., sonicated bath and high concentration of potassium cyanide, at least approximately 0.2M, and preferably 3M), a flat gold wire surface is produced at the bottom of channels with aspect ratios of 0.5 to 2.0. Thus, when the CN-concentration is high enough and the wires are ultrasonically vibrated, the tips of gold wires are flat. Passage of 1.5 coulombs per electrode at 8 mA current produced approximately 125 μm deep cavities or channels. At theoretical efficiency for one-electron oxidation 3.08 mg of gold would have been etched. The amount of gold actually etched was only 0.076 mg, showing significant $CN^-$ or water oxidation. Nevertheless, the process is reproducible, accurate and fast with 20 electrodes being processed in each batch in less than five minutes. The recess-forming procedure was highly reproducible, with a deviation of ±10 μm found (using an objective micrometer) for a batch of 30 recessed electrodes. Before coating, the electrodes were examined under a microscope for flatness of the gold surface and correct depth.

FIG. 1 shows a schematic side view in cross-section of an electrode of the present invention, showing the gold wire 2, insulating coating 4, and recess or channel 6. The recessed gold surfaces were coated by filling of the cavities or channels 6 with aqueous solutions containing the crosslinkable components of the different layers, and their crosslinkers. The solutions were introduced under a microscope with a micropipette (connected to a microsyringe by polyethylene tubing and shrink tubing), using a micromanipulator. After application of each of the individual layers, the electrodes were cured overnight at room temperature, in air.

Electrode structure:

The electrodes were prepared by sequentially depositing four layers within the recess or channel 6. The layers were: the sensing layer 8, the insulating layer 10, the interference-eliminating layer 12 and the biocompatible layer 14. The sensing layer, containing "wired" redox enzyme is positioned adjacent to and in contact with the gold wire 2. The insulating layer 10 is positioned between the sensing layer 8 and the peroxidase-based interferant-eliminating layer 12. The biocompatible layer 14 fills the remaining space in the recess 6 and is in contact with the environment outside the electrode. The thin polymer layers are well protected by containment within the polyamide sleeve 4.

The sensing layer 8 was made by "wiring" rGOX to the gold electrode through a redox hydrogel to which the enzyme was covalently bound. The electrodes were prepared as follows: 10 mg/ml solutions were made from 1. the PVI-Os redox polymer in water,
2. the crosslinker, PEGDGE, in water, and
3. the enzyme, rGOX, in a 10 mM HEPES solution adjusted to pH 8.15.

A redox hydrogel was formed by mixing the three solutions so that the final composition (by weight) was 52% redox polymer, 35% enzyme and 13% crosslinker.

The insulating layer 10 prevented electrical contact between the redox hydrogel and the interference eliminating enzymes (HRP and LOX). PAL:PAZ was used as the insulating material. The film was deposited from a solution obtained by mixing in volume ratio of 1/1, 1/2 or 1/3, a PAL solution (4.5 mg in 100 MM HEPES buffer at pH 7.0) and a freshly prepared PAZ solution (30 mg/ml). The PAZ solution was used within 15 minutes of preparation.

The interference-eliminating layer 12 was prepared according to a previously published protocol, Maidan and Heller, 1992, Anal. Chem., 64:2889–2896. 50 µl of a 12 mg/ml freshly prepared sodium periodate solution was added to 100 µl of a solution containing 20 mg/ml HRP (HR-VI or HRP-BM) and 100 mg/ml LOX (LOX or rLOX) in 0.1 M sodium bicarbonate and the mixture was incubated in the dark for two hours. Alternatively, the oxidation of HRP could be carried out prior to adding LOX and crosslinking.

The biocompatible layer 14 films were photocrosslinked by exposure to UV light (UVP, Inc., San Gabriel, Calif.; Blak-Ray; spectral peak at 360 nM, UV irradiance at the sample 200 mW/cm$^2$) for one minute. The initiator used was 2,2-dimethoxy-2-phenylacetophenone (Aldrich). A solution of 300 mg/ml of the initiator in 1-vinyl-2-pyrrolidinone (Aldrich) was added to the prepolymer mixtures. Approximately 30 µl of the initiator solution was added per ml of 10% w/w aqueous solution of the tetraacrylated PEO. The prepolymers were crosslinked in situ inside the recess of the electrode. The films were prepared by filling the recess with the prepolymer solution twice and exposing the electrode to the UV light source after each time the cavity was filled.

In vitro Testing of Electrodes:

In vitro experiments were carried out in batch fashion at 25° and 37° C., using a conventional three electrode electrochemical cell with the enzyme-modified gold wires as the working electrode, a platinum wire as the counter electrode and a saturated calomel reference electrode (SCE). The electrolyte was a 20 mM phosphate buffered-saline solution containing 0.15 M NaCl at pH 7.15. Experiments in serum were performed at 37° C., adding 100 µL antibiotic-antimycotic solution to 10 ml serum. Phosphate buffered-saline and serum were agitated during the experiments. The working potential was +0.3 V versus SCE for experiments with the PVI-Oe polymers.

Structure and Performance: The depth c of the channel 6 and the thickness of the polymer layers in it controls the mass transport, i.e., flux of glucose, to the sensing layer. By controlling these parameters, the apparent Michaelis constant ($K_m$) is adjusted to about 20–30 mM glucose. The polyimide wall 4 of the channel 6 also protects the four polymer and polymer/enzyme layers 8, 10, 12, 14 against mechanical damage and reduces the hazard of their loss in the body. Because the glucose electrooxidation current is limited by glucose mass transport through the recess 16 and its polymer films 8, 10, 12, 14, rather than by mass transport to the tissue-exposed tip 16, the current is practically insensitive to motion. Evidently, the electrooxidation rate of glucose in the recessed sensing layer 8 is slower than the rate of glucose diffusion to the channel's outer fluid contacting interface.

Figure 2:
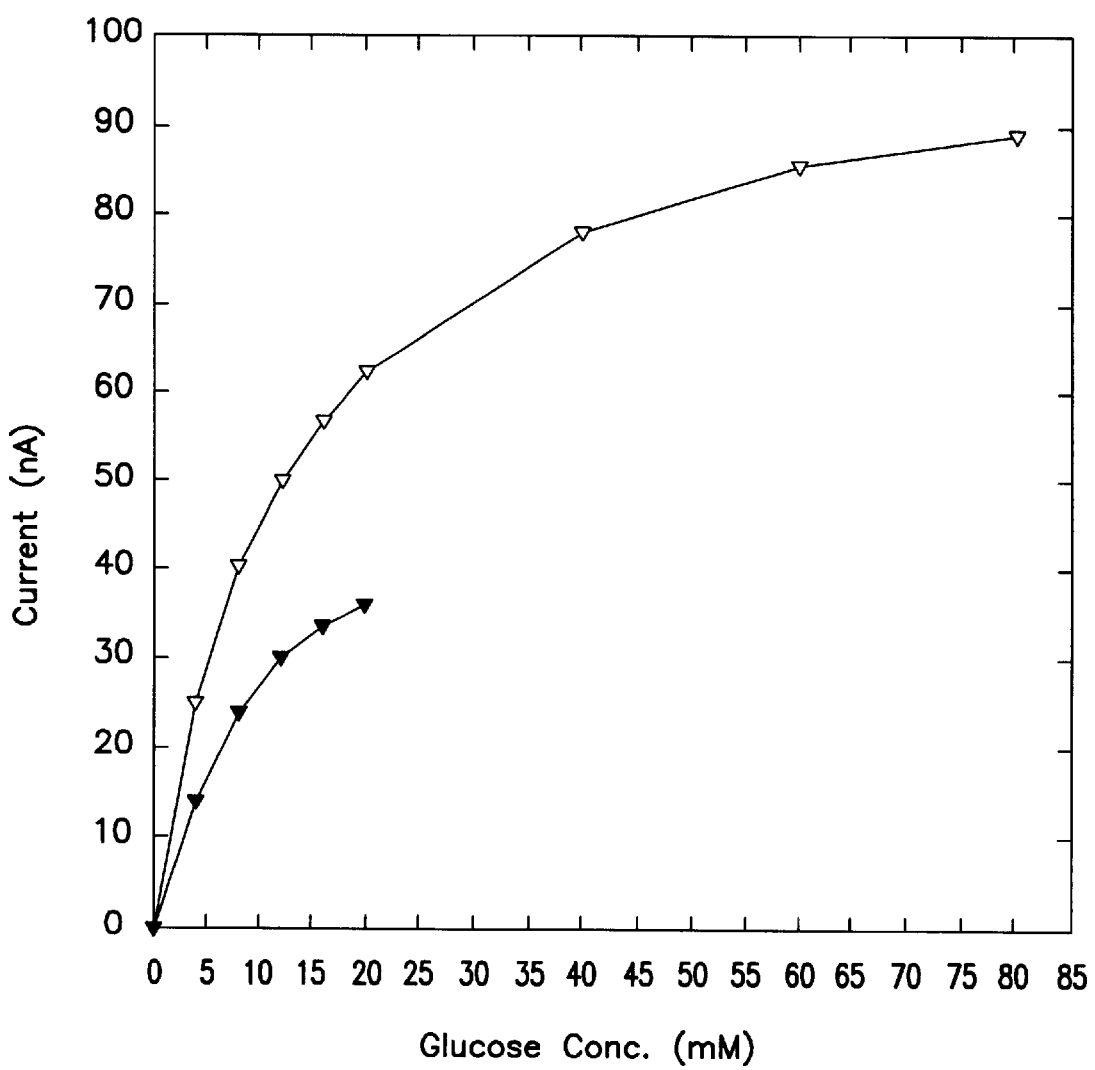
FIG. 2 is a graphical representation of data generated comparing current density of glucose electrooxidation on electrodes made with PIV$_5$-Os (open triangles) with those made with PIV$_3$-Os (filled triangles).

PVI$_5$-Os is preferred as the "wire" of the sensing layer when an interference eliminating layer of HRP and LOX is used, but not in the absence of this layer, i.e., when redox polymers with more reducing redox potential are preferred. The subscript (5) is used to indicate that, on the average, every fifth vinylimidazole mer carries an electron-relaying osmium center. Use of electrodes formed with PVI$_5$-Os and PVI$_3$-Os (every third 1-vinylimidazole mer carrying an osmium center) are compared in FIG. 2, and show higher current density of glucose electrooxidation on electrodes made with PVI$_5$-Os (open triangle) than on those made with PVI$_3$-Os (filled triangles).

Figure 3:
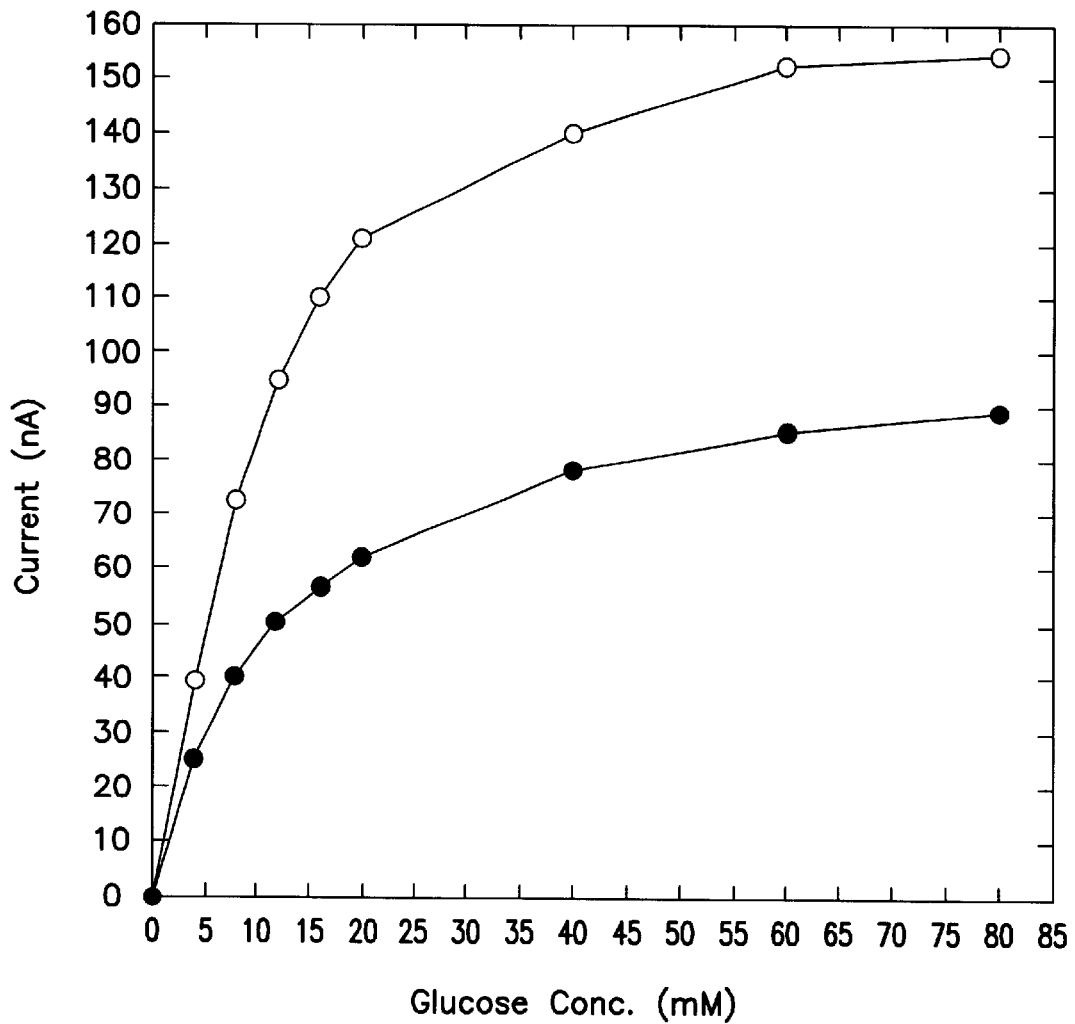
FIG. 3 is a graphical representation of data generated comparing dependency of current generated on the depth of the recess.
Figure 4:
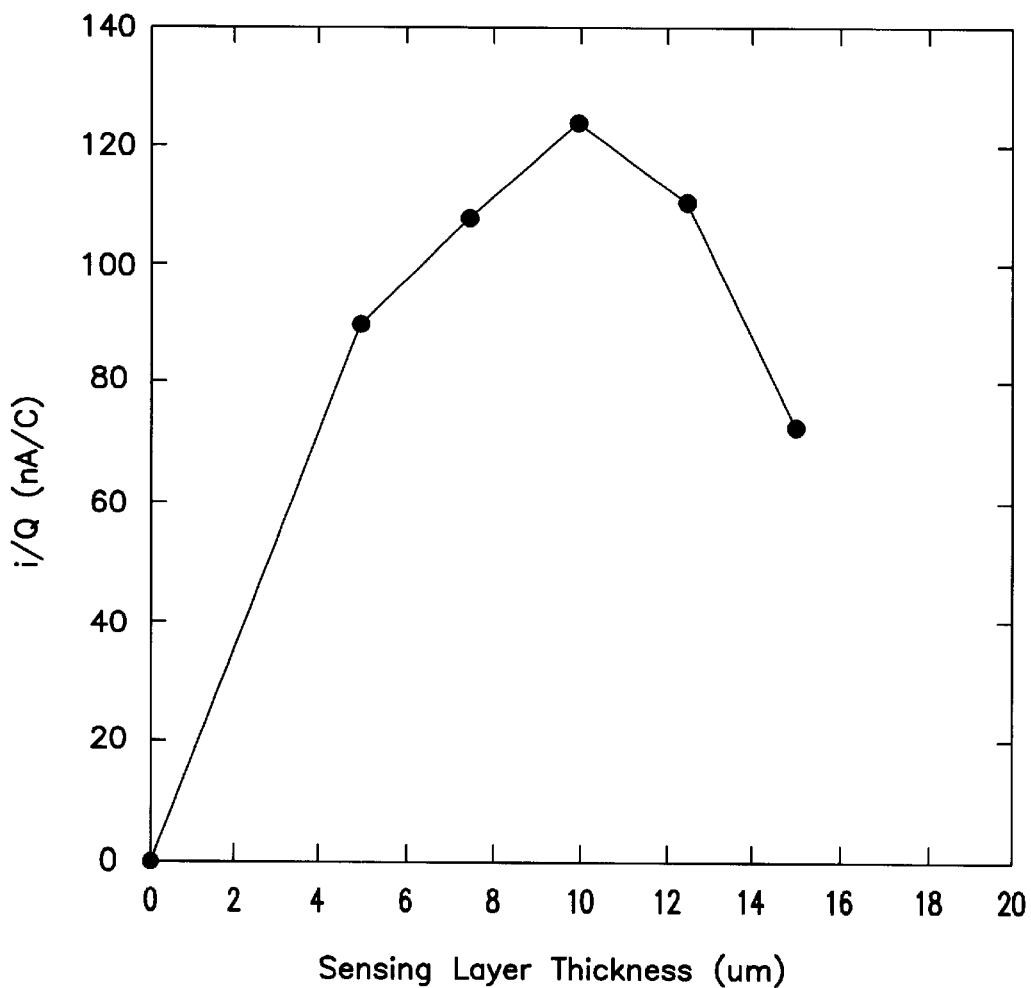
FIG. 4 is a graphical representation of data generated comparing dependency of the ratio of the current generated and the change required to electroreduce or oxidize the polymer redox centers in the sensing layer on the thickness of the sensing layer.

Depth of the recess and the sensing layer: Channels of 125, 250, and 500 µm depth, were investigated to assess the dependence of the current on the depth of the recess (FIG. 3), with the total amount of PVI$_5$-Os and rGOX being kept constant. Much of the loss in current in the deeper cavities resulted not from reduced glucose mass transport, but from adsorptive retention of part of the enzyme and polymer on the polyamide wall when microdrops of the component solutions were introduced into the recess in the process of making the electrodes. Through repeated rinsing with water, some of the adsorbed polymer and enzyme on the walls were washed onto the electrode surface, increasing the current. The highest currents were seen after five washings. When the thickness of the sensing layer was increased through increasing the number of coatings (FIG. 4) the ratio current to charge required to electroreduce or electrooxidize the redox polymer in the sensing layer reached a maximum, then dropped. For the preferred 125 µm recess, 10 coatings, producing an approximately 13 µm thick wired-rGOX sensing layer, yielded sensors that had the desired characteristics for in vivo use.

The insulating layer: This layer electrically insulates the redox enzymes of the interference eliminating layer (HRP and LOX) from the "wired" rGOX layer and limits the glucose flux to the sensing layer, thereby extending the useful life of the electrode. PAL crosslinked with PAZ, forming a polycationic network at pH 7.09 is preferred. The best results, i.e., best stability of current outputs, were obtained using 1:2 PAL:PAZ (FIG. 5), with three coatings applied to form an approximately 7 µm thick crosslinked film.

Figure 6:
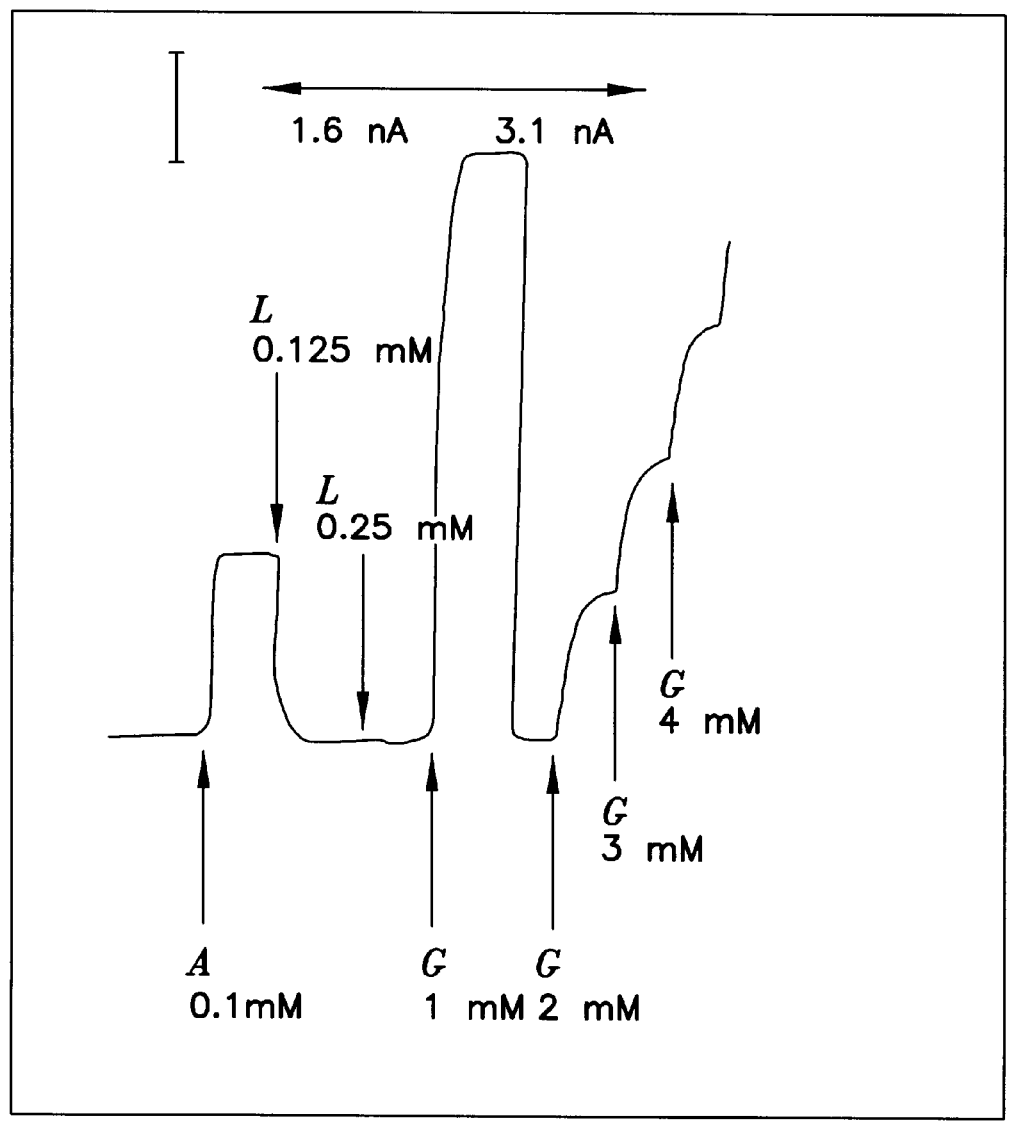
FIG. 6 is a graphical representation of data generated comparing dependency of current generated on the presence of ascorbate, in the absence and pressure of lactate and glucose. The concentrations of ascorbate (A), lactate (L) and glucose (G) are shown. Ascorbate is an electrooxidzable interferant. Upon addition of lactate its electrooxidation current is suppressed while that of glucose is not suppressed.

The interference eliminating layer: Interferants, particularly ascorbate, urate, and acetaminophenol, are oxidized in third layer, containing LOX and HRP. In this layer, lactate, the typical concentration of which in blood is 1 mM, reacts with $O_2$ to form $H_2O_2$ and pyruvate. $H_2O_2$, in the presence of HRP, oxidizes ascorbate, urate, and acetaminophenol, being reduced to water. The preferred coimmobilization process involved two separate steps: periodate oxidation of oligosaccharide functions of HRP to aldehydes, followed by mixing with LOX and formation of multiple Schiff bases between HRP-aldehydes and LOX amines (e.g. lysines) and between HRP aldehydes and amines. The thickness of the interference eliminating layer is approximately 85 µm and is made by applying successive coatings, e.g., about six coatings. FIG. 6 shows that electrooxidizable interferants were eliminated in the presence of lactate at physiological levels. LOX slowly lost its activity in the crosslinked HRP-LOX layer. This led to degradation of the ability of the layer to eliminate interferants. After 36 hours of operation at 37° C., a measurable current increment was noted when enough ascorbate was added to produce a 0.1 mM concentration.

The biocompatible layer: A preferred biocompatible layer consists, for example, of photocrosslinked tetraacrylated 18,500 Da poly(ethylene oxide) (Pathak et al., 1993, *J. Am. Chem. Soc.*, 114:8311–8312). The thickness of this layer, made by sequential photo-crosslinking of two coatings, is about 20 μm. One minute UV exposure required for the photocrosslinking process reduced the sensitivity by 16±2%.

Example 2

In vivo use of sensor

The objective of this experiment was to establish the validity of a one-point in vivo calibration. Two sensors were simultaneously implanted subcutaneously in a rat, one on the thorax, the second between the scapules. To make the difference between the blood sampled and the subcutaneous fluid proved with the sensors as extreme as possible, i.e., to probe whether the one-point calibration holds even if the organs sampled are different and the sampling sites are remote, blood was withdrawn from the tail vein. Blood glucose levels were periodically measured in withdrawn samples, while the absolute uncorrected sensor current output was continuously monitored.

In vivo experiments (6–10 hours) were carried out in 300 g male Sprague-Dawley rats. The rats were fastened overnight and prior to the experiment were anaesthetized with an intraperitoneal (i.p.) injection of sodium pentobarbital (65 mg/kg rat wt). An i.p. Injection of atropine sulfate (160 mg/kg rat wt) was then administered to suppress respiratory depression. Once the rat was anaesthetized, a portion of the rat's abdomen was shaved, coated with a conductive gel, and an Ag/AgCl surface skin reference electrode was attached. This electrode served also as the counter electrode. Sensors were then implanted subcutaneously using a 22 gauge Per-Q-Cath Introducer (Gesco International, San Antonio, Tex.) on the rat's thorax, or subcutaneously in the intrascepular area through a small surgical incision. The sensors were taped to the skin to avoid sensor movement. The sensors, along with the reference electrode, were connected to an in-house built bipotentiostat. The operating potential of the sensors was 0.3 V vs. Ag/AgCl, with the Ag/AgCl electrode serving as both the reference counter electrode. Sensor readings were collected using a data logger (Rustrak Ranger, East Greenwich, R.I.) and at the end of the experiment were transferred to a computer. During the experiment, the rat's body temperature was maintained at 37° C. by a homeostatic blanket. The sensors were allowed to reach a basal signal level for at least one hour before blood sampling was started. Blood samples were obtained from the tail vein and all blood samples were analyzed using a glucose analyzer (YSI, Inc., Yellow Springs, Ohio; Model 23A).

Approximately thirty minutes after the start of blood sampling, an i.p. glucose infusion was started using a syringe pump (Harvard Apparatus, South Natick, Mass.) at a rate of 120 mg glucose/min kg rat wt. The glucose infusion was maintained for approximately the hour.

Figure 7:
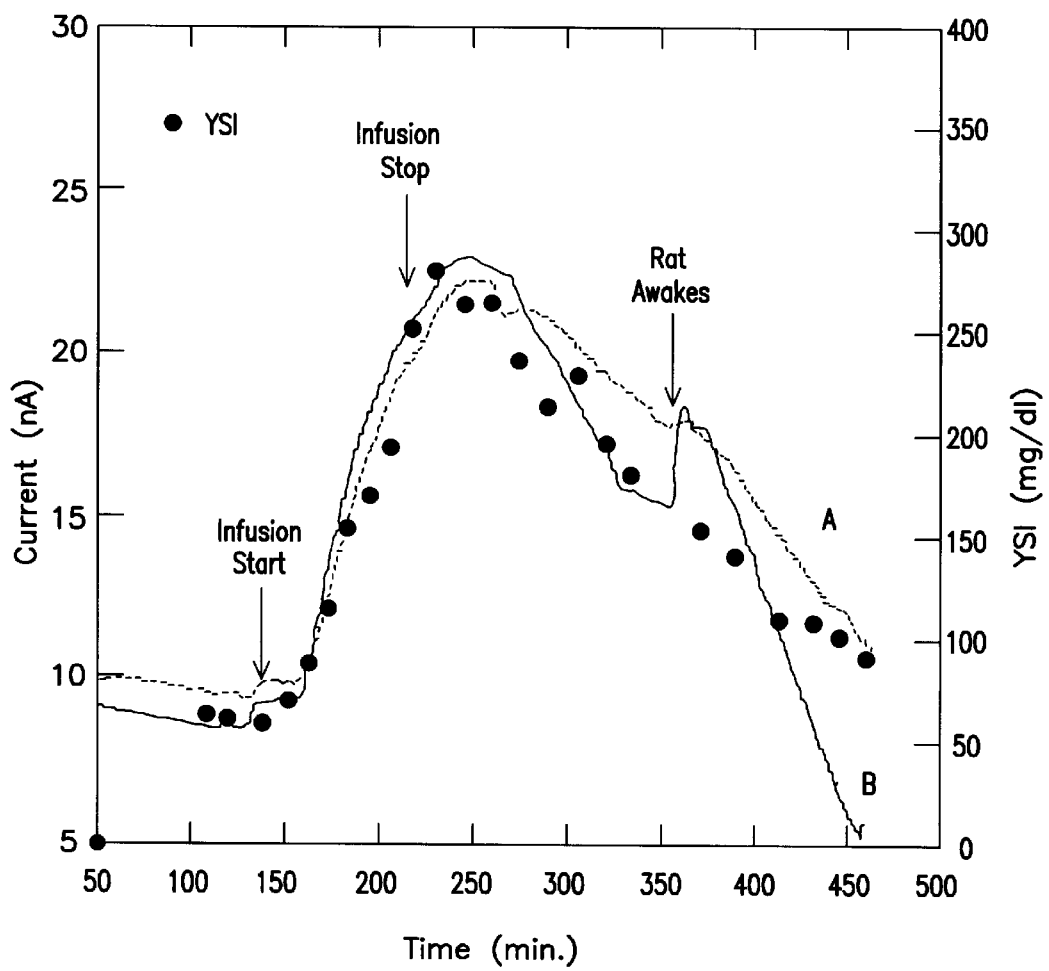
FIG. 7, is a graphical representation of data showing current density and corresponding subcutaneous glucose concentration measured with the subcutaneously implanted electrodes of the present invention in a rat animal model. Large solid circles show blood glucose concentrations measured on withdrawn blood samples using a YSI analyzer.
Figure 8:
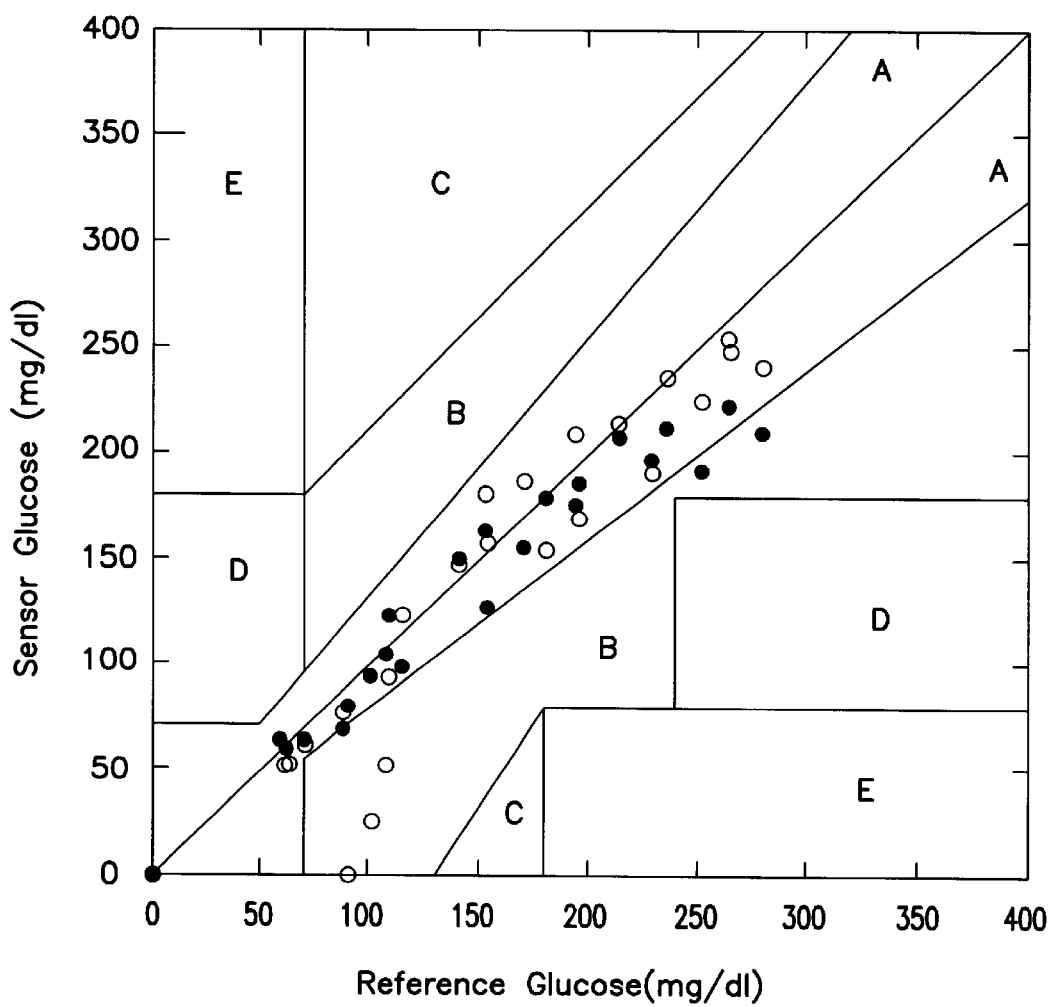
FIG. 8 is a Clarke-type clinical grid analyzing the clinical relevance of the blood glucose measurements of FIG. 7.

As seen in FIG. 7, at 410 min the current dropped prcipitously. Such a drop was observed in other measurements with subcutaneously implanted electrodes between 400 and 600 min, but was never observed in electrodes operated in buffer at 37° C. When the failed electrodes were withdrawn and retested in buffer, most of their original sensitivity was found to be intact. The cause for this apparent deactivation was failure of the counter/reference Ag/AgCl electrode on the rat's skin to make good electrolytic contact, and was not due to any failure of the implanted sensor. Using an arbitrarily chosen point to calculate a calibration curve for each electrode, i.e., one blood glucose level determination and one current measurement to establish the scales, all the data from FIG. 7 were plotted in a Clare-type, (Clarke et al., 1987, *Diabetes Care*, 5:622–627) clinical grid (FIG. 8), without further correction. In this analysis, points falling in region A of the grid are considered clinically accurate, while those in region B are considered clinically correct. Points falling in region C are not correct, but would not lead to improper treatment. Points in regions 9 and E are incorrect and if treatment would rely on these, it would be improper.

All of the points, form both electrodes, were in regions A and B, with 43 of the 48 points being in region A. The three points in region B near 100 mg/dl glucose, for the electrode implanted between the scapulses, were the last three points of the experiment, at about <10 min. Notwithstanding the failure mode at 400–600 min because of poor electrolytic contact of the counter/reference electrode with the skin and failure after 36 hours by deactivation of the lactate oxidase, resulting in loss of interference elimination, one-point calibration is shown here to be practical. After such calibration, the readings of the subcutaneous sensors provide, without any correction, clinically useful estimates of blood glucose levels.

Figure 9:
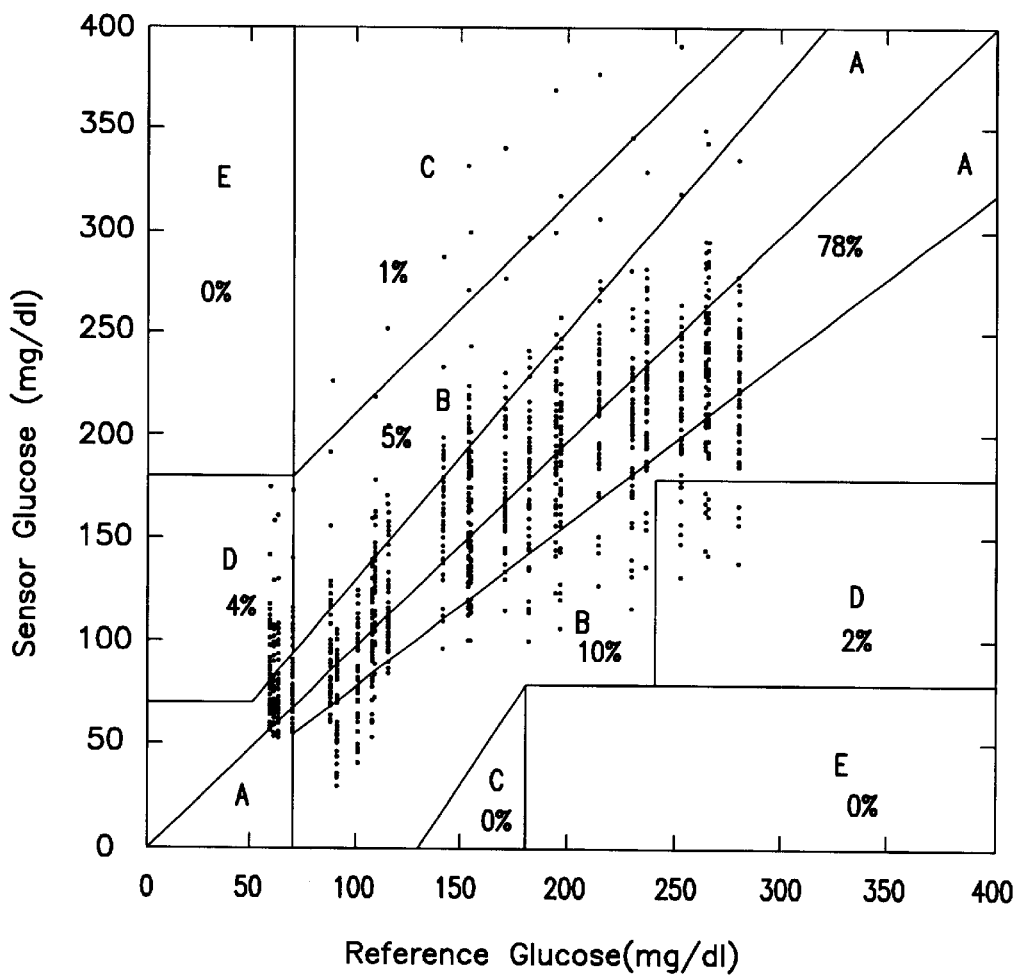
FIG. 9 is a Clarke-type clinical grid of all possible correlations obtained when each of the 24 glucose analyses of FIG. 7 were used for single point calibration of either implanted electrode.

FIG. 9 shows the distribution of all possible correlations obtained when each of the 24 glucose analyses was used for single point calibration of either implanted electrode. There are 2×24×24=1152 points in the distribution. Of these, 78% are in region A, 15% are in region B, 1% in region C, 6% are in region D, and no points are in region E.

Figure 10:
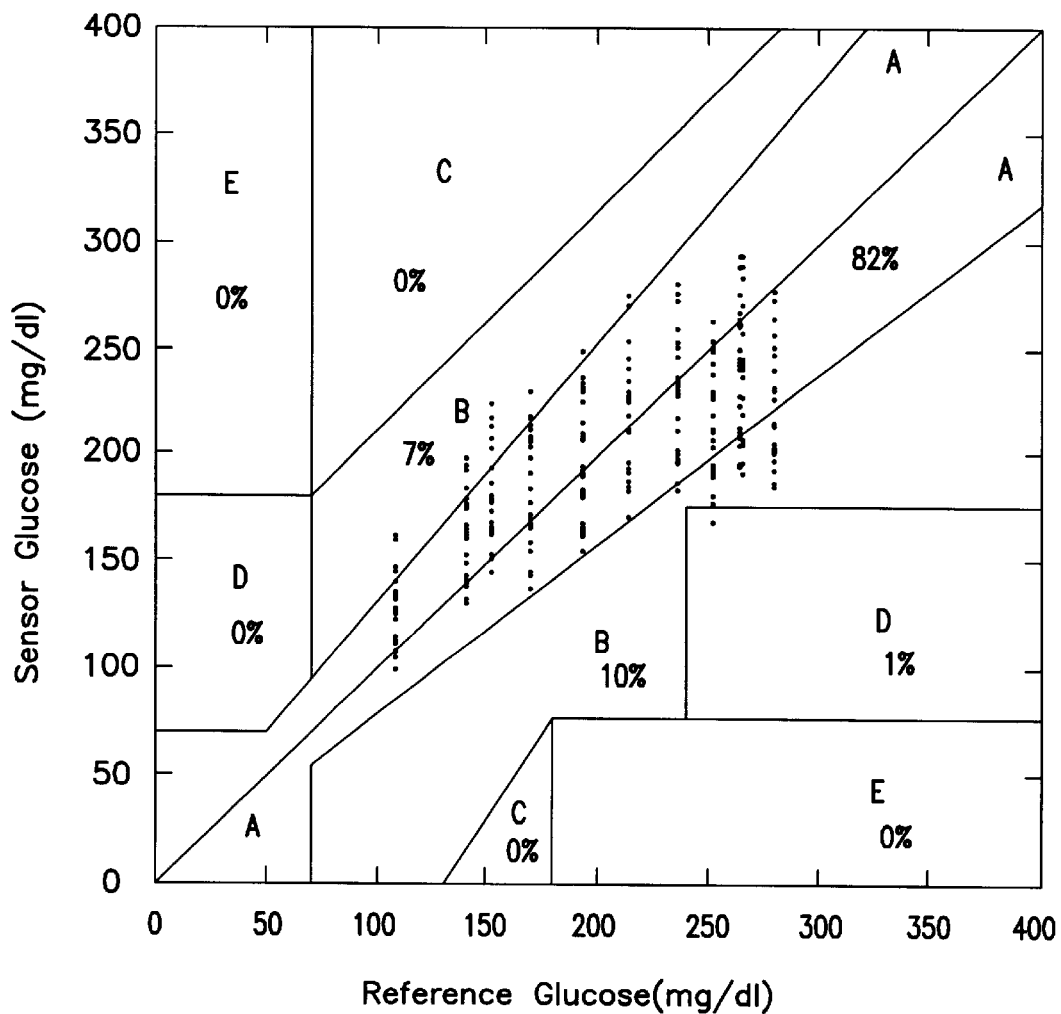
FIG. 10 is a Clarke-type clinical grid testing improvement of the single point calibration through redundant electrodes, the readings of which were within the standard deviation calculated for all differences between simultaneous readings by a pair of implanted electrodes.

In FIG. 10, we tested for the improvement of the single point calibration through using redundant electrodes. First, the readings of electrode A were normalized with respect to those of electrode B by multiplying each reading by the average output of electrode B divided by the average output of electrode A. Next the standard deviation was calculated for the differences between the 24 sets of readings of implanted electrode B and corrected readings of implanted electrode A. Then, all those sets of readings that differed by more than the standard deviation were rejected. The number of sets was reduced thereby from 24 to 11; 82% of the points were in region A, 17% in region B, 1% in region D, and no points in regions C and E. The distribution demonstrates that the sensors can be calibrated through a single independent measurement of the glucose concentration in a withdrawn blood sample. They also demonstrate the improvement in clinical accuracy resulting from the use of redundant subcutaneous sensors. The selection of those data points that differed by less than the standard deviation for the entire settled to a sixfold reduction in the probability of clinically erring in a decision based on readings of the implanted sensors.

Stability and Other Characteristics:

In order to improve the stability, more thermostable recombinant GOX, (rGOX; Heller, 1992, *J. Phys. Chem.*, 94:3579–3587) rather than GOX is used in the sensor and glucose transport is reduced to make the sensor current diffusion, not enzyme turnover, limited. The glucose flux is attenuated by the three outer layers and the sensing layer itself. Because the sensing layer contains a large excess of glucose oxidase, its activity greatly exceeds that needed for electrooxidizing the attenuated glucose flux, and the sensor's stability is improved.

The stability can be tested by methods known, for example, tested in the presence of 0.1 mM ascorbate in 10 mM glucose at 37° C. The current output of a typical optimized electrode was about 35 nA and the apparent $K_m$, derived from an Eadie-Hofstes plot, was about 20 mM (Table 1). The 10–90% response time was approximately one minute.

Figure 5:
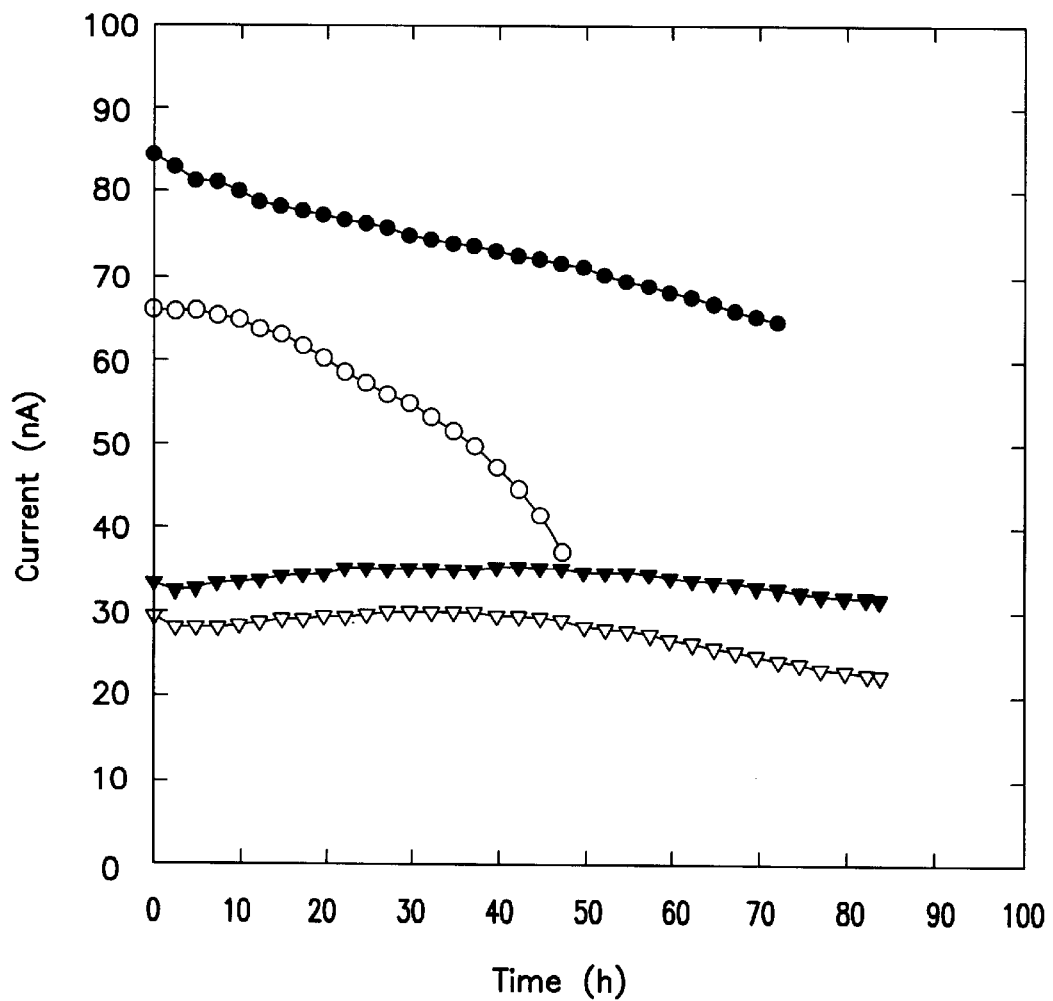
FIG. 5 is a graphical representation of data generated comparing variation of current generated by electrodes having sensing layers of differing thickness and diffusion limiting layers of different compositions and thickness. Solid circles: 7.5 $\mu$m thick sensing layer of PVI$_5$-Os (52%), rGOX (35%), PEGDGE (13%), coated with 4 $\mu$m PAL/PAZ (1:1 ratio). Open circles: 5.0 sensing layer. Solid triangles: 12.5 $\mu$m sensing layer and 7 $\mu$m PAL/PAZ (1:2 ratio). Open triangles: 7.5 $\mu$m sensing layer and 4.5 $\mu$m PAL/PAZ (1:2 ratio).

As expected, and as can be seen in FIG. 5, with thinner films the glucose mass transport was increased, i.e., the current was higher, while for thicker films the stability was improved. Because of the high sensitivity of thin sensing film (approximately 1 $\mu$m) electrodes (less than $10^{-2} A\,cm^{-2} M^{-1}$), an order of magnitude decrease in sensitivity could be treated for stability, while the currents remained high enough to be easily measured.

As seen in FIG. 5, the sensitivity of the stabilized sensors does not change by more than ±5% for 72 hours of operation at 37° C. After a small initial decrease in sensitivity, it increased to a maximum after 40 hours and the final 72 hour sensitivity was almost identical with the initial.

the characteristics of the electrodes of the present invention are summarized in Table 1. Each entry represents an average value for five tested electrodes. Baseline currents are typically less than 0.5 nA and the noise less than 10 pA. The currents observed throughout the physiological glucose concentration range (2–20 mM) exceed the noise equivalent current by at least a factor of 100. The apparent $K_m$ is 20 mM, and the 10% to 90% response time is, for aged electrodes, about 90 second at the lowest physiologically relevant glucose concentration (2 mM) and 20 seconds at the highest (20 mM).

The baseline of nil at 0 mM glucose is stable for 36 hours in the presence of 0.1 mM ascorbate. The stability observed and the existence of a valid zero-point in the presence of interferants suggest that the sensor can be used i vivo for 72 hours and tested/recalibrated in vivo through a single point calibration, i.e., by withdrawing only a single sample of blood for independent analysis.

TABLE 1

SENSOR CHARACTERISTICS

| i (nA) | j ($\mu$A/cm$^2$) | $K_M^{app}$ (mM) EH | $K_M^{app}$ (mM) LB | $t_r$ (s) | Current Variance (%) |
|---|---|---|---|---|---|
| 33.9 | 69.1 | 18.5 | 33.4 | 30-90 | 5.0 | where:
- i is the current measured at 37° C. and at 10 mM glucose concentration
- j is the current density measured at 37° C. at 10 mM glucose concentration
- $K_H^{app}$ is the apparent Michaelis-Menten coefficient determined from an electrochemical Eadie-Hoffstee (EH) or Lineweaver-Buck (LB) plot
- $t_r$ is the 10–90% risetime, 90 s for 2 mM and 30 s for 20 mH glucose concentration.
- Current Variance is the maximum deviation from the mean value, measured during the 72 hour test, conducted in 10 mM glucose in the presence of interferants. The current was continuously monitored at 37° C.

The foregoing examples are designed to illustrate certain aspects of the present invention. The examples are not intended to be comprehensive of all features and all embodiments of the present invention, and should not be construed as limiting the claims presented herein.

What is claimed is:

1. A flexible analyte sensor comprising:
    a portion of the sensor that is adapted for positioning external to the animal and for connection to a device for measurement of the electrical signal generated by the sensor;
    a portion of the sensor that is adapted for subcutaneous implantation in an animal, comprising:
        at least one non-corroding, analyte-responsive working electrode; and
        a sensing layer coupled to the working electrode;
    wherein the sensor is flexible and is adapted to provide an electrical signal that is substantially insensitive to relative motion between the implanted portion of the sensor and tissue surrounding the implanted portion of the sensor.

2. The analyte sensor of claim 1, wherein the analyte is glucose.

3. The analyte of sensor of claim 1, wherein the sensing layer comprises a non-leachable, analyte-responsive enzyme.

4. The analyte sensor of claim 3, wherein the sensing layer further comprises a hydrogel.

5. The analyte sensor of claim 3, wherein the sensing layer further comprises a non-leachable redox compound.

6. The analyte sensor of claim 1, wherein the sensor has no leachable components.

7. The analyte sensor of claim 2, further comprising a diffusion-limiting layer disposed over the sensing layer.

8. The analyte sensor of claim 7, wherein the diffusion-limiting layer is adapted to limit the rate of glucose transport to the sensing layer to be substantially lower than the rate of glucose transport to the tissue surrounding the sensor.

9. The analyte sensor of claim 7, further comprising a biocompatible layer disposed over the diffusion-limiting layer.

10. The analyte sensor of claim 9, wherein the biocompatible layer comprises poly(ethylene oxide).

11. The analyte sensor of claim 2, wherein the working electrode has a width of no more than about 0.25 mm.

12. The analyte sensor of claim 2, wherein the portion of the sensor that is adapted for subcutaneous implantation has a width of no more than about 0.29 mm.

13. The analyte sensor of claim 2, wherein the working electrode in adapted to provide a signal of current density of at least about 69 $\mu$A/cm$^2$ at 37° C. at a glucose concentration of 10 mM.

14. The analyte sensor of claim 2, wherein the sensor is adapted to have a 10 to 90% response time of not more than about 30 seconds at a glucose concentration of about 20 mM.

15. The analytic sensor of claim 2, wherein the sensor is adapted to provide a current signal deviating not more than about 5% form its average value for at least 72 hours after equilibration when glucose concentration is maintained at 10 mM.

16. The analyte sensor of claim 2, wherein the glucose response through the 2 to 20 mM glucose concentration range is close to linear.

17. The analyte sensor of claim 16, wherein the sensor has substantially no signal output when the concentration of glucose is zero.

18. A glucose measurement system comprising:
    a sensor configured to generate a signal indicative of the glucose concentration, the sensor comprising:
        a non-corroding working electrode adapted for subcutaneous implantation in an animal; and
        a sensing layer comprising a non-leachable glucose-responsive enzyme disposed on the working electrode; and a signal measuring device operatively connected to the sensor for measuring the signal generated by the sensor, the signal measuring device being configured to allow the signal generated by the sensor to reach a basal signal level for a predetermined period of time before the signal is used as an indicator of the glucose concentration.

19. The glucose measurement system of claim 18, wherein the working electrode has a width of no more than about 0.25 mm.

20. The glucose measurement system of claim 18, wherein the sensor has a width of no more than about 0.29 mm.

21. The glucose measurement system of claim 18, wherein the working electrode is adapted to provide a signal of current density of at least about 69 $\mu$A/cm$^2$ at 37° C. at a glucose concentration of 10 mM.

22. The glucose measurement system of claim 18, further comprising a diffusion-limiting layer disposed over the sensing layer.

23. The glucose measurement system of claim 18, wherein the sensor is adapted to have a 10 to 90% response time of not more than about 30 seconds at a glucose concentration of about 20 mM.

24. The glucose measurement system of claim 18, wherein the sensor is a glucose sensor and is adapted to provide a current signal deviating not more than about 5% from its average value for at least 72 hours after equilibration when glucose concentration is maintained at 10 mM.

25. An introduction system for a glucose sensor, comprising:
    an introducer adapted for subcutaneous placement of a portion of a flexible glucose sensor in an animal; and
    a portion of a flexible glucose sensor carried within the sensor introducer, the portion of a flexible glucose sensor comprising:
        a non-corroding working electrode adapted for subcutaneous implantation in an animal; and
        a sensing layer comprising a non-leachable, glucose-responsive enzyme disposed on the working electrode;
    wherein the introducer can be withdrawn from the animal while leaving the portion of a flexible glucose sensor implanted within the subcutaneous tissue of the animal.

26. The introduction system of claim 25, wherein the introducer is adapted to aid insertion of the sensor into the abdomen of the animal.

27. The introduction system of claim 25, wherein the working electrode has a width of no more than about 0.25 mm.

28. The introduction system of claim 25, wherein the portion of the flexible glucose sensor carried within the sensor introducer has a width of no more than about 0.29 mm.

29. A method of measuring the concentration of glucose in an animal tissue, the method comprising the steps of:
    (a) implanting into the animal a flexible sensor configured to generate a signal indicative of the concentration of glucose, the sensor comprising:
        a non-corroding working electrode adapted for subcutaneous implantation in an animal; and
        a sensing layer comprising a non-leachable glucose-responsive enzyme disposed on the working electrode;
    (b) connecting a signal measuring device to the sensor;
    (c) allowing the signal generated by the sensor to reach a basal signal level for a predetermined period of time; and
    (d) measuring the glucose concentration using the signal generated by the sensor after step (c).

30. A method of measuring the concentration of glucose in an animal tissue, the method comprising the steps of:
    (a) subcutaneously implanting into the animal a flexible sensor configured to generate a signal indicative of the glucose concentration, the sensor comprising:
        a non-corroding working electrode adapted for subcutaneous implantation in an animal;
        a sensing layer comprising a non-leachable glucose-responsive enzyme disposed on the working electrode; and
        a glucose diffusion-limiting layer disposed on the sensing layer;
    (b) allowing the glucose to reach the working electrode; and
    (c) limiting the rate of glucose transport to the sensing layer to a level substantially lower than the rate of glucose transport to the tissue surrounding the sensor.

31. A method for inserting a flexible glucose sensor, comprising:
    (a) providing an introducer having a width of not more than about 22 gauge adapted to subcutaneous placement of a portion of a flexible, glucose sensor in an animal;
    (b) placing within the introducer a portion of a flexible, glucose sensor, the portion of a flexible, glucose sensor comprising:
        a non-corroding working electrode adapted for subcutaneous implantation in an animal; and
        a sensing layer comprising a non-leachable, glucose-responsive enzyme disposed on the working electrode;
    (c) inserting the introducer into the animal so that the portion of the flexible, glucose sensor is carried into the subcutaneous tissue;
    (d) withdrawing the introducer from the animal while leaving the portion of a flexible glucose sensor implanted within the subcutaneous tissue of the animal; and
    (e) connecting a signal measuring device to a portion of the sensor exterior to the animal.

32. The method of claim 31, wherein the working electrode has a width of no more than about 0.25 mm.

33. The method of claim 31, wherein the portion of the flexible glucose sensor implanted within the subcutaneous tissue of the animal has a width of no more than 0.29 mm.

34. A flexible glucose sensor comprising:
    a portion of the sensor that is adapted for positioning external to the animal and for electrical contact with a device for measurement of the electrical signal generated by the sensor;
    a portion of the sensor that is adapted for subcutaneous implantation in an animal; comprising:
        at least one non-corroding, glucose-responsive working electrode; and
        a sensing layer coupled to the working electrode;
    wherein the sensor is flexible and the width of the portion of the sensor that is adapted for subcutaneous implantation is less than about 0.29 mm.

35. The flexible glucose sensor of claim 34, wherein the sensing layer comprises a non-leachable, analyte-responsive enzyme.

36. The flexible glucose sensor of claim 35, wherein the sensing layer further comprises a hydrogel.

37. The flexible glucose sensor of claim 35, wherein the sensing layer further comprises a non-leachable redox compound.

38. The flexible glucose sensor of claim 34, wherein the sensor has no leachable components.

39. The flexible glucose sensor of claim 34, further comprising a diffusion limiting layer disposed over the sensing layer.

40. The flexible glucose sensor of claim 39, wherein the diffusion-limiting layer is adapted to limit the rate of glucose transport to the sensing layer to be substantially lower than the rate of glucose transport to the tissue surrounding the sensor.

41. The flexible glucose sensor of claim 39, further comprising a biocompatible layer disposed over the diffusion-limiting layer.

42. The flexible glucose sensor of claim 39, wherein the biocompatible layer comprises poly (ethylene oxide).

43. The flexible glucose senor of claim 34, wherein the working electrode has a width of no more than about 0.25 mm.

44. The flexible glucose sensor of claim 34, wherein the working electrode is adapted to provide a signal of current density of at least about 69 $\mu$A/cm$^2$ at 37° C. at a glucose concentration of 10 mM.

45. The flexible glucose sensor of claim 34, wherein the sensor is adapted to have a 10 to 90% response time of not more than about 30 seconds at a glucose concentration of about 20 mM.

46. The flexible glucose sensor of claim 34, wherein the sensor is adapted to provide a current signal deviating not more than about 5% from its average value for at least 72 hours after equilibration when glucose concentration is maintained at 10 mM.

47. The flexible glucose sensor of claim 34, wherein the glucose response through the 2 to 20 mM glucose concentration range is close to linear.

48. The flexible glucose sensor of claim 34, wherein the sensor has substantially no signal output when the concentration of glucose is zero.

* * * * *

(12) EX PARTE REEXAMINATION CERTIFICATE (7086th)
United States Patent
Heller et al.

(10) Number: US 6,329,161 C1
(45) Certificate Issued: *Sep. 29, 2009

(54) SUBCUTANEOUS GLUCOSE ELECTRODE

(75) Inventors: Adam Heller, Austin, TX (US); Michael V. Pishko, Austin, TX (US)

(73) Assignee: Therasense, Inc., Alameda, CA (US)

Reexamination Request:
No. 90/007,914, Feb. 1, 2006
No. 90/008,713, Jul. 25, 2007

Reexamination Certificate for:
Patent No.:  6,329,161
Issued:      Dec. 11, 2001
Appl. No.:   09/668,221
Filed:       Sep. 22, 2000

(*) Notice: This patent is subject to a terminal disclaimer.

Related U.S. Application Data

(63) Continuation of application No. 09/477,053, filed on Jan. 3, 2000, now Pat. No. 6,162,611, which is a continuation of application No. 09/356,102, filed on Jul. 16, 1999, now Pat. No. 6,121,009, which is a continuation of application No. 08/767,110, filed on Dec. 4, 1996, now Pat. No. 6,284,478, which is a continuation of application No. 08/299,526, filed on Sep. 1, 1994, now Pat. No. 5,593,852, and a continuation-in-part of application No. 08/161,682, filed on Dec. 2, 1993, now Pat. No. 5,356,786.

(51) Int. Cl.
*C12Q 1/00* (2006.01)

(52) U.S. Cl. ............... 435/14; 204/403.12; 204/403.13; 435/24; 435/26; 435/28; 435/287.9; 600/347

(58) Field of Classification Search .................. None
See application file for complete search history.

(56) References Cited

U.S. PATENT DOCUMENTS

| | | |
|---|---|---|
| 2,402,306 A | 6/1946 | Turkel |
| 3,132,123 A | 5/1964 | Harris, Jr. et al. |
| 3,219,533 A | 11/1965 | Mullins |
| 3,260,656 A | 7/1966 | Ross, Jr. |
| 3,282,875 A | 11/1966 | Connolly et al. |
| 3,304,413 A | 2/1967 | Lehmann et al. |
| 3,310,606 A | 3/1967 | Fritz |
| 3,397,191 A | 8/1968 | Beckerbauer |
| 3,635,926 A | 1/1972 | Gresham et al. |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,775,182 A | 11/1973 | Patton et al. |
| 3,776,832 A | 12/1973 | Oswin et al. |
| 3,785,939 A | 1/1974 | Hsu |
| 3,837,339 A | 9/1974 | Aisenberg et al. |
| 3,851,018 A | 11/1974 | Kelly |
| 3,919,051 A | 11/1975 | Koch et al. |
| 3,926,760 A | 12/1975 | Allen et al. |
| 3,929,971 A | 12/1975 | Roy |
| 3,930,889 A | 1/1976 | Ruggiero et al. |
| 3,933,593 A | 1/1976 | Sternberg |
| 3,943,918 A | 3/1976 | Lewis |
| 3,964,974 A | 6/1976 | Banauch et al. |

(Continued)

FOREIGN PATENT DOCUMENTS

| | | |
|---|---|---|
| DE | 4401400 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0 098 592 | 1/1984 |
| EP | 0098592 | 1/1984 |
| EP | 0107634 | 5/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |

(Continued)

OTHER PUBLICATIONS

M. Sakakida et al., "Ferrocene–mediated Needle–type Glucose Sensor Covered with Newly Designed Biocompatible Membrane", Sensors and Actuators B, vol. 13–14, pp. 319–322 (May/Jun. 1993).*
M.Schichiri et al., "Needle–type Glucose Sensor for Wearable Artificial Endocrine Pancreas", Chap. 15 in Implantable Sensors for Closed–Loop Prosthetic Systems (W.H. Ko. Ed., Futura Publishing Co. Mount Kisco, NY 1985).*
G. S. Wilson et al., "Progress Toward the Development of an Implantable Glucose Sensor Clinical Chemistry", vol. 38(9) pp. 1613–1617 (1992).*
Schichiri et al., "Membrane Design for Extending the Long Life of an Implantable Glucose Sensor", Diab. Nutr. Metab., vol. 2(4) pp. 309–313 (1989).*
Abstract from Korf, J. et al., "Monitoring of Glucose and Lactate Using Microdialysis: Applications in Neonates and Rat Brain", Developmental Neuroscience, vol. 15, No. 3–5, pp. 240–246 (1993).

(Continued)

*Primary Examiner*—Gary L Kunz

(57) ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

U.S. PATENT DOCUMENTS

| | | |
|---|---|---|
| 3,966,580 A | 6/1976 | Janata et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,032,729 A | 6/1977 | Koistinen |
| 4,040,908 A | 8/1977 | Clark, Jr. |
| 4,055,175 A | 10/1977 | Clemens et al. |
| 4,059,406 A | 11/1977 | Fleet |
| 4,059,708 A | 11/1977 | Heiss, Jr. et al. |
| 4,068,536 A | 1/1978 | Stackhouse |
| 4,073,713 A | 2/1978 | Newman |
| 4,076,596 A | 2/1978 | Connery et al. |
| 4,076,656 A | 2/1978 | White et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danninger et al. |
| 4,172,770 A | 10/1979 | Semersky et al. |
| 4,178,916 A | 12/1979 | McNamara |
| 4,193,982 A | 3/1980 | Avrameas et al. |
| 4,197,840 A | 4/1980 | Beck et al. |
| 4,206,755 A | 6/1980 | Klein |
| 4,215,703 A | 8/1980 | Wilson |
| 4,224,125 A | 9/1980 | Nakamura et al. |
| 4,240,438 A | 12/1980 | Updike et al. |
| 4,240,889 A | 12/1980 | Yoda et al. |
| 4,241,438 A | 12/1980 | Kern |
| 4,245,634 A | 1/1981 | Albisser et al. |
| 4,247,297 A | 1/1981 | Berti et al. |
| 4,255,500 A | 3/1981 | Hooke |
| 4,259,540 A | 3/1981 | Sabia |
| 4,271,449 A | 6/1981 | Grogan |
| 4,275,225 A | 6/1981 | Krespan |
| 4,318,784 A | 3/1982 | Higgins et al. |
| 4,324,257 A | 4/1982 | Albarda et al. |
| 4,327,725 A | 5/1982 | Cortese et al. |
| 4,331,869 A | 5/1982 | Rollo |
| 4,335,255 A | 6/1982 | Krespan |
| 4,340,458 A | 7/1982 | Lerner et al. |
| 4,344,438 A | 8/1982 | Schultz |
| 4,352,960 A | 10/1982 | Dormer et al. |
| 4,353,888 A | 10/1982 | Sefton |
| 4,356,074 A | 10/1982 | Johnson |
| 4,357,282 A | 11/1982 | Anderson et al. |
| 4,365,637 A | 12/1982 | Johnson |
| 4,366,033 A | 12/1982 | Richter et al. |
| 4,374,013 A | 2/1983 | Enfors |
| 4,375,399 A | 3/1983 | Havas et al. |
| 4,384,586 A | 5/1983 | Christiansen |
| 4,388,166 A | 6/1983 | Suzuki et al. |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,288 A | 10/1983 | Langer et al. |
| 4,407,959 A | 10/1983 | Tsuji et al. |
| 4,415,666 A | 11/1983 | D'Orazio et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller |
| 4,427,770 A | 1/1984 | Chen et al. |
| 4,431,004 A | 2/1984 | Bessman et al. |
| 4,431,507 A | 2/1984 | Nankai et al. |
| 4,436,094 A | 3/1984 | Cerami |
| 4,440,175 A | 4/1984 | Wilkins |
| 4,443,218 A | 4/1984 | DeCant, Jr. et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,476,003 A | 10/1984 | Frank et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,499,249 A | 2/1985 | Nakagawa et al. |
| 4,506,680 A | 3/1985 | Stokes |
| 4,512,348 A | 4/1985 | Uchigaki et al. |
| 4,522,690 A | 6/1985 | Venkatasetty |
| 4,524,114 A | 6/1985 | Samuels et al. |
| 4,526,661 A | 7/1985 | Steckhan et al. |
| 4,526,948 A | 7/1985 | Resnick |
| 4,527,240 A | 7/1985 | Kvitash |
| 4,530,696 A | 7/1985 | Bisera et al. |
| 4,534,356 A | 8/1985 | Papadakis |
| 4,538,616 A | 9/1985 | Rogoff et al. |
| 4,543,955 A | 10/1985 | Schroeppel |
| 4,544,869 A | 10/1985 | Pittaway |
| 4,545,382 A | 10/1985 | Higgins et al. |
| 4,552,840 A | 11/1985 | Riffer |
| 4,560,534 A | 12/1985 | Kung et al. |
| 4,561,443 A | 12/1985 | Hogrefe et al. |
| 4,569,589 A | 2/1986 | Neufeld |
| 4,571,292 A | 2/1986 | Liu et al. |
| 4,573,994 A | 3/1986 | Fischell et al. |
| 4,577,642 A | 3/1986 | Stokes |
| 4,581,336 A | 4/1986 | Malloy et al. |
| 4,595,011 A | 6/1986 | Phillips |
| 4,595,479 A | 6/1986 | Kimura et al. |
| 4,614,760 A | 9/1986 | Homan et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| RE32,361 E | 2/1987 | Duggan |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,663,824 A | 5/1987 | Kenmochi |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,681,111 A | 7/1987 | Silvian |
| 4,682,602 A | 7/1987 | Prohaska |
| 4,684,537 A | 8/1987 | Graetzel et al. |
| 4,685,463 A | 8/1987 | Williams |
| 4,686,624 A | 8/1987 | Blum et al. |
| 4,698,582 A | 10/1987 | Braun et al. |
| 4,703,756 A | 11/1987 | Gough et al. |
| 4,711,245 A | 12/1987 | Higgins et al. |
| 4,711,251 A | 12/1987 | Stokes |
| 4,714,462 A | 12/1987 | DiDomenico |
| 4,717,673 A | 1/1988 | Wrighton et al. |
| 4,718,893 A | 1/1988 | Dorman |

| | | | | | | |
|---|---|---|---|---|---|---|
| 4,721,601 A | 1/1988 | Wrighton et al. | | 4,927,407 A | 5/1990 | Dorman |
| 4,721,677 A | 1/1988 | Clark, Jr. | | 4,927,516 A | 5/1990 | Yamaguchi et al. |
| 4,726,378 A | 2/1988 | Kaplan | | 4,931,795 A | 6/1990 | Gord |
| 4,726,716 A | 2/1988 | McGuire | | 4,934,369 A | 6/1990 | Maxwell |
| 4,731,051 A | 3/1988 | Fischell | | 4,935,105 A | 6/1990 | Churchouse |
| 4,731,726 A | 3/1988 | Allen, III | | 4,935,345 A | 6/1990 | Guilbeau et al. |
| 4,747,828 A | 5/1988 | Tseo | | 4,936,956 A | 6/1990 | Wrighton |
| 4,749,985 A | 6/1988 | Corsberg | | 4,938,860 A | 7/1990 | Wogoman |
| 4,750,496 A | 6/1988 | Reinhart | | 4,942,127 A | 7/1990 | Wada et al. |
| 4,753,652 A | 6/1988 | Langer et al. | | 4,944,299 A | 7/1990 | Silvian |
| 4,757,022 A | 7/1988 | Shults et al. | | 4,945,045 A | 7/1990 | Forrest et al. |
| 4,758,323 A | 7/1988 | Davis et al. | | 4,950,378 A | 8/1990 | Nagata |
| 4,759,371 A | 7/1988 | Franetzki | | 4,953,552 A | 9/1990 | DeMarzo |
| 4,759,828 A | 7/1988 | Young et al. | | 4,954,129 A | 9/1990 | Giuliani et al. |
| 4,764,416 A | 8/1988 | Ueyama et al. | | 4,955,861 A | 9/1990 | Enegren et al. |
| 4,776,944 A | 10/1988 | Janata et al. | | 4,957,115 A | 9/1990 | Selker |
| 4,777,953 A | 10/1988 | Ash et al. | | 4,958,632 A | 9/1990 | Duggan |
| 4,779,618 A | 10/1988 | Mund et al. | | 4,963,595 A | 10/1990 | Ward et al. |
| 4,781,798 A | 11/1988 | Gough | | 4,968,400 A | 11/1990 | Shimomura et al. |
| 4,784,736 A | 11/1988 | Lonsdale et al. | | 4,969,468 A | 11/1990 | Byers et al. |
| 4,787,398 A | 11/1988 | Garcia et al. | | 4,970,145 A | 11/1990 | Bennetto et al. |
| 4,795,707 A | 1/1989 | Niiyama et al. | | 4,974,929 A | 12/1990 | Curry |
| 4,796,634 A | 1/1989 | Huntsman et al. | | 4,979,509 A | 12/1990 | Hakky |
| 4,803,243 A | 2/1989 | Fujimoto et al. | | 4,984,929 A | 1/1991 | Rock et al. |
| 4,803,625 A | 2/1989 | Fu et al. | | 4,986,271 A * | 1/1991 | Wilkins ..................... 600/347 |
| 4,803,726 A | 2/1989 | Levine et al. | | 4,986,671 A | 1/1991 | Sun et al. |
| 4,805,624 A | 2/1989 | Yao et al. | | 4,990,845 A | 2/1991 | Gord |
| 4,810,470 A | 3/1989 | Burkhardt et al. | | 4,991,582 A | 2/1991 | Byers et al. |
| 4,813,424 A | 3/1989 | Wilkins | | 4,994,068 A | 2/1991 | Hufnagie |
| 4,815,469 A | 3/1989 | Cohen et al. | | 4,994,167 A | 2/1991 | Shults et al. |
| 4,820,399 A | 4/1989 | Senda et al. | | 4,995,402 A | 2/1991 | Smith et al. |
| 4,822,337 A | 4/1989 | Newhouse et al. | | 5,001,054 A | 3/1991 | Wagner |
| 4,830,959 A | 5/1989 | McNeil et al. | | 5,002,054 A | 3/1991 | Ash et al. |
| 4,832,797 A | 5/1989 | Vadgama et al. | | 5,002,572 A | 3/1991 | Picha |
| 4,835,372 A | 5/1989 | Gombrich et al. | | 5,007,427 A | 4/1991 | Suzuki et al. |
| RE32,947 E | 6/1989 | Dormer et al. | | 5,007,929 A | 4/1991 | Quaid |
| 4,837,049 A | 6/1989 | Byers et al. | | 5,016,172 A | 5/1991 | Dessertine |
| 4,838,887 A | 6/1989 | Idriss | | 5,016,201 A | 5/1991 | Bryan et al. |
| 4,840,893 A | 6/1989 | Hill et al. | | 5,016,631 A | 5/1991 | Hogrefe et al. |
| RE32,974 E | 7/1989 | Porat et al. | | 5,019,974 A | 5/1991 | Beckers |
| 4,844,076 A | 7/1989 | Lesho et al. | | 5,030,333 A | 7/1991 | Clark, Jr. |
| 4,845,035 A | 7/1989 | Fanta et al. | | 5,034,112 A | 7/1991 | Murase et al. |
| 4,848,351 A | 7/1989 | Finch | | 5,034,192 A | 7/1991 | Wrighton et al. |
| 4,849,458 A | 7/1989 | Reed et al. | | 5,035,860 A | 7/1991 | Kleingeld et al. |
| 4,854,322 A | 8/1989 | Ash et al. | | 5,036,860 A | 8/1991 | Leigh et al. |
| 4,856,340 A | 8/1989 | Garrison | | 5,036,861 A | 8/1991 | Sembrowich et al. |
| 4,857,713 A | 8/1989 | Brown | | 5,037,527 A | 8/1991 | Hayashi et al. |
| 4,858,617 A | 8/1989 | Sanders | | 5,049,487 A | 9/1991 | Phillips et al. |
| 4,870,561 A | 9/1989 | Love et al. | | 5,050,612 A | 9/1991 | Matsumura |
| 4,871,351 A | 10/1989 | Feingold | | 5,055,171 A | 10/1991 | Peck |
| 4,871,440 A | 10/1989 | Nagata et al. | | 5,058,592 A | 10/1991 | Whisler |
| 4,874,499 A | 10/1989 | Smith et al. | | 5,059,654 A | 10/1991 | Hou et al. |
| 4,874,500 A | 10/1989 | Madou et al. | | 5,063,081 A | 11/1991 | Cozzette et al. |
| 4,889,744 A | 12/1989 | Quaid | | 5,067,491 A | 11/1991 | Taylor et al. |
| 4,890,620 A | 1/1990 | Gough | | 5,068,536 A | 11/1991 | Rosenthal |
| 4,890,621 A | 1/1990 | Hakky | | 5,070,535 A | 12/1991 | Hochmair et al. |
| 4,894,137 A | 1/1990 | Takizawa et al. | | 5,073,500 A | 12/1991 | Saito et al. |
| 4,896,142 A | 1/1990 | Aycox et al. | | 5,074,977 A | 12/1991 | Cheung et al. |
| 4,897,162 A | 1/1990 | Lewandowski et al. | | 5,077,476 A | 12/1991 | Rosenthal |
| 4,897,173 A | 1/1990 | Nankai et al. | | 5,078,854 A | 1/1992 | Burgess et al. |
| 4,897,457 A | 1/1990 | Nakamura et al. | | 5,082,550 A | 1/1992 | Rishpon et al. |
| 4,899,839 A | 2/1990 | Dessertine et al. | | 5,082,786 A | 1/1992 | Nakamoto |
| 4,909,908 A | 3/1990 | Ross et al. | | 5,084,828 A | 1/1992 | Kaufman et al. |
| 4,911,794 A | 3/1990 | Parce et al. | | 5,088,981 A | 2/1992 | Howson et al. |
| 4,917,800 A | 4/1990 | Lonsdale et al. | | 5,089,112 A | 2/1992 | Skotheim et al. |
| 4,919,141 A | 4/1990 | Zier et al. | | 5,094,951 A | 3/1992 | Rosenberg |
| 4,919,767 A | 4/1990 | Vadgama et al. | | 5,095,904 A | 3/1992 | Seligman et al. |
| 4,920,969 A | 5/1990 | Suzuki et al. | | 5,096,560 A | 3/1992 | Takai et al. |
| 4,920,977 A | 5/1990 | Haynes | | 5,096,836 A | 3/1992 | Macho et al. |
| 4,923,586 A | 5/1990 | Katayama et al. | | 5,097,834 A | 3/1992 | Skrabal |
| 4,925,268 A | 5/1990 | Iyer et al. | | 5,101,814 A | 4/1992 | Palti |

| Patent No. | Date | Inventor |
|---|---|---|
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,114,678 A | 5/1992 | Crawford et al. |
| 5,120,420 A | 6/1992 | Nankai et al. |
| 5,120,421 A | 6/1992 | Glass et al. |
| 5,126,034 A | 6/1992 | Carter et al. |
| 5,126,247 A | 6/1992 | Palmer et al. |
| 5,130,009 A | 7/1992 | Marsoner et al. |
| 5,131,441 A | 7/1992 | Simpson et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,140,985 A | 8/1992 | Schroeder et al. |
| 5,141,868 A | 8/1992 | Shanks et al. |
| 5,147,725 A | 9/1992 | Pinchuk |
| 5,153,827 A | 10/1992 | Coutre et al. |
| 5,161,532 A | 11/1992 | Joseph |
| 5,165,407 A * | 11/1992 | Wilson et al. ............. 600/345 |
| 5,168,046 A | 12/1992 | Hamamoto et al. |
| 5,171,689 A | 12/1992 | Kawaguri et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,198,771 A | 3/1993 | Fidler et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,232,668 A | 8/1993 | Grant et al. |
| 5,235,003 A | 8/1993 | Ward et al. |
| 5,242,848 A | 9/1993 | Yeh |
| 5,243,983 A | 9/1993 | Tarr et al. |
| 5,246,867 A | 9/1993 | Lakowicz et al. |
| 5,249,576 A | 10/1993 | Goldberger et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,259,769 A | 11/1993 | Cruise et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,736 A | 12/1993 | Picha |
| 5,271,815 A | 12/1993 | Wong |
| 5,272,060 A | 12/1993 | Hamamoto et al. |
| 5,275,159 A | 1/1994 | Griebel |
| 5,276,610 A | 1/1994 | Maeda et al. |
| 5,278,079 A | 1/1994 | Gubinski et al. |
| 5,279,294 A | 1/1994 | Anderson |
| 5,282,848 A | 2/1994 | Schmitt |
| 5,282,950 A | 2/1994 | Dietze et al. |
| 5,284,156 A | 2/1994 | Schramm et al. |
| 5,284,570 A | 2/1994 | Savage et al. |
| 5,284,748 A | 2/1994 | Mroczkowski et al. |
| 5,285,513 A | 2/1994 | Kaufman et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,299,571 A | 4/1994 | Mastrototaro |
| 5,304,127 A | 4/1994 | Kawahara et al. |
| 5,304,468 A | 4/1994 | Phillips et al. |
| 5,307,263 A | 4/1994 | Brown |
| 5,309,919 A | 5/1994 | Snell et al. |
| 5,310,469 A | 5/1994 | Cunningham et al. |
| 5,310,885 A | 5/1994 | Maier et al. |
| 5,312,361 A | 5/1994 | Zadini et al. |
| 5,314,450 A | 5/1994 | Thompson |
| 5,314,471 A | 5/1994 | Brauker et al. |
| 5,318,521 A | 6/1994 | Slettenmark |
| 5,320,098 A | 6/1994 | Davidson |
| 5,320,725 A | 6/1994 | Gregg et al. |
| 5,322,063 A * | 6/1994 | Allen et al. ............. 600/347 |
| 5,324,303 A | 6/1994 | Strong et al. |
| 5,324,316 A | 6/1994 | Schulman et al. |
| 5,326,356 A | 7/1994 | Della Valle et al. |
| 5,326,449 A | 7/1994 | Cunningham |
| 5,328,460 A | 7/1994 | Lord et al. |
| 5,330,521 A | 7/1994 | Cohen |
| 5,330,634 A | 7/1994 | Wong et al. |
| 5,331,966 A | 7/1994 | Bennett et al. |
| 5,337,258 A | 8/1994 | Dennis |
| 5,337,747 A | 8/1994 | Nefte |
| 5,340,722 A | 8/1994 | Wolfbeis et al. |
| 5,342,409 A | 8/1994 | Mulleti |
| 5,342,789 A | 8/1994 | Chick et al. |
| 5,343,869 A | 9/1994 | Pross et al. |
| 5,344,454 A | 9/1994 | Clarke et al. |
| 5,348,788 A | 9/1994 | White |
| 5,350,407 A | 9/1994 | McClure et al. |
| 5,352,348 A | 10/1994 | Young et al. |
| 5,352,351 A | 10/1994 | White |
| 5,354,319 A | 10/1994 | Wyborny et al. |
| 5,356,348 A | 10/1994 | Bellio et al. |
| 5,356,786 A | 10/1994 | Heller et al. |
| 5,358,514 A | 10/1994 | Schulman et al. |
| 5,364,797 A | 11/1994 | Olson et al. |
| 5,366,609 A | 11/1994 | White et al. |
| 5,368,028 A | 11/1994 | Palti |
| 5,368,562 A | 11/1994 | Blomquist et al. |
| 5,370,622 A | 12/1994 | Livingston et al. |
| 5,371,687 A | 12/1994 | Holmes, II et al. |
| 5,372,133 A | 12/1994 | Hogen Esch |
| 5,372,719 A | 12/1994 | Afeyan et al. |
| 5,373,336 A | 12/1994 | Sugita |
| 5,375,604 A | 12/1994 | Kelly et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |

| | | | | | |
|---|---|---|---|---|---|
| 5,380,422 A | 1/1995 | Negishis et al. | 5,538,511 A | 7/1996 | Van Antwerp et al. |
| 5,380,536 A | 1/1995 | Hubbell et al. | 5,540,828 A | 7/1996 | Yacynych |
| 5,382,346 A | 1/1995 | Uenoyama et al. | 5,545,152 A | 8/1996 | Funderburk et al. |
| 5,384,028 A | 1/1995 | Ito | 5,545,191 A | 8/1996 | Mann et al. |
| 5,387,327 A | 2/1995 | Khan | 5,545,220 A | 8/1996 | Andrews et al. |
| 5,390,671 A | 2/1995 | Lord et al. | 5,545,223 A | 8/1996 | Neuenfeldt et al. |
| 5,391,250 A | 2/1995 | Cheney, II et al. | 5,549,113 A | 8/1996 | Halleck et al. |
| 5,393,903 A | 2/1995 | Gratzel et al. | 5,549,115 A | 8/1996 | Morgan et al. |
| 5,395,504 A | 3/1995 | Saurer et al. | 5,549,675 A | 8/1996 | Neuenfeldt et al. |
| 5,397,848 A | 3/1995 | Yang et al. | 5,552,027 A | 9/1996 | Birkle et al. |
| 5,399,823 A | 3/1995 | McCusker | 5,554,166 A | 9/1996 | Lange et al. |
| 5,400,782 A | 3/1995 | Beaubiah | 5,556,524 A | 9/1996 | Albers |
| 5,408,999 A | 4/1995 | Singh et al. | 5,560,357 A | 10/1996 | Faupei et al. |
| 5,410,471 A | 4/1995 | Alyfuku et al. | 5,562,713 A | 10/1996 | Silvian |
| 5,410,474 A | 4/1995 | Fox | 5,564,439 A | 10/1996 | Picha |
| 5,411,536 A | 5/1995 | Armstrong | 5,565,085 A | 10/1996 | Ikeda et al. |
| 5,411,647 A * | 5/1995 | Johnson et al. .......... 205/777.5 | 5,567,302 A | 10/1996 | Song et al. |
| 5,413,690 A | 5/1995 | Kost et al. | 5,568,806 A | 10/1996 | Cheney et al. |
| 5,422,246 A | 6/1995 | Koopal et al. | 5,569,186 A | 10/1996 | Lord et al. |
| 5,426,032 A | 6/1995 | Phillips et al. | 5,569,212 A | 10/1996 | Brown |
| 5,429,129 A | 7/1995 | Lovejoy et al. | 5,569,462 A | 10/1996 | Martinson et al. |
| 5,431,691 A | 7/1995 | Snell et al. | 5,571,395 A | 11/1996 | Park et al. |
| 5,431,921 A | 7/1995 | Thombre | 5,573,506 A | 11/1996 | Vasko |
| 5,433,710 A | 7/1995 | Van Antwerp et al. | 5,573,647 A | 11/1996 | Maley et al. |
| 5,437,973 A | 8/1995 | Vadgama et al. | 5,575,895 A | 11/1996 | Ikeda et al. |
| 5,437,999 A | 8/1995 | Dieboid et al. | 5,575,930 A | 11/1996 | Tietje-Girault et al. |
| 5,438,984 A | 8/1995 | Schoendorfer | 5,580,527 A | 12/1996 | Bell et al. |
| 5,445,611 A | 8/1995 | Eppstein et al. | 5,580,794 A | 12/1996 | Allen |
| 5,445,920 A | 8/1995 | Saito | 5,582,184 A | 12/1996 | Erickson et al. |
| 5,451,260 A | 9/1995 | Versteeg et al. | 5,582,593 A | 12/1996 | Hultman |
| 5,452,173 A | 9/1995 | Brannon et al. | 5,582,697 A | 12/1996 | Ikeda et al. |
| 5,453,199 A | 9/1995 | Afejan et al. | 5,582,698 A | 12/1996 | Flaherty et al. |
| 5,453,278 A | 9/1995 | Chan et al. | 5,584,813 A | 12/1996 | Livingston et al. |
| 5,456,692 A | 10/1995 | Smith, Jr. et al. | 5,584,876 A | 12/1996 | Bruchman et al. |
| 5,456,940 A | 10/1995 | Funderburk | 5,586,553 A | 12/1996 | Halili et al. |
| 5,458,140 A | 10/1995 | Eppstein et al. | 5,587,273 A | 12/1996 | Yan et al. |
| 5,460,618 A | 10/1995 | Harreld | 5,589,326 A | 12/1996 | Deng et al. |
| 5,462,051 A | 10/1995 | Oka et al. | 5,589,563 A | 12/1996 | Ward et al. |
| 5,462,064 A | 10/1995 | D'Angelo et al. | 5,590,651 A | 1/1997 | Shaffer et al. |
| 5,462,525 A | 10/1995 | Srisathapat et al. | 5,593,440 A | 1/1997 | Brauker et al. |
| 5,462,645 A | 10/1995 | Albery et al. | 5,593,852 A | 1/1997 | Heller et al. |
| 5,466,218 A | 11/1995 | Srisathapat et al. | 5,594,906 A | 1/1997 | Holmes, II et al. |
| 5,469,846 A | 11/1995 | Khan | 5,596,150 A | 1/1997 | Arndy et al. |
| 5,472,317 A | 12/1995 | Field et al. | 5,596,994 A | 1/1997 | Bro |
| 5,476,460 A | 12/1995 | Montalvo | 5,601,435 A | 2/1997 | Quy |
| 5,477,855 A | 12/1995 | Schindler et al. | 5,601,694 A | 2/1997 | Maley et al. |
| 5,482,473 A | 1/1996 | Lord et al. | 5,605,152 A | 2/1997 | Slate et al. |
| 5,484,404 A | 1/1996 | Schulman et al. | 5,607,565 A | 3/1997 | Azarnia et al. |
| 5,487,751 A | 1/1996 | Radons et al. | 5,611,900 A | 3/1997 | Worden et al. |
| 5,491,474 A | 2/1996 | Suni et al. | 5,615,671 A | 4/1997 | Schoonen et al. |
| 5,494,562 A | 2/1996 | Maley et al. | 5,616,222 A | 4/1997 | Maley et al. |
| 5,496,453 A | 3/1996 | Uenoyama et al. | 5,617,851 A | 4/1997 | Lipkovker |
| 5,497,772 A | 3/1996 | Schulman et al. | 5,623,925 A | 4/1997 | Swenson et al. |
| 5,501,665 A | 3/1996 | Jhuboo et al. | 5,624,537 A | 4/1997 | Turner et al. |
| 5,501,956 A | 3/1996 | Wada et al. | 5,628,309 A | 5/1997 | Brown |
| 5,505,709 A | 4/1996 | Funderburk | 5,628,310 A | 5/1997 | Rao et al. |
| 5,505,713 A | 4/1996 | Van Antwerp et al. | 5,628,890 A | 5/1997 | Carter et al. |
| 5,507,288 A | 4/1996 | Bocker et al. | 5,629,981 A | 5/1997 | Nerlikar |
| 5,508,171 A | 4/1996 | Walling et al. | 5,637,095 A | 6/1997 | Nason et al. |
| 5,509,410 A | 4/1996 | Hill et al. | 5,640,764 A | 6/1997 | Strojnik |
| 5,514,103 A | 5/1996 | Srisathapat et al. | 5,640,954 A | 6/1997 | Pfeiffer et al. |
| 5,514,253 A | 5/1996 | Davis et al. | 5,643,212 A | 7/1997 | Coutre et al. |
| 5,518,006 A | 5/1996 | Mawhirt et al. | 5,647,853 A | 7/1997 | Feldmann et al. |
| 5,520,787 A | 5/1996 | Hanagan et al. | 5,650,062 A | 7/1997 | Ikeda et al. |
| 5,522,865 A | 6/1996 | Schulman et al. | 5,651,767 A | 7/1997 | Schulman et al. |
| 5,525,511 A | 6/1996 | D'Costa | 5,651,869 A | 7/1997 | Yoshioka et al. |
| 5,526,120 A | 6/1996 | Jina et al. | 5,653,735 A | 8/1997 | Chen et al. |
| 5,527,307 A | 6/1996 | Srisathapat et al. | 5,653,756 A | 8/1997 | Clarke et al. |
| 5,529,676 A | 6/1996 | Maley et al. | 5,653,863 A | 8/1997 | Genshaw et al. |
| 5,531,878 A | 7/1996 | Vadgama et al. | 5,658,250 A | 8/1997 | Blomquist et al. |
| 5,538,007 A | 7/1996 | Gorman | 5,658,330 A | 8/1997 | Carlisle et al. |

| Patent | Date | Inventor |
|---|---|---|
| 5,660,163 A | 8/1997 | Schulman et al. |
| 5,662,694 A | 9/1997 | Lidman et al. |
| 5,665,065 A | 9/1997 | Colman et al. |
| 5,667,983 A | 9/1997 | Abel et al. |
| 5,670,031 A | 9/1997 | Hintsche et al. |
| 5,678,571 A | 10/1997 | Brown |
| 5,679,690 A | 10/1997 | Andre et al. |
| 5,680,858 A | 10/1997 | Hansen et al. |
| 5,682,233 A | 10/1997 | Brinda |
| 5,686,717 A | 11/1997 | Knowles et al. |
| 5,686,829 A | 11/1997 | Girault |
| 5,695,473 A | 12/1997 | Olsen |
| 5,695,623 A | 12/1997 | Michel et al. |
| 5,695,949 A | 12/1997 | Galen et al. |
| 5,701,894 A | 12/1997 | Cherry et al. |
| 5,704,354 A | 1/1998 | Preidel et al. |
| 5,704,922 A | 1/1998 | Brown |
| 5,706,807 A | 1/1998 | Picha |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,711,868 A | 1/1998 | Maley et al. |
| 5,713,888 A | 2/1998 | Neuenfeldt et al. |
| 5,714,123 A | 2/1998 | Sohrab |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,727,548 A | 3/1998 | Hill et al. |
| 5,730,124 A | 3/1998 | Yamauchi |
| 5,730,654 A | 3/1998 | Brown |
| 5,735,273 A | 4/1998 | Kurnik et al. |
| 5,735,285 A | 4/1998 | Albert et al. |
| 5,741,211 A | 4/1998 | Renirie et al. |
| 5,741,330 A | 4/1998 | Brauker et al. |
| 5,741,688 A | 4/1998 | Oxenboll et al. |
| 5,743,262 A | 4/1998 | Lepper, Jr. et al. |
| 5,746,217 A | 5/1998 | Erickson et al. |
| 5,748,103 A | 5/1998 | Flach et al. |
| 5,749,907 A | 5/1998 | Mann |
| 5,750,926 A | 5/1998 | Schulman et al. |
| 5,756,632 A | 5/1998 | Ward et al. |
| 5,770,028 A | 6/1998 | Maley et al. |
| 5,771,001 A | 6/1998 | Cobb |
| 5,771,890 A | 6/1998 | Tamada |
| 5,772,586 A | 6/1998 | Heinonen et al. |
| 5,777,060 A | 7/1998 | Van Antwerp |
| 5,779,665 A | 7/1998 | Mastrototaro et al. |
| 5,782,814 A | 7/1998 | Brown et al. |
| 5,782,912 A | 7/1998 | Brauker et al. |
| 5,785,681 A | 7/1998 | Indravudh |
| 5,786,439 A | 7/1998 | Van Antwerp et al. |
| 5,786,584 A | 7/1998 | Button et al. |
| 5,787,900 A | 8/1998 | Butler et al. |
| 5,788,678 A | 8/1998 | Van Antwerp |
| 5,791,344 A | 8/1998 | Schulman et al. |
| 5,792,117 A | 8/1998 | Brown |
| 5,795,774 A | 8/1998 | Matsumoto et al. |
| 5,798,065 A | 8/1998 | Picha |
| 5,800,387 A | 9/1998 | Duffy et al. |
| 5,800,420 A | 9/1998 | Gross et al. |
| 5,800,529 A | 9/1998 | Brauker et al. |
| 5,804,048 A | 9/1998 | Wong et al. |
| 5,807,315 A | 9/1998 | Van Antwerp et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,183 A | 10/1998 | Kurnik et al. |
| 5,827,184 A | 10/1998 | Netherly et al. |
| 5,828,943 A | 10/1998 | Brown |
| 5,830,341 A | 11/1998 | Gilmartin |
| 5,832,448 A | 11/1998 | Brown |
| 5,833,603 A | 11/1998 | Kovacs et al. |
| 5,834,224 A | 11/1998 | Ruger et al. |
| 5,836,887 A | 11/1998 | Oka et al. |
| 5,836,989 A | 11/1998 | Shelton |
| 5,837,454 A | 11/1998 | Cozzette et al. |
| 5,837,546 A | 11/1998 | Allen et al. |
| 5,837,728 A | 11/1998 | Purcell |
| 5,840,020 A | 11/1998 | Heinonen et al. |
| 5,840,240 A | 11/1998 | Stenoien et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,857,967 A | 1/1999 | Frid et al. |
| 5,857,983 A | 1/1999 | Douglas et al. |
| 5,860,917 A | 1/1999 | Comanor et al. |
| 5,861,009 A | 1/1999 | Armstrong et al. |
| 5,861,019 A | 1/1999 | Sun et al. |
| 5,862,803 A | 1/1999 | Besson et al. |
| 5,871,465 A | 2/1999 | Vasko |
| 5,871,514 A | 2/1999 | Wiklund et al. |
| 5,872,713 A | 2/1999 | Douglas et al. |
| 5,872,820 A | 2/1999 | Upadrasta |
| 5,876,484 A | 3/1999 | Raskin et al. |
| 5,879,163 A | 3/1999 | Brown et al. |
| 5,879,311 A | 3/1999 | Duchon et al. |
| 5,879,373 A | 3/1999 | Roper et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,885,245 A | 3/1999 | Lynch et al. |
| 5,887,133 A | 3/1999 | Brown et al. |
| 5,895,371 A | 4/1999 | Levitas et al. |
| 5,897,493 A | 4/1999 | Brown |
| 5,897,578 A | 4/1999 | Wiklund et al. |
| 5,898,025 A | 4/1999 | Burg et al. |
| 5,899,855 A | 5/1999 | Brown |
| 5,899,931 A | 5/1999 | Deschamp et al. |
| 5,904,708 A | 5/1999 | Goedeke |
| 5,913,310 A | 6/1999 | Brown |
| 5,913,827 A | 6/1999 | Gorman |
| 5,913,998 A | 6/1999 | Butler et al. |
| 5,914,026 A | 6/1999 | Blubaugh, Jr. et al. |
| 5,916,445 A | 6/1999 | Hjerten et al. |
| 5,917,346 A | 6/1999 | Gord |
| 5,918,603 A | 7/1999 | Brown |
| 5,919,215 A | 7/1999 | Wiklund et al. |
| 5,925,021 A | 7/1999 | Castellano et al. |
| 5,928,130 A | 7/1999 | Schmidt |
| 5,931,791 A | 8/1999 | Saltzstein et al. |
| 5,931,814 A | 8/1999 | Alex et al. |
| 5,933,136 A | 8/1999 | Brown |
| 5,935,099 A | 8/1999 | Peterson et al. |
| 5,935,785 A | 8/1999 | Reber et al. |
| 5,940,801 A | 8/1999 | Brown |

| | | | | | |
|---|---|---|---|---|---|
| 5,942,979 A | 8/1999 | Luppino | 6,066,083 A | 5/2000 | Slater et al. |
| 5,945,345 A | 8/1999 | Blatt et al. | 6,066,243 A | 5/2000 | Anderson et al. |
| 5,947,749 A | 9/1999 | Rathburn | 6,066,448 A | 5/2000 | Wohlstadter et al. |
| 5,947,921 A | 9/1999 | Johnson et al. | 6,067,474 A | 5/2000 | Schulman et al. |
| 5,948,512 A | 9/1999 | Kubota et al. | 6,068,615 A | 5/2000 | Brown et al. |
| 5,950,632 A | 9/1999 | Reber et al. | 6,071,249 A | 6/2000 | Cunningham et al. |
| 5,951,300 A | 9/1999 | Brown | 6,071,251 A | 6/2000 | Cunningham et al. |
| 5,951,492 A | 9/1999 | Douglas et al. | 6,071,294 A | 6/2000 | Simons et al. |
| 5,951,521 A | 9/1999 | Mastrototaro et al. | 6,071,391 A | 6/2000 | Gotoh et al. |
| 5,951,836 A | 9/1999 | McAleer et al. | 6,071,406 A | 6/2000 | Tsou |
| 5,954,643 A | 9/1999 | Van Antwerp et al. | 6,073,049 A | 6/2000 | Alt et al. |
| 5,954,685 A | 9/1999 | Tierney | 6,081,735 A | 6/2000 | Diab et al. |
| 5,954,700 A | 9/1999 | Kovelman | 6,081,736 A | 6/2000 | Colvin et al. |
| 5,956,501 A | 9/1999 | Brown | 6,083,710 A | 7/2000 | Heller et al. |
| 5,957,854 A | 9/1999 | Besson et al. | 6,088,608 A | 7/2000 | Schulman et al. |
| 5,957,890 A | 9/1999 | Mann et al. | 6,091,975 A | 7/2000 | Daddona et al. |
| 5,957,903 A | 9/1999 | Mirzaee et al. | 6,091,976 A | 7/2000 | Pfeiffer et al. |
| 5,957,958 A | 9/1999 | Schulman et al. | 6,093,156 A | 7/2000 | Cunningham et al. |
| 5,959,050 A | 9/1999 | Mosbach et al. | 6,093,167 A | 7/2000 | Houben et al. |
| 5,960,403 A | 9/1999 | Brown | 6,093,172 A | 7/2000 | Funderburk et al. |
| 5,961,451 A | 10/1999 | Reber et al. | 6,097,831 A | 8/2000 | Wieck et al. |
| 5,964,804 A | 10/1999 | Brauker et al. | 6,099,484 A | 8/2000 | Douglas et al. |
| 5,964,993 A | 10/1999 | Blubaugh, Jr. et al. | 6,101,478 A | 8/2000 | Brown |
| 5,965,380 A | 10/1999 | Heller et al. | 6,103,033 A | 8/2000 | Say et al. |
| 5,968,839 A | 10/1999 | Blatt et al. | 6,103,533 A | 8/2000 | Hassard et al. |
| 5,971,922 A | 10/1999 | Arita et al. | 6,106,780 A | 8/2000 | Douglas et al. |
| 5,971,941 A | 10/1999 | Simons et al. | 6,107,083 A | 8/2000 | Collins et al. |
| 5,974,124 A | 10/1999 | Schlueter, Jr. et al. | 6,110,148 A | 8/2000 | Brown et al. |
| 5,976,085 A | 11/1999 | Kimball et al. | 6,110,152 A | 8/2000 | Kovelman |
| 5,977,476 A | 11/1999 | Guha et al. | 6,113,578 A | 9/2000 | Brown |
| 5,981,294 A | 11/1999 | Blatt et al. | 6,115,634 A | 9/2000 | Donders et al. |
| 5,985,129 A | 11/1999 | Gough et al. | 6,117,290 A | 9/2000 | Say et al. |
| 5,987,352 A | 11/1999 | Klein et al. | 6,119,028 A | 9/2000 | Schulman et al. |
| 5,989,409 A | 11/1999 | Kurnik et al. | 6,120,676 A | 9/2000 | Heller et al. |
| 5,994,476 A | 11/1999 | Shin et al. | 6,121,009 A | 9/2000 | Heller et al. |
| 5,995,860 A | 11/1999 | Sun et al. | 6,122,351 A | 9/2000 | Schlueter, Jr. et al. |
| 5,997,476 A | 12/1999 | Brown | 6,122,536 A | 9/2000 | Sun et al. |
| 5,999,848 A | 12/1999 | Gord et al. | 6,125,978 A | 10/2000 | Ando et al. |
| 5,999,849 A | 12/1999 | Gord et al. | 6,134,461 A | 10/2000 | Say et al. |
| 6,001,067 A | 12/1999 | Shults et al. | 6,134,504 A | 10/2000 | Douglas et al. |
| 6,001,471 A | 12/1999 | Bries et al. | 6,135,978 A | 10/2000 | Houben et al. |
| 6,002,954 A | 12/1999 | Van Antwerp et al. | 6,139,718 A | 10/2000 | Kurnik et al. |
| 6,002,961 A | 12/1999 | Mitragotri et al. | 6,141,573 A | 10/2000 | Kurnik et al. |
| 6,004,441 A | 12/1999 | Fujiwara et al. | 6,142,939 A | 11/2000 | Eppstein et al. |
| 6,007,845 A | 12/1999 | Domb | 6,142,972 A | 11/2000 | Cheikh |
| 6,011,984 A | 1/2000 | Van Antwerp et al. | 6,143,164 A | 11/2000 | Heller et al. |
| 6,013,113 A | 1/2000 | Mika | 6,144,837 A | 11/2000 | Quy |
| 6,014,577 A | 1/2000 | Henning et al. | 6,144,869 A | 11/2000 | Berner et al. |
| 6,016,448 A | 1/2000 | Busacker et al. | 6,144,922 A | 11/2000 | Douglas et al. |
| 6,017,435 A | 1/2000 | Hassard et al. | 6,148,094 A | 11/2000 | Kinsella |
| 6,018,678 A | 1/2000 | Mitragotri et al. | 6,150,128 A | 11/2000 | Uretsky |
| 6,023,629 A | 2/2000 | Tamada | 6,151,586 A | 11/2000 | Brown |
| 6,024,699 A | 2/2000 | Surwit et al. | 6,153,062 A | 11/2000 | Saito et al. |
| 6,026,320 A | 2/2000 | Carlson et al. | 6,153,069 A | 11/2000 | Pottgen et al. |
| 6,027,459 A | 2/2000 | Shain et al. | 6,154,675 A | 11/2000 | Juran et al. |
| 6,027,692 A | 2/2000 | Galen et al. | 6,159,147 A | 12/2000 | Lichter et al. |
| 6,032,059 A | 2/2000 | Henning et al. | 6,161,095 A | 12/2000 | Brown |
| 6,032,199 A | 2/2000 | Lim et al. | 6,162,611 A | 12/2000 | Heller et al. |
| 6,033,866 A | 3/2000 | Guo et al. | 6,162,639 A | 12/2000 | Douglas |
| 6,035,237 A | 3/2000 | Schulman et al. | 6,167,362 A | 12/2000 | Brown et al. |
| 6,040,194 A | 3/2000 | Chick et al. | 6,167,614 B1 | 1/2001 | Tuttle et al. |
| 6,041,253 A | 3/2000 | Kost et al. | 6,168,563 B1 | 1/2001 | Brown |
| 6,043,437 A | 3/2000 | Schulman et al. | 6,170,318 B1 | 1/2001 | Lewis |
| 6,048,691 A | 4/2000 | Maracas | 6,175,752 B1 | 1/2001 | Say et al. |
| 6,049,727 A | 4/2000 | Crothall | 6,180,416 B1 | 1/2001 | Kurnik et al. |
| 6,051,372 A | 4/2000 | Bayerl et al. | 6,186,145 B1 | 2/2001 | Brown |
| 6,056,718 A | 5/2000 | Funderburk et al. | 6,187,062 B1 | 2/2001 | Oweis et al. |
| 6,057,377 A | 5/2000 | Sasaki et al. | 6,189,536 B1 | 2/2001 | Martinez et al. |
| 6,059,946 A | 5/2000 | Yukawa et al. | 6,192,891 B1 | 2/2001 | Gravel et al. |
| 6,063,459 A | 5/2000 | Velte | 6,193,873 B1 | 2/2001 | Ohara et al. |
| 6,063,637 A | 5/2000 | Arnold et al. | 6,196,970 B1 | 3/2001 | Brown |

| Patent | Type | Date | Inventor |
|---|---|---|---|
| 6,198,957 | B1 | 3/2001 | Green |
| 6,200,265 | B1 | 3/2001 | Walsh et al. |
| 6,200,772 | B1 | 3/2001 | Vadgama et al. |
| 6,201,979 | B1 | 3/2001 | Kurnik et al. |
| 6,201,980 | B1 | 3/2001 | Darrow et al. |
| 6,201,993 | B1 | 3/2001 | Kruse et al. |
| 6,206,841 | B1 | 3/2001 | Cunningham et al. |
| 6,206,856 | B1 | 3/2001 | Mahurkar |
| 6,207,400 | B1 | 3/2001 | Kwon |
| 6,208,894 | B1 | 3/2001 | Schulman et al. |
| 6,210,272 | B1 | 4/2001 | Brown |
| 6,210,976 | B1 | 4/2001 | Sabbadini |
| 6,212,416 | B1 | 4/2001 | Ward et al. |
| 6,212,424 | B1 | 4/2001 | Robinson |
| 6,214,185 | B1 | 4/2001 | Offenbacher et al. |
| 6,219,565 | B1 | 4/2001 | Cupp et al. |
| 6,219,574 | B1 | 4/2001 | Cormier et al. |
| 6,223,083 | B1 | 4/2001 | Rosar |
| 6,223,471 | B1 | 5/2001 | Barber |
| 6,224,745 | B1 | 5/2001 | Baltruschat |
| 6,230,059 | B1 | 5/2001 | Duffin |
| 6,231,879 | B1 | 5/2001 | Li et al. |
| 6,232,130 | B1 | 5/2001 | Wolf |
| 6,232,370 | B1 | 5/2001 | Kubota et al. |
| 6,232,783 | B1 | 5/2001 | Merrill |
| 6,233,080 | B1 | 5/2001 | Brenner et al. |
| 6,233,471 | B1 | 5/2001 | Berner et al. |
| 6,233,539 | B1 | 5/2001 | Brown |
| 6,239,925 | B1 | 5/2001 | Ardrey et al. |
| 6,241,704 | B1 | 6/2001 | Peterson et al. |
| 6,241,862 | B1 | 6/2001 | McAleer et al. |
| 6,241,863 | B1 | 6/2001 | Monbouquette |
| 6,246,330 | B1 | 6/2001 | Nielsen |
| 6,246,992 | B1 | 6/2001 | Brown |
| 6,248,065 | B1 | 6/2001 | Brown |
| 6,248,067 | B1 | 6/2001 | Causey, III et al. |
| 6,248,093 | B1 | 6/2001 | Moberg |
| 6,251,260 | B1 | 6/2001 | Heller et al. |
| 6,251,280 | B1 | 6/2001 | Dai et al. |
| 6,252,032 | B1 | 6/2001 | Van Antwerp et al. |
| 6,253,804 | B1 | 7/2001 | Safabash |
| 6,254,586 | B1 | 7/2001 | Mann et al. |
| 6,256,522 | B1 | 7/2001 | Schultz |
| 6,256,643 | B1 | 7/2001 | Cork et al. |
| 6,259,587 | B1 | 7/2001 | Sheldon et al. |
| 6,259,937 | B1 | 7/2001 | Schulman et al. |
| 6,260,022 | B1 | 7/2001 | Brown |
| 6,264,825 | B1 | 7/2001 | Blackburn et al. |
| 6,266,645 | B1 | 7/2001 | Simpson |
| 6,267,724 | B1 | 7/2001 | Taylor |
| 6,268,161 | B1 | 7/2001 | Han et al. |
| 6,268,913 | B1 | 7/2001 | Rising |
| 6,270,445 | B1 | 8/2001 | Dean, Jr. et al. |
| 6,272,364 | B1 | 8/2001 | Kurnik |
| 6,272,480 | B1 | 8/2001 | Tresp et al. |
| 6,274,285 | B1 | 8/2001 | Gries et al. |
| 6,274,686 | B1 | 8/2001 | Mosbach |
| 6,275,717 | B1 | 8/2001 | Gross et al. |
| 6,280,416 | B1 | 8/2001 | Van Antwerp et al. |
| 6,280,587 | B1 | 8/2001 | Matsumoto |
| 6,281,006 | B1 | 8/2001 | Heller et al. |
| 6,283,943 | B1 | 9/2001 | Dy et al. |
| 6,284,126 | B1 | 9/2001 | Kurnik et al. |
| 6,284,478 | B1 | 9/2001 | Heller et al. |
| 6,285,897 | B1 | 9/2001 | Kilcoyne et al. |
| 6,289,238 | B1 | 9/2001 | Besson et al. |
| 6,293,925 | B1 | 9/2001 | Safabash et al. |
| 6,294,281 | B1 | 9/2001 | Heller |
| 6,295,463 | B1 | 9/2001 | Stenzler |
| 6,295,506 | B1 | 9/2001 | Heinonen et al. |
| 6,298,254 | B2 | 10/2001 | Tamada |
| 6,299,578 | B1 | 10/2001 | Kurnik et al. |
| 6,299,757 | B1 | 10/2001 | Feldman et al. |
| 6,300,002 | B1 | 10/2001 | Webb et al. |
| 6,301,499 | B1 | 10/2001 | Carlson et al. |
| 6,304,766 | B1 | 10/2001 | Colvin |
| 6,309,351 | B1 | 10/2001 | Kurnik et al. |
| 6,309,384 | B1 | 10/2001 | Harrington et al. |
| 6,309,526 | B1 | 10/2001 | Fujiwara et al. |
| 6,309,884 | B1 | 10/2001 | Cooper et al. |
| 6,310,110 | B1 | 10/2001 | Markowitz et al. |
| 6,315,721 | B2 | 11/2001 | Schulman et al. |
| 6,315,738 | B1 | 11/2001 | Nishikawa et al. |
| 6,319,540 | B1 | 11/2001 | Van Antwerp et al. |
| 6,319,566 | B1 | 11/2001 | Polanyi et al. |
| 6,320,357 | B1 | 11/2001 | Peters et al. |
| 6,324,428 | B1 | 11/2001 | Weinberg et al. |
| 6,325,978 | B1 | 12/2001 | Labuda et al. |
| 6,325,979 | B1 | 12/2001 | Hahn et al. |
| 6,326,160 | B1 | 12/2001 | Dunn et al. |
| 6,329,161 | B1 | 12/2001 | Heller et al. |
| 6,329,929 | B1 | 12/2001 | Weijand et al. |
| 6,330,426 | B2 | 12/2001 | Brown et al. |
| 6,330,464 | B1 | 12/2001 | Colvin, Jr. et al. |
| 6,331,518 | B2 | 12/2001 | Hemm et al. |
| 6,334,778 | B1 | 1/2002 | Brown |
| 6,336,900 | B1 | 1/2002 | Alleckson et al. |
| 6,338,790 | B1 | 1/2002 | Feldman et al. |
| 6,340,421 | B1 | 1/2002 | Vachon et al. |
| 6,341,232 | B1 | 1/2002 | Conn et al. |
| 6,343,225 | B1 | 1/2002 | Clark, Jr. |
| 6,356,776 | B1 | 3/2002 | Berner et al. |
| 6,358,237 | B1 | 3/2002 | Paukovits et al. |
| 6,360,888 | B1 | 3/2002 | McIvor et al. |
| 6,363,282 | B1 | 3/2002 | Nichols et al. |
| 6,365,670 | B1 | 4/2002 | Fry |
| 6,366,793 | B1 | 4/2002 | Bell et al. |
| 6,366,794 | B1 | 4/2002 | Moussy et al. |
| 6,368,141 | B1 | 4/2002 | Van Antwerp et al. |
| 6,368,274 | B1 | 4/2002 | Van Antwerp et al. |
| 6,370,410 | B2 | 4/2002 | Kurnik et al. |
| 6,379,301 | B1 | 4/2002 | Worthington et al. |
| 6,379,317 | B1 | 4/2002 | Kintzig et al. |
| 6,383,767 | B1 | 5/2002 | Polak |
| 6,387,048 | B1 | 5/2002 | Schulman et al. |
| 6,391,643 | B1 | 5/2002 | Chen et al. |
| 6,393,318 | B1 | 5/2002 | Chen et al. |
| 6,398,562 | B1 | 6/2002 | Butler et al. |
| 6,398,727 | B1 | 6/2002 | Bui et al. |
| 6,402,689 | B1 | 6/2002 | Scarantino et al. |
| 6,402,691 | B1 | 6/2002 | Peddicord et al. |
| 6,405,066 | B1 | 6/2002 | Essenpreis et al. |
| 6,406,066 | B1 | 6/2002 | Uegane |
| 6,406,426 | B1 | 6/2002 | Reuss et al. |
| 6,409,674 | B1 | 6/2002 | Brockway et al. |
| 6,413,393 | B1 | 7/2002 | Van Antwerp et al. |
| 6,416,471 | B1 | 7/2002 | Kumar et al. |
| 6,418,332 | B1 | 7/2002 | Mastrototaro et al. |
| 6,418,346 | B1 | 7/2002 | Nelson et al. |
| 6,424,847 | B1 | 7/2002 | Mastrototaro et al. |
| 6,424,867 | B1 | 7/2002 | Snell et al. |
| 6,427,088 | B1 | 7/2002 | Bowman, IV et al. |
| 6,434,409 | B1 | 8/2002 | Pfeiffer et al. |
| 6,438,414 | B1 | 8/2002 | Conn et al. |
| 6,440,068 | B1 | 8/2002 | Brown et al. |
| 6,442,433 | B1 | 8/2002 | Linberg |
| 6,442,637 | B1 | 8/2002 | Hawkins et al. |
| 6,443,942 | B2 | 9/2002 | Van Antwerp et al. |
| 6,447,448 | B1 | 9/2002 | Ishikawa et al. |
| 6,447,542 | B1 | 9/2002 | Weadock |
| 6,454,710 | B1 | 9/2002 | Ballerstadt et al. |
| 6,459,917 | B1 | 10/2002 | Gowda et al. |

| Patent | Date | Name |
|---|---|---|
| 6,461,496 B1 | 10/2002 | Feldman et al. |
| 6,462,162 B2 | 10/2002 | Van Antwerp et al. |
| 6,464,687 B1 | 10/2002 | Ishikawa et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,469,526 B1 | 10/2002 | Franklin |
| 6,471,645 B1 | 10/2002 | Warkentin et al. |
| 6,471,689 B1 | 10/2002 | Joseph et al. |
| 6,472,122 B1 | 10/2002 | Schulman et al. |
| 6,475,180 B2 | 11/2002 | Peterson et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,478,736 B1 | 11/2002 | Mault |
| 6,480,730 B2 | 11/2002 | Darrow et al. |
| 6,481,440 B2 | 11/2002 | Gielen et al. |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,485,465 B2 | 11/2002 | Moberg et al. |
| 6,494,830 B1 | 12/2002 | Wessel |
| 6,496,728 B2 | 12/2002 | Li et al. |
| 6,498,043 B1 | 12/2002 | Schulman et al. |
| 6,498,941 B1 | 12/2002 | Jackson |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,528,584 B2 | 3/2003 | Kennedy et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,537,318 B1 | 3/2003 | Ita et al. |
| 6,540,675 B2 | 4/2003 | Aceti et al. |
| 6,541,107 B1 | 4/2003 | King et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,549,796 B2 | 4/2003 | Sohrab |
| 6,551,276 B1 | 4/2003 | Mann et al. |
| 6,551,494 B1 | 4/2003 | Iteller et al. |
| 6,551,496 B1 | 4/2003 | Moles et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,569,521 B1 | 5/2003 | Sheridan et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,588,644 B2 | 7/2003 | Simon |
| 6,589,205 B1 | 7/2003 | Meadows |
| 6,589,229 B1 | 7/2003 | Connelly et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,072 B2 | 8/2003 | Struys et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,658 B1 | 8/2003 | Heller et al. |
| 6,610,012 B2 | 8/2003 | Mault |
| 6,612,306 B1 | 9/2003 | Mault |
| 6,612,984 B1 | 9/2003 | Kerr |
| 6,613,379 B2 | 9/2003 | Ward et al. |
| 6,615,078 B1 | 9/2003 | Burson et al. |
| 6,616,819 B1 | 9/2003 | Liamos et al. |
| 6,618,603 B2 | 9/2003 | Varalli et al. |
| 6,618,934 B1 | 9/2003 | Feldman et al. |
| 6,620,106 B2 | 9/2003 | Mault |
| 6,627,058 B1 | 9/2003 | Chan |
| 6,629,776 B2 | 10/2003 | Bell et al. |
| 6,629,934 B2 | 10/2003 | Mault et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,642,015 B2 | 11/2003 | Vachon et al. |
| 6,644,321 B1 | 11/2003 | Behm |
| 6,645,142 B2 | 11/2003 | Braig et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,596 B1 | 1/2004 | Sayler et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,683,535 B1 | 1/2004 | Utke |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,689,091 B2 | 2/2004 | Bui et al. |
| 6,689,265 B2 | 2/2004 | Heller et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,704,587 B1 | 3/2004 | Kumar et al. |
| 6,705,833 B2 | 3/2004 | Tam et al. |

| | | | | | | |
|---|---|---|---|---|---|---|
| 6,708,049 B1 | 3/2004 | Berson et al. | | 6,891,317 B2 | 5/2005 | Pei et al. |
| 6,711,423 B2 | 3/2004 | Colvin, Jr. | | 6,892,085 B2 | 5/2005 | McIvor et al. |
| 6,721,587 B2 | 4/2004 | Gough | | 6,893,552 B1 | 5/2005 | Wang et al. |
| 6,723,046 B2 | 4/2004 | Lichtenstein et al. | | 6,895,263 B2 | 5/2005 | Shin et al. |
| 6,728,560 B2 | 4/2004 | Kollias et al. | | 6,899,683 B2 | 5/2005 | Mault et al. |
| 6,730,200 B1 | 5/2004 | Stewert et al. | | 6,899,684 B2 | 5/2005 | Mault et al. |
| 6,731,976 B2 | 5/2004 | Penn et al. | | 6,902,905 B2 | 6/2005 | Burson et al. |
| 6,733,446 B2 | 5/2004 | Lebel et al. | | 6,904,301 B2 | 6/2005 | Raskas |
| 6,734,162 B2 | 5/2004 | Van Antwerp et al. | | 6,907,127 B1 | 6/2005 | Kravitz et al. |
| 6,736,777 B2 | 5/2004 | Kim et al. | | 6,915,147 B2 | 7/2005 | Lebel et al. |
| 6,737,401 B2 | 5/2004 | Kim et al. | | 6,918,874 B1 | 7/2005 | Hatch et al. |
| 6,738,654 B2 | 5/2004 | Sohrab | | 6,922,578 B2 | 7/2005 | Eppstein et al. |
| 6,740,075 B2 | 5/2004 | Lebel et al. | | 6,922,584 B2 | 7/2005 | Wang et al. |
| 6,741,163 B1 | 5/2004 | Roberts | | RE38,775 E | 8/2005 | Kurnik et al. |
| 6,741,876 B1 | 5/2004 | Scecina et al. | | 6,923,764 B2 | 8/2005 | Aceti et al. |
| 6,741,877 B1 | 5/2004 | Shults et al. | | 6,923,936 B2 | 8/2005 | Swanson et al. |
| 6,749,587 B2 | 6/2004 | Flaherty | | 6,927,246 B2 | 8/2005 | Noronha et al. |
| 6,750,311 B1 | 6/2004 | Van Antwerp et al. | | 6,931,327 B2 | 8/2005 | Goode, Jr. et al. |
| 6,758,810 B2 | 7/2004 | Lebel et al. | | 6,932,084 B2 | 8/2005 | Estes et al. |
| 6,766,183 B2 | 7/2004 | Walsh et al. | | 6,932,894 B2 | 8/2005 | Mao et al. |
| 6,766,201 B2 | 7/2004 | Von Arx et al. | | 6,936,006 B2 | 8/2005 | Sabra |
| 6,768,425 B2 | 7/2004 | Flaherty et al. | | 6,936,029 B2 | 8/2005 | Mann et al. |
| 6,770,030 B1 | 8/2004 | Schaupp et al. | | 6,940,590 B2 | 9/2005 | Colvin, Jr. et al. |
| 6,770,729 B2 | 8/2004 | Van Antwerp et al. | | 6,941,163 B2 | 9/2005 | Ford et al. |
| 6,771,995 B2 | 8/2004 | Kurnik et al. | | 6,946,996 B2 | 9/2005 | Koyama |
| 6,773,563 B2 | 8/2004 | Matsumoto | | 6,950,708 B2 | 9/2005 | Bowman IV et al. |
| 6,773,565 B2 | 8/2004 | Kunimoto et al. | | 6,952,603 B2 | 10/2005 | Gerber et al. |
| 6,780,297 B2 | 8/2004 | Matsumoto et al. | | 6,954,673 B2 | 10/2005 | Von Arx et al. |
| 6,780,871 B2 | 8/2004 | Glick et al. | | 6,955,650 B2 | 10/2005 | Mault et al. |
| 6,784,274 B2 | 8/2004 | Van Antwerp et al. | | 6,957,102 B2 | 10/2005 | Silver et al. |
| 6,790,178 B1 | 9/2004 | Mault et al. | | 6,957,107 B2 | 10/2005 | Rogers et al. |
| 6,793,802 B2 | 9/2004 | Lee et al. | | 6,958,705 B2 | 10/2005 | Lebel et al. |
| 6,794,195 B2 | 9/2004 | Colvin, Jr. | | 6,965,791 B1 | 11/2005 | Hitchcock et al. |
| 6,799,149 B2 | 9/2004 | Hartlaub | | 6,968,294 B2 | 11/2005 | Gutta et al. |
| 6,800,451 B2 | 10/2004 | Daniloff et al. | | 6,968,375 B1 | 11/2005 | Brown |
| 6,801,041 B2 | 10/2004 | Karinka et al. | | 6,973,706 B2 | 12/2005 | Say et al. |
| 6,801,420 B2 | 10/2004 | Talbot et al. | | 6,974,437 B2 | 12/2005 | Lebel et al. |
| 6,802,957 B2 | 10/2004 | Jung et al. | | 6,978,182 B2 | 12/2005 | Mazar et al. |
| 6,804,544 B2 | 10/2004 | Van Antwerp et al. | | 6,979,326 B2 | 12/2005 | Mann et al. |
| 6,809,507 B2 | 10/2004 | Morgan et al. | | 6,990,366 B2 | 1/2006 | Say et al. |
| 6,809,653 B1 | 10/2004 | Mann et al. | | 6,991,096 B2 | 1/2006 | Gottlieb et al. |
| 6,810,290 B2 | 10/2004 | Lebel et al. | | 6,997,907 B2 | 2/2006 | Safabash et al. |
| 6,811,533 B2 | 11/2004 | Lebel et al. | | 6,997,920 B2 | 2/2006 | Mann et al. |
| 6,811,534 B2 | 11/2004 | Bowman, IV et al. | | 6,998,247 B2 | 2/2006 | Monfre et al. |
| 6,811,659 B2 | 11/2004 | Vachon | | 6,999,810 B2 | 2/2006 | Berner et al. |
| 6,812,031 B1 | 11/2004 | Carlsson | | 7,003,336 B2 | 2/2006 | Holker et al. |
| 6,813,516 B2 | 11/2004 | Ujhelyi et al. | | 7,003,341 B2 | 2/2006 | Say et al. |
| 6,813,519 B2 | 11/2004 | Lebel et al. | | 7,004,901 B2 | 2/2006 | Fish |
| 6,815,186 B2 | 11/2004 | Clark, Jr. | | 7,005,857 B2 | 2/2006 | Stiene et al. |
| 6,816,742 B2 | 11/2004 | Kim et al. | | 7,011,630 B2 | 3/2006 | Desai et al. |
| 6,835,553 B2 | 12/2004 | Han et al. | | 7,016,721 B2 | 3/2006 | Lee et al. |
| RE38,681 E | 1/2005 | Kurnik et al. | | 7,018,366 B2 | 3/2006 | Easter |
| 6,840,912 B2 | 1/2005 | Kloepfer et al. | | 7,018,568 B2 | 3/2006 | Tierney |
| 6,844,023 B2 | 1/2005 | Schulman et al. | | 7,022,072 B2 | 4/2006 | Fox et al. |
| 6,849,237 B2 | 2/2005 | Housefield et al. | | 7,024,236 B2 | 4/2006 | Ford et al. |
| 6,850,790 B2 | 2/2005 | Berner et al. | | 7,024,245 B2 | 4/2006 | Lebel et al. |
| 6,852,500 B1 | 2/2005 | Hoss et al. | | 7,025,743 B2 | 4/2006 | Mann et al. |
| 6,852,694 B2 | 2/2005 | Van Antwerp et al. | | 7,029,444 B2 | 4/2006 | Shin et al. |
| 6,853,854 B1 | 2/2005 | Proniewicz et al. | | 7,039,810 B1 | 5/2006 | Nichols |
| 6,855,115 B2 | 2/2005 | Fonseca et al. | | 7,041,468 B2 | 5/2006 | Drucker et al. |
| 6,856,928 B2 | 2/2005 | Harmon | | 7,049,277 B2 | 5/2006 | Bagulla et al. |
| 6,858,403 B2 | 2/2005 | Han et al. | | 7,052,472 B1 | 5/2006 | Miller et al. |
| 6,862,465 B2 | 3/2005 | Shults et al. | | 7,052,483 B2 | 5/2006 | Wojcik |
| 6,862,466 B2 | 3/2005 | Ackerman | | 7,056,302 B2 | 6/2006 | Douglas |
| 6,872,200 B2 | 3/2005 | Mann et al. | | 7,070,580 B2 | 7/2006 | Nielsen |
| 6,873,268 B2 | 3/2005 | Lebel et al. | | 7,072,718 B2 | 7/2006 | VonArx et al. |
| 6,875,386 B1 | 4/2005 | Ward et al. | | 7,072,802 B2 | 7/2006 | Hartlaub |
| 6,879,849 B2 | 4/2005 | Begic | | 7,074,307 B2 | 7/2006 | Simpson et al. |
| 6,881,551 B2 | 4/2005 | Heller et al. | | 7,081,195 B2 | 7/2006 | Simpson et al. |
| 6,882,940 B2 | 4/2005 | Potts et al. | | 7,082,334 B2 | 7/2006 | Boute et al. |
| 6,885,883 B2 | 4/2005 | Parris et al. | | 7,098,803 B2 | 8/2006 | Mann et al. |

| Patent/Publication | Date | Inventor |
|---|---|---|
| 7,108,778 B2 | 9/2006 | Simpson et al. |
| 7,109,878 B2 | 9/2006 | Mann et al. |
| 7,110,803 B2 | 9/2006 | Shults et al. |
| 7,113,821 B1 | 9/2006 | Sun et al. |
| 7,115,884 B1 | 10/2006 | Walt et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,150,975 B2 | 12/2006 | Tamada et al. |
| 7,163,511 B2 | 1/2007 | Conn et al. |
| 7,166,074 B2 | 1/2007 | Reghabit et al. |
| 7,171,274 B2 | 1/2007 | Starkweather et al. |
| 7,177,690 B2 | 2/2007 | Woods et al. |
| 7,183,068 B2 | 2/2007 | Burson et al. |
| 7,183,102 B2 | 2/2007 | Monfre et al. |
| 7,187,528 B2 | 3/2007 | Talbot et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,226,978 B2 | 6/2007 | Tapsak et al. |
| 7,228,163 B2 | 6/2007 | Ackerman |
| 7,233,817 B2 | 6/2007 | Yen |
| 7,248,929 B2 | 7/2007 | Meadows et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,295,867 B2 | 11/2007 | Berner et al. |
| 7,310,544 B2 | 12/2007 | Brister et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0009810 A1 | 1/2002 | O'Connor et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019330 A1 | 2/2002 | Murray et al. |
| 2002/0019586 A1 | 2/2002 | Teller et al. |
| 2002/0019748 A1 | 2/2002 | Brown |
| 2002/0022883 A1 | 2/2002 | Burg |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065453 A1 | 5/2002 | Lesho et al. |
| 2002/0068858 A1 | 6/2002 | Braig et al. |
| 2002/0068860 A1 | 6/2002 | Clark, Jr. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0099282 A1 | 7/2002 | Knobbe et al. |
| 2002/0099997 A1 | 7/2002 | Piret |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0111547 A1 | 8/2002 | Knobbe et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0161286 A1 | 10/2002 | Gerber et al. |
| 2002/0161288 A1 | 10/2002 | Shin et al. |
| 2002/0177764 A1 | 11/2002 | Sohrab |
| 2002/0182241 A1 | 12/2002 | Boerenstein et al. |
| 2002/0193885 A1 | 12/2002 | Legeay et al. |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0059631 A1 | 3/2003 | Al-Lamee |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |

| | | |
|---|---|---|
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0188427 A1 | 10/2003 | Say et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199744 A1 | 10/2003 | Buse et al. |
| 2003/0199791 A1 | 10/2003 | Boecker et al. |
| 2003/0199903 A1 | 10/2003 | Boecker et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0211625 A1 | 11/2003 | Cohan |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225437 A1 | 12/2003 | Ferguson |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015134 A1 | 1/2004 | Lavi et al. |
| 2004/0018486 A1 | 1/2004 | Dunn et al. |
| 2004/0030285 A1 | 2/2004 | Lavi et al. |
| 2004/0030294 A1 | 2/2004 | Mahurkar |
| 2004/0039256 A1 | 2/2004 | Kawatahara et al. |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0068230 A1 | 4/2004 | Estes et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0074785 A1 | 4/2004 | Holker |
| 2004/0078219 A1 | 4/2004 | Kaylor |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0138588 A1 | 7/2004 | Saikley et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2005/0003470 A1 | 1/2005 | Nelson et al. |
| 2005/0010087 A1 | 1/2005 | Banet et al. |
| 2005/0010269 A1 | 1/2005 | Lebel et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Kieth et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0239156 A1 | 10/2005 | Drucker et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |

| Publication No. | Date | Inventor |
|---|---|---|
| 2005/0261563 A1 | 11/2005 | Zhou et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0063218 A1 | 3/2006 | Bartkowiak et al. |
| 2006/0068208 A1 | 3/2006 | Tapsak et al. |
| 2006/0074564 A1 | 4/2006 | Bartkowiak et al. |
| 2006/0086624 A1 | 4/2006 | Tapsak et al. |
| 2006/0155180 A1 | 7/2006 | Brister et al. |
| 2006/0173444 A1 | 8/2006 | Choy et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200020 A1 | 9/2006 | Brister et al. |
| 2006/0200022 A1 | 9/2006 | Brauker et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0235285 A1 | 10/2006 | Brister et al. |
| 2006/0247985 A1 | 11/2006 | Liamos et al. |
| 2006/0258761 A1 | 11/2006 | Boock et al. |
| 2006/0258929 A1 | 11/2006 | Goode, Jr. et al. |
| 2006/0270922 A1 | 11/2006 | Brauker et al. |
| 2006/0270923 A1 | 11/2006 | Brauker et al. |
| 2007/0016381 A1 | 1/2007 | Kamath et al. |
| 2007/0017805 A1 | 1/2007 | Hodges et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0045902 A1 | 3/2007 | Brauker et al. |
| 2007/0060814 A1 | 3/2007 | Stafford |
| 2007/0066873 A1 | 3/2007 | Kamath et al. |
| 2007/0078320 A1 | 4/2007 | Stafford |
| 2007/0078321 A1 | 4/2007 | Mazza et al. |
| 2007/0093704 A1 | 4/2007 | Brister et al. |
| 2007/0106135 A1 | 5/2007 | Sloan et al. |
| 2007/0149873 A1 | 6/2007 | Say et al. |
| 2007/0149874 A1 | 6/2007 | Say et al. |
| 2007/0151869 A1 | 7/2007 | Heller et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0197889 A1 | 8/2007 | Brister et al. |
| 2007/0197890 A1 | 8/2007 | Boock et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0208247 A1 | 9/2007 | Say et al. |
| 2007/0213610 A1 | 9/2007 | Say et al. |
| 2007/0215491 A1 | 9/2007 | Heller et al. |
| 2007/0218097 A1 | 9/2007 | Heller et al. |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2008/0167543 A1 | 7/2008 | Say et al. |
| 2008/0214914 A1 | 9/2008 | Say et al. |

FOREIGN PATENT DOCUMENTS

| | | |
|---|---|---|
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0 320 109 | 6/1989 |
| EP | 0 353 328 | 2/1990 |
| EP | 0359831 | 3/1990 |
| EP | 0368209 | 5/1990 |
| EP | 0368290 | 5/1990 |
| EP | 368290 | 5/1990 |
| EP | 0390390 | 10/1990 |
| EP | 0 390 390 | 10/1990 |
| EP | 390390 | 10/1990 |
| EP | 0 396 788 | 11/1990 |
| EP | 0400918 | 12/1990 |
| EP | 0453283 | 10/1991 |
| EP | 0512122 | 11/1992 |
| EP | 0535898 | 4/1993 |
| EP | 0539625 | 5/1993 |
| EP | 0561966 | 10/1994 |
| EP | 0776628 | 6/1997 |
| EP | 0800082 | 10/1997 |
| EP | 0817809 | 1/1998 |
| EP | 0838230 | 4/1998 |
| EP | 0880936 | 12/1998 |
| EP | 0885932 | 12/1998 |
| EP | 0967788 | 12/1999 |
| EP | 0970655 | 1/2000 |
| EP | 1034734 | 9/2000 |
| EP | 1 048 264 | 11/2000 |
| EP | 1077634 | 2/2001 |

| | | |
|---|---|---|
| EP | 1078258 | 2/2001 |
| GB | 1394171 | 5/1975 |
| GB | 1442303 | 7/1976 |
| GB | 1579690 | 11/1980 |
| GB | 1599241 | 9/1981 |
| GB | 2073891 | 10/1981 |
| GB | 2 149 918 | 6/1985 |
| GB | 2149918 | 6/1985 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 55-010581 | 1/1980 |
| JP | 55-010583 | 1/1980 |
| JP | 55-010584 | 1/1980 |
| JP | 56-163447 | 12/1981 |
| JP | 62-083849 | 4/1987 |
| JP | 63-139246 | 6/1988 |
| JP | 6-190050 | 7/1994 |
| JP | 8-154903 | 6/1996 |
| JP | 2002-189015 | 7/2002 |
| WO | WO-85/05119 | 11/1985 |
| WO | WO85005199 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/00738 | 1/1990 |
| WO | WO-90/05300 | 5/1990 |
| WO | WO-90/05910 | 5/1990 |
| WO | WO-90/13021 | 11/1990 |
| WO | WO-91/01680 | 2/1991 |
| WO | WO-91/04704 | 4/1991 |
| WO | WO-91/15993 | 10/1991 |
| WO | WO-92/07525 | 5/1992 |
| WO | WO-92/10584 | 6/1992 |
| WO | WO-92/13271 | 8/1992 |
| WO | WO-93/19701 | 10/1993 |
| WO | WO-94/20602 | 9/1994 |
| WO | WO-94/22367 | 10/1994 |
| WO | WO-94/27140 | 11/1994 |
| WO | WO-95/06240 | 3/1995 |
| WO | WO-95/07109 | 3/1995 |
| WO | WO-96/01611 | 1/1996 |
| WO | WO-96/07908 | 3/1996 |
| WO | WO 96/14026 | 5/1996 |
| WO | WO9614026 | 5/1996 |
| WO | WO 96/25089 | 8/1996 |
| WO | WO-96/30431 | 10/1996 |
| WO | WO-96/32076 | 10/1996 |
| WO | WO 96/35370 | 11/1996 |
| WO | WO-96/35370 | 11/1996 |
| WO | WO-96/36296 | 11/1996 |
| WO | WO 97/01986 | 1/1997 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24358 | 6/1998 |
| WO | WO-98/24366 | 6/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/48419 | 9/1999 |
| WO | WO 99/56613 | 11/1999 |
| WO | WO-99/56613 | 11/1999 |
| WO | WO-99/58051 | 11/1999 |
| WO | WO-99/58973 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/32098 | 6/2000 |
| WO | WO-00/33065 | 6/2000 |
| WO | WO 00/49940 | 8/2000 |
| WO | WO 00/59370 | 10/2000 |
| WO | WO-00/59373 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/12158 | 2/2001 |
| WO | WO-01/20019 | 3/2001 |
| WO | WO-01/20334 | 3/2001 |
| WO | WO01020334 | 3/2001 |
| WO | WO-01/24038 | 4/2001 |
| WO | WO01024038 | 4/2001 |
| WO | WO-01/33216 | 5/2001 |
| WO | WO-01/43660 | 6/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/58348 | 8/2001 |
| WO | WO-01/67009 | 9/2001 |
| WO | WO-01/68901 | 9/2001 |
| WO | WO-01/69222 | 9/2001 |
| WO | WO-01/88524 | 11/2001 |
| WO | WO-01/88534 | 11/2001 |
| WO | WO-02/16905 | 2/2002 |
| WO | WO-02/17210 | 2/2002 |
| WO | WO-02/24065 | 3/2002 |
| WO | WO-02/058537 | 8/2002 |
| WO | WO 02/058537 A2 | 8/2002 |
| WO | WO-02/078512 | 10/2002 |
| WO | WO-02/082989 | 10/2002 |
| WO | WO-03/072269 | 9/2003 |
| WO | WO-03/076893 | 9/2003 |
| WO | WO-03/082091 | 10/2003 |
| WO | WO-03/101862 | 12/2003 |
| WO | WO-2004/061420 | 7/2004 |
| WO | WO-2005/089103 | 9/2005 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO 2007/051139 | 5/2007 |
| WO | WO-2007/053832 | 5/2007 |
| WO | WO-2007/056638 | 5/2007 |
| WO | WO-2007/120363 | 10/2007 |

OTHER PUBLICATIONS

Bindra et al., "Design and in Vitro Studies of a Needle–Type Glucose Sensor for Subcutaneous Monitoring," Anal. Chem., 1991, vol. 63, pp. 1692–1696.

Brooks S. et al., "Development of an On–line Glucose Sensor for Fermentation Monitoring," (1987/88) Biosensors 3:45–56.

Cerami, "Monitor for continuous in vivo measurement of glucose concentration," United States Patent 4,436,004, issued Mar. 13, 1984, 2 pages (Abstract only).

Dai et al., "Hydrogel Membranes with Mesh Size Asymmtery Based on the Gradient Crosslinking of Poly(vinyl alcohol)," Journal of Membrane Science, 156 (1999) 67–79.

Diabetes Research in Children Network (DirecNet) Study Group. "Accuracy of the Gluco Watch G2 Biographer and the continuous glucose monitoring system during hypoglycemia: experience of the Diabetes Research in Children Network," Diabetes Care. Mar. 2004;27(3):722–6.

Flentge, F. et al., "An Enzyme–Reactor for Electrochemical Monitoring of Choline and Acetylcholine: Applications in High–Performance Liquid Chromatrography, Drain Tissue, Microdialysis and Cerebrospinal Fluid", Analytical Biochemistry, vol. 204, No. 2, pp. 305–310 (Aug. 1, 1992).

Franetzki, "Implantable, calibrateable measuring instrument for a body substance and a calibrating method," United States Patent 4,759,371, issue Jul. 26, 1988, 2 pages (Abstract only).

GJ Kemp, "Theoretical Aspects of One–Point Calibration," Clinical Chemistry, 30/7 1163–1167 (1984).

Graham, "Poly(ethylene Oxide) and Related Hydrogels," Hydrogels in Medicine and Pharmacy, Chapter 4, CRC Press, 1987.

Hamilton Needle Gauge Index, www.hamiltoncompany.com, undated.

Kulys, J. et al., "Mediatorless peroxidase electrode and preparation of bioenzyme sensors," Bioelectrochemistry and Bioelectronics, 6(1):31–36 (1990).

Laurell, T., "A Continuous Glucose Monitoring System Based on Microdialysis", Journal of Med Eng. & Tech., vol. 16, No. 5, pp. 187–193 (Sep./Oct. 1992).

Marko–Varga, G. et al., "Enzyme–Based Biosensor as a Selective Detection Unit in Column Liquid Chromatography", Journal of Chromatography, vol. 660, pp. 153–167 (1994).

Mauras et al., "Lack of accuracy of continuous glucose sensors in healthy, nondiabetic children: results of the Diabetes Research in Children Network (DirecNet) accuracy study," J Pediatr. Jun. 2004;144(6):770–5.

Reusch et al., "Special Topics: Organometallic Compounds," Virtual Textbook of Organic Chemistry, pp. 11–12 (1999, latest revision 2004).

Sacks, ed., "Guidelines and Recommendations for Laboratory Analysis in the Diagnosis and Management of Diabetes Mellitus," (2002) in "Lab. Med. Practice Guidelines," vol. 13, pub. by Nat. Acad. Clin Biochem.

Scheller et al., "Second Generation Biosensors," Biosens Bioelectron. 1991;6(3):245–53.

Schmidt, F.J. et al., "Calibration of a Wearable Glucose Sensor", The International Journal of Artificial Organs, vol. 15 No. 1, pp. 55–61 (1992).

Shichiri et al., "The Development of Wearable–Type Artificial Endocrine Pancreas and its Usefulness in Glycaemic Control of Human Diabetes Mellitus," Biomed. Biochim Acta 43(5), 561–568, 1984.

Skoog & West, "Fundamentals of Analytical Chemistry," Holt, Rinehart & Winston, Inc. New York (1966), p. 55.

Takamura et al., Drug Release from Ploy(Vinyl Alcohol) Gel Prepared by Freeze–Thaw Procedure, J Controlled Release, 20 (1992) 21–28.

Godsland and Walton, "Maximizing the success rate of minimal model insulin sensitivity measurement in humans: the importance of basal glucose levels," Clinical Science (2001) 101:1–9.

Johnson, et al. 1992. In vivo evaluation of an electroenzymatic glucose sensor implanted in subcutaneous tissue. Biosensors & Bioelectronics 7:709–714.

Kerner et al., "The function of a hydrogen peroxide–detecting electroenzymatic glucose electrode is markedly impaired in human sub–cutaneous tissue and plasma," Biosensors & Bioelectronics (1993) 8:473–482.

Kulys, J. et al., "Mediatorless peroxidase electrode and preparation of bioenzyme sensors," Bioelectrochemistry and Bioelectronics, 6(1):31–36 (1990).

Laurell. T., "A Continuous Glucose Monitoring System Based on Microdialysis", Journal of Med Eng. & Tech., vol. 16, No. 5, pp. 187–193 (Sep./Oct. 1992).

Sakakida, et al. Development of Ferrocene–Mediated Needle–Type Glucose Sensor as a Measure of True Subcutaneous Tissue Glucose Concentrations, Artif. Organs Today, vol. 2, No. 2, pp. 145–158.

Shichiri, et al., Membrane Design For Extending the Long–Life of an Implantable Glucose Sensor, Diab. Nutr. Metab., 2, pp. 309–313 (1989).

Shichiri, M. et al., "Glycaemic Control in Pancreatotomized Dogs with a Wearable Artificial Endocrine Pancreas", Diabetologia, 24(3): 179–184 (Mar. 1983).

Armour et al., Diabetes (1990) 39:1519–1526.

Ko et al., (ed.), Chapter 15 in "Implantable Sensors for Closed Loop Prosthetic Systems" Mount Sisco, NY: Futura Publishing Company, Inc. (1985) pp. 197–210.

Mckean et al., IEEE Transactions On Biomedical Engineering (1988) 35 (7):526–532.

Shults et al., IEEE Transactions On Biomedical Engineering (1994) 41(10):937–942.

Updike et al., Chapter 4 in "Biosensors in the Body: Continuous in vivo Monitoring " John Wiley & Sons Ltd. (1997) pp. 117–137.

Salehi et al., "Telemetry–Instrumentation System for Long–Term Implantable Glucose and Oxygen Sensors," Analytical Letters, NY, US, vol. 29, No. 13, 1996, pp. 2289–2308.

Moatti–Sirat, D et al., "Reduction of acetaminophen interference in glucose sensors by a composite Nafion membrane: demonstration in rats and man," (1 page—Abstract only) Diabetologica, 37(6):610–6 (Jun. 1994).

Pickup J. et al., "Implantable Glucose Sensors: Choosing the Appropriate Sensing Strategy," (1987/88) *Biosensors* 3:335–346.

Shaw GW et al., "In vitro testing of a simply constructed, highly stable glucose sensor suitable for implantation in diabetic patients," *Biosensors & Bioelectronics* 6:401–406.

Petrou, et al., 2003, "Microdevice with Integrated Dialysis Probe and Biosensor Array for Multi–Analyte Monitoring Continuous," *Biosensors & Bioelectronics,* vol. 18: p. 613–619.

Poscia, et al., 2003, "A Microdialysis Technique for Continuous Subcutaneous Glucose Monitoring in Diabetic Patients (Part 1)," *Biosensors & Bioelectronics,* vol. 18: p. 891–898.

Varalli, et al., 2003, "A Microdialysis Technique for Continuous Subcutaneous Glucose Monitoring in Diabetic Patients (Part 2)," *Biosensors & Bioelectronics,* vol. 18: p. 899–905.

Armour, et al., 1990, "Application Of Chronic Intravascular Blood Glucose Sensor In Dogs," *Diabetes,* vol. 39: p. 1519–1526.
Kaplan, 2004 "Wiley Electrical And Electronics Engineering Dictionary," John Wiley & Sons, Hoboken, New Jersey: p. 141–142, 548–549.
McKean, et al., 1988, "A Telemetry–Instrumentation System For Chronically Implanted Glucose And Oxygen Sensors," *IEE Transactions on Biomedical Engineering,* vol. 35, No. 7: p. 526–532.
Merriam–Webster's Medical Desk Dictionary, 2005, Merriam–Webster, Incorporated, Springfield, Massachussetts, U.S.A.: p. 843.
Pishko, et al., 1991, "Amperometric Glucose Microelectrodes Prepared Through Immobilization Of Glucose Oxidase In Redox Hydrogels," *Analytical Chemistry,* vol. 63, No. 20: p. 2268–2272.
Schichiri, et al., 1985, "Needle–Type Glucose Sensor For Wearable Artificial Endocrine Pancreas," *Implantable Sensors for Closed–Looped Prosthetic Systems,* Chapter 15: p. 197–210.
Schichiri, et al., 1986, "Telemetry Glucose Monitoring Device With Needle–Type Glucose Sensor: A Useful Tool For Blood Glucose Monitoring In Diabetic Individuals," *Diabetes Care,* vol. 19, No. 3: p. 298–301.
Shults, et al., 1994, "A Telemetry–Instrumentation System for Monitoring Multiple Subcutaneously Implanted Glucose Sensors," *IEE Transactions On Biomedical Engineering,* vol. 14, No. 10: p. 937–942.
Thompson et al., 1986, "In Vivo Probes: Problems And Perspectives," *Clinical Biochemistry,* vol. 19: p. 255–261.
Updike, et al., 1997, "Principles Of Long–Term Fully Implanted Sensors With Emphasis On Radiotelmetric Monitoring Of Blood Glucose From Inside A Subcutaneous Foreign Body Capsule (FBC)," *Biosensors In The Body: Continuous In Vivo Monitoring,* Chapter 4: p. 117–137.
Velho, et al., 1989, "Strategies For Calibrating A Subcutaneous Glucose Sensor," *Biomed.Biochim. Acia,* vol. 28, No. 11/12: p. 957–964.
Wilson, et al., 1992, "Progress Toward The Development Of An Implantable Sensor For Glucose," *Clinical Chemistry,* vol. 38, No. 9: p. 1613–1617.
Mauras et al., "Lack of accuracy of continuous glucose sensors in healthy, nondiabetic children: results of the Diabetes Research in Children Network (DirecNet) accuracy study," *J Pediatr.* Jun. 2004;144(6):770–5.
Scheller et al., "Second Generation Biosensors," *Biosens Bioelectron.* 1991;6(3):245–53.
von Woedtke et al., "In Situ Calibration of Implanted Electrochemical Glucose Sensors," *Biomed Biochim Acta,* 48 (1989) 11/12, pp. 943–952.
Armour et al., "Application of Chronic Intravascular Blood Glucose Sensor in Dogs," Diabetes, vol. 39, Dec. 1990, pp. 1519–1526.
Gregg et al., "Cross–linked Redox Gels Containing Glucose Oxidase for Amperometric Biosensor Applications," Anal. Chem., 1990, 62, 258–263.
Heller, "Electrical Connection of Enzyme Redox Centers to Electrodes," J. Phys. Chem., 1992, 96, 3579–3587.
McKean et al., "A Telemetry–Instrumentation System for Chronically Implanted Glucose and Oxygen Sensors," IEEE Transactions on Biomedical Engineering, vol. 35, No. 7, Jul. 1988.

Reusch et al., "Special Topics: Organometallic Compounds," Virtual Textbook of Organic Chemistry, pp. 11–12 (1999, latest revision 2004).
Shichiri et al., "Wearable Artificial Endocrine Pancreas with Needle–Type Glucose Sensor," The Lancet, 1129–1131 (1982).
Shichiri et al. "In Vivo Chararacteristics of Needle–Type Glucose Sensor—Measurements of Subcutaneous Glucose Concentrations in Human Volunteers," Horm. Metab. Res. Suppl., 20:17–20 (1988).
Shichiri et al., "Telemetry Glucose Monitoring Device With Needle–Type Glucose Sensor: A Useful Tool for Blood Glucose Monitoring in Diabetic Individuals," Diabetes Care, vol. 9, No. 3, May–Jun. 1986, pp. 298–301.
Shults et al., "A Telemetry–Instrumentation System for Monitoring Multiple Subcutaneously Implanted Glucose Sensors," IEEE Transactions on Biomedical Engineering, vol. 41, No. 10, Oct. 1994.
Sternberg et al., "Study and Development of Multilayer Needle–Type Enzyme–based Glucose Microsensors," Biosensors, 4 (1988) 27–40.
Thompson et al., "In Vivo Probes: Problems and Perspectives," Clinical Biochemistry, vol. 9, Oct. 1986, pp. 255–261.
Updike et al., Principles of Long–term Fully Implanted Sensors with Emphasis on Radiotelemetric Monitoring of Blood Glucose from inside a Subcutaneous Foreign Body Capsule (FBC), ed. Fraser, "Biosensors in the Body," 1997.
Velho et al., "Strategies for Calibrating a Subcutaneous Glucose Sensor," Biomed Biochim. Acta., 48 (1989) 11/12, 957–964.
GJ Kemp, "Theoretical Aspects of One–Point Calibration," *Clinical Chemistry,* 30/7 1163–1167 (1984).
Graham, "Poly(ethylene Oxide) and Related Hydrogels," *Hydrogels in Medicine and Pharmacy,* Chapter 4, CRC Press, 1987.
Hamilton Needle Gauge Index, www.hamiltoncompany.com, undated.
Interview Summary, U.S. Appl. No. 90/007,903 of U.S. Patent No. 6,565,509, U.S. Patent & Trademark Office, Alexandria, VA, Dated Oct. 16, 2008.
Response to Final Office Action, U.S. Appl. No. 90/007,903 of U.S. Patent No. 6,565,509, Baker Botts, LLP, New York, NY, Walter Egbert, Dated Oct. 20, 2008.
Advisory Action, U.S. Appl. No. 90/007,903 of U.S. Patent No. 6,565,509, U.S. Patent & Trademark Office, Alexandria, VA, Dated Nov. 21, 2008.
Order Denying Request for Reexamination, U.S. Appl. No. 90/009,279 of U.S. Patent No. 6,565,509, U.S. Patent & Trademark Office, Alexandria, VA, Dated Dec. 1, 2008.
Final Office Action, U.S. Appl. No. 90/007,910 of U.S. Patent No. 6,175,752, U.S. Patent & Trademark Office, Alexandria, VA, Dated Oct. 1, 2008.
Response to Final Office Action, U.S. Appl. No. 90/007,910 of U.S. Patent No. 6,175,752, Baker Botts, LLP, New York, NY, Walter Egbert, Dated Nov. 2, 2008.
Order Denying Request for Reexamination, U.S. Appl. No. 90/009,910 of U.S. Patent No. 6,175,752, U.S. Patent & Trademark Office, Alexandria, VA, Dated Dec. 1, 2008.
Office Action, U.S. Appl. No. 90/009,104 of U.S. Patent No. 6,990,366, U.S. Patent & Trademark Office, Alexandria, VA, Dated Oct. 16, 2008.
American Heritage Dictionary, 4th ed., Houghton Mifflin Company, 2000, p. 782.

Wiley Electrical and Electronics Engineering Dictionary, John Wiley & Sons, Inc. (2004), pp. 141, 142, 548, 549.

Pickup et al., "Responses and calibration of amperometric glucose sensors implanted in the subcutaneous tissue of man," Acta Diabetol. 30:143–148 (1993).

Aussedat et al., "A User–Friendly Method for Calibrating a Subcutaneous Glucose Sensor–Based Hypoglycaeemic Alarm," Biosensors & Bioelectronics, vol. 12, No. 11, pp. 1061–1071 (1997).

U.S. Appl. No. 12/210,122, filed Sep. 12, 2008 to James Say, et al.

U.S. Appl. No. 12/245,618, filed Oct. 3, 2008 to James Say, et al.

U.S. Appl. No. 12/249,644, filed Oct. 10, 2008 to James Say, et al.

U.S. Appl. No. 12/249,879, filed Oct. 10, 2008 to James Say, et al.

U.S. Appl. No. 09/447,227, Shults.

U.S. Appl. No. 11/737,671, Wolpert, et al.

U.S. Appl. No. 11/766,747, Say, et al.

U.S. Appl. No. 11/849,200, Peyser, et al.

U.S. Appl. No. 11/928,574, Heller, et al.

U.S. Appl. No. 11/928,668, Heller, et al.

U.S. Appl. No. 11/928,743, Heller, et al.

U.S. Appl. No. 11/928,795, Heller, et al.

U.S. Appl. No. 11/928,891, Heller, et al.

U.S. Appl. No. 11/928,968, Heller, et al.

U.S. Appl. No. 11/941,078, Say, et al.

Abel, P. U., et al., "Biosensors for In Vivo Glucose Measurement: Can We Cross the Experimental Stage", Biosensors and Bioelectronics, vol. 17, 2002, pp. 1059–1070.

Abruna, H. D., et al., "Rectifying Interfaces Using Two–Layer Films of Electrochemically Polymerized Vinylpyridine and Vinylbipyridine Complexes of Ruthenium and Iron on Electrodes", Journal of the American Chemical Society, vol. 103, No. 1, 1981, pp. 1–5.

Albery, W. J., et al., "Amperometric Enzyme Electrodes Part II: Conducting Salts as Electrode Materials for the Oxidation of Glucose Oxidase", Journal of ElectroAnalytical Chemistry, vol. 194, 1985, pp. 223–235.

Albery, W. J., et al., "Amperometric Enzyme Electrodes", Philosophical Transactions of The Royal Society of London, vol. 316, 1987, pp. 107–119.

Alcock, S. J., et al., "Continuous Analyte Monitoring to Aid Clinical Practice", IEEE Engineering in Medicine and Biology Magazine, 1994, pp. 319–325.

Anderson, L. B., et al., "Thin–Layer Electrochemistry: Steady–State Methods of Studying Rate Processes", Journal of ElectroAnalytical Chemistry, vol. 10, 1965, pp. 295–305.

Asberg, P., et al., "Hydrogels of a Conducting Conjugated Polymer as 3–D Enzyme Electrode", Biosensors & Bioelectronics, vol. 19, 2003, pp. 199–207.

Atanasov, P., et al., "Biosensors for Continuous Glucose Monitoring", Biotechnology and Bioengineering, vol. 43, 1994, pp. 262–266.

Atanasov, P., et al., "Implantation of a Refillable Glucose Monitoring–Telemetry Device", Biosensors & Bioelectronics, vol. 12, No. 7, 1997, pp. 669–680.

Aussedat, B., et al., "A User–Friendly Method for Calibrating a Subcutaneous Glucose Sensor–Based Hypoglycaemic Alarm", Biosensors & Bioelectronics, vol. 12, No. 11, 1997, pp. 1061–1071.

Baker, D. A., et al., "Dynamic Concentration Challenges for Biosensor Characterization", Biosensors & Bioelectronics, vol. 8, 1993, pp. 433–441.

Baker, D. A., et al., "Dynamic Delay and Maximal Dynamic Error in Continuous Biosensors", Analytical Chemistry, vol. 68, No. 8, 1996, pp. 1292–1297.

Bani Amer, M. M., "An Accurate Amperometric Glucose Sensor Based Glucometer with Eliminated Cross–Sensitivity", Journal of Medical Engineering & Technology, vol. 26, No. 5, 2002, pp. 208–213.

Bard, A. J., et al., Electrochemical Methods, 1980, pp. 173–175.

Bartlett, P. N., et al., "Covalent Binding of Electron Relays to Glucose Oxidase", Journal of the Chemical Society, Chemical Communications, 1987, pp. 1603–1604.

Bartlett, P. N., et al., "Modification of Glucose Oxidase by Tetrathiafulvalene", Journal of the Chemical Society, Chemical Communications, 1990, pp. 1135–1136.

Bartlett, P. N., et al., "Strategies for the Development of Amperometric Enzyme Electrodes", Biosensors, vol. 3, 1987/88, pp. 359–379.

Beach, R. D., et al., "Subminiature Implantable Potentiostat and Modified Commercial Telemetry Device for Remote Glucose Monitoring", IEEE Transactions on Instrumentation and Measurement, vol. 28, No. 6, pp. 1239–1245.

Beech, W. A., "AX.25 Link Access Protocol for Amateur packet Radio", Tucson Amateur Packet Radio Corporation, 1998, pp. 1–133.

Bennion, N., et al., "Alternate Site Glucose Testing: A Crossover Design", Diabetes Technology & Therapeutics, vol. 4, No. 1, 2002, pp. 25–33.

Bindra, D. S., et al., "Design and in Vitro Studies of a Needle–Type Glucose Sensor for Subcutaneous Monitoring", Analytical Chemistry, vol. 63, No. 17, 1991, pp. 1692–1696.

Bindra, D. S., et al., "Pulsed Amperometric Detection of Glucose in Biological Fluids at a Surface–Modified Gold Electrode", Analytical Chemistry, vol. 61, No. 22, 1989, pp. 2566–2570.

Bisenberger, M., et al., "A Triple–Step Potential Waveform at Enzyme Multisensors with Thick–Film Gold Electrodes for Detection of Glucose and Sucrose", Sensors and Actuators B, vol. 28, 1995, pp. 181–189.

Bland, J. M., et al., "A Note on the Use of the Intraclass Correlation Coefficient in the Evaluation of Agreement Between Two Methods of Measurement", Computers in Biology and Medicine, vol. 20, No. 5, 1990, pp. 337–340.

Bland, J. M., et al., "Statistical Methods for Assessing Agreement Between Two Methods of Clinical Measurement", The Lancet, 1986, pp. 307–310.

Blank, T. B., et al., "Clinical Results From a Non–Invasive Blood Glucose Monitor", Optical Diagnostics and Sensing of Biological Fluids and Glucose and Cholesterol Monitoring II, Proceedings of SPIE, vol. 4624, 2002, pp. 1–10.

Bobbioni–Harsch, E., et al., "Lifespan of Subcutaneous Glucose Sensors and Their Performances During Dynamic Glycaemia in Rats", Journal of Biomedical Engineering, vol. 15, 1993, pp. 457–463.

Bode, B. W., "Clinical Utility of the Continuous Glucose Monitoring System", Diabetes Technology & Therapeutics, vol. 2, Sup. 1, 2000, pp. S35–S41.

Bode, B. W., "Continuous Glucose Monitoring Used to Adjust Diabetes Therapy Improves Glycosylated Hemoglobin: A Pilot Study", *Diabetes Research and Clinical Practice, vol. 46,* 1999, pp. 183–190.

Bode, B. W., "Using the Continuous Glucose Monitoring System to Improve the Management of Type 1 Diabetes", *Diabetes Technology & Therapeutics, vol. 2, Sup. 1,* 2000, pp. S43–S48.

Boedeker Plastics, Inc., "Polyethylene Specifications", *Web Page of Boedeker.com,* 2007, pp. 1–3.

Bolinder, J., et al., "Microdialysis Measurement of the Absolute Glucose Concentration in Subcutaneous Adipose Tissue Allowing Glucose Monitoring in Diabetic Patients", *Diabetologia, vol. 35,* 1992, pp. 1177–1180.

Bolinder, J., et al., "Self–Monitoring of Blood Glucose in Type 1 Diabetic Patients: Comparison with Continuous Microdialysis Measurements of Glucose in Subcutaneous Adipose Tissue During Ordinary Life Conditions", *Diabetes Care, vol. 20, No. 1,* 1997, pp. 64–70.

Bott, A. W., "A Comparison of Cyclic Voltammetry and Cyclic Staircase Voltammetry", *Current Separations, vol. 16, No. 1,* 1997, pp. 23–26.

Bott, A. W., "Electrochemical Methods for the Determination of Glucose", *Current Separations, vol. 17, No. 1,* 1998, pp. 25–31.

Bowman, L., et al., "The Packaging of Implantable Integrated Sensors", *IEEE Transactions on Biomedical Engineering, vol. 33, No. 2,* 1986, pp. 248–255.

Brandt, J., et al., "Covalent Attachment of Proteins to Polysaccharide Carriers by Means of Benzoquinone", *Biochimica et Biophysica Acta, vol. 386,* 1975, pp. 196–202.

Brauker, J., et al., "Sustained Expression of High Levels of Human Factor IX from Human Cells Implanted Within an Immunoisolation Device into Athymic Rodents", *Human Gene Therapy, vol. 9, No. 6,* 1998, pp. 879–888.

Bremer, T. M., et al., "Benchmark Data from the Literature for Evaluation of New Glucose Sensing Technologies", *Diabetes Technology & Therapeutics, vol. 3, No. 3,* 2001, pp. 409–418.

Bremer, T., et al., "Is Blood Glucose Predictable from Previous Values?", *Diabetes, vol. 48,* 1999, pp. 445–451.

Brownlee, M., et al., "A Glucose–Controlled Insulin–Delivery System: Semisynthetic Insulin Bound to Lectin", *Science, vol. 206,* 1979, 1190–1191.

Cai, Q., et al., "A Wireless, Remove Query Glucose Biosensor Based on a pH–Sensitive Polymer", *Analytical Chemistry, vol. 76, No. 14,* 2004, pp. 4038–4043.

Cass, A. E., et al., "Ferricinum Ion As An Electron Acceptor for Oxido–Reductases", *Journal of ElectroAnalytical Chemistry, vol. 190,* 1985, pp. 117–127.

Cass, A. E., et al., "Ferrocene–Medicated Enzyme Electrode for Amperometric Determination of Glucose", *Analytical Chemistry, vol. 56, No. 4,* 1984, pp. 667–671.

Castner, J. F., et al., "Mass Transport and Reaction Kinetic Parameters Determined Electrochemically for Immobilized Glucose Oxidase", *Biochemistry, vol. 23 No. 10,* 1984, 2203–2210.

Chen, J. C., et al., "A Comparison of MAC Protocols for Wireless Local Networks Based on battery Power Consumption", *IEEE,* 1998, pp. 150–157.

Chen, T., et al., "Defining the Period of Recovery of the Glucose Concentration After Its Local Perturbation by the Implantation of a Miniature Sensor", *Clinical Chemistry and Laboratory Medicine, vol. 40, No. 8,* 2002, pp. 486–489.

Chia, C. W., et al., "Glucose Sensors: Toward Closed Loop Insulin Delivery", *Endocrinology and Metabolism Clinics of North America, vol. 33,* 2004, pp. 175–195.

Choleau, C., et al., "Calibration of a Subcutaneous Amperometric Glucose Sensor Implanted for 7 Days in Diabetic Patients Part 2: Superiority of the One–Point Calibration Method", *Biosensors and Bioelectronics, vol. 17,* 2002, pp. 647–654.

Choleau, C., et al., "Calibration of a Subcutaneous Amperometric Glucose Sensor Part 1: Effect of Measurement Uncertainties on the Determination of Sensor Sensitivity and Background Current", *Biosensors and Bioelectronics, vol. 17,* 2002, pp. 641–646.

Claremont, D. J., et al., "Biosensors for Continuous In Vivo Glucose Monitoring", *Proceedings of the Annual International Conference of the IEEE Engineering in Medicine and Biology Society, vol. 10,* 1988.

Clark Jr., L. C., et al., "Differential Anodic Enzyme Polarography for the Measurement of Glucose", *Oxygen Transport to Tissue: Instrumentation, Methods, and Physiology,* 1973, pp. 127–133.

Clark Jr., L. C., et al., "Electrode Systems for Continuous Monitoring in Cardiovascular Surgery", *Annals New York Academy of Sciences,* 1962, pp. 29–45.

Clark Jr., L. C., et al., "Long–term Stability of Electroenzymatic Glucose Sensors Implanted in Mice", *American Society of Artificial Internal Organs Transactions, vol. XXXIV,* 1988, pp. 259–265.

Clarke, W. L., et al., "Evaluating Clinical Accuracy of Systems for Self–Monitoring of Blood Glucose", *Diabetes Care, vol. 10, No. 5,* 1987, pp. 622–628.

Complaint, "*Abbott Diabetes Care, Inc.* v. Dexcom, Inc.", filed Aug. 11, 2005.

Complaint, Amended, "*Abbott Diabetes Care, Inc.* v. Dexcom, Inc.", filed Jun. 27, 2006.

Cox, D. J., et al., "Accuracy of Perceiving Blood Glucose in IDDM", *Diabetes Care, vol. 8, No. 6,* 1985, pp. 529–536.

Csoregi, E., et al., "Amperometric Microbiosensors for Detection of Hydrogen Peroxide and Glucose Based on Peroxidase–Modified Carbon Fibers", *Electroanalysis, vol. 6,* 1994, pp. 925–933.

Csoregi, E., et al., "Design and Optimization of a Selective Subcutaneously Implantable Glucose Electrode Based on 'Wired' Glucose Oxidase", *Analytical Chemistry, vol. 67, No. 7,* 1995, pp. 1240–1244.

Csoregi, E., et al., "Design, Characterization, and One–Point in Vivo Calibration of a Subcutaneously Implantable Glucose Electrode", *Analytical Chemistry, vol. 66, No. 19,* 1994, pp. 3131–3138.

Csoregi, E., et al., "On–Line Glucose Monitoring by Using Microdialysis Sampling and Amperometric Detection Based on 'Wired' Glucose Oxidase in Carbon Paste", *Mikrochimica Acta, vol. 121,* 1995, pp. 31–40.

D'Arrigo, G., et al., "Porous–Si Based Bio Reactors for Glucose Monitoring and Drugs Production", *Proceedings of SPIE: Microfluids, BioMEMS, and Medical Microsystems, vol. 4982,* 2003, pp. 178–184.

Davis, G., "Electrochemical Techniques for the Development of Amperometric Biosensors", *Biosensors, vol. 1,* 1985, pp. 161–178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry, vol. 91, No. 6,* 1987, pp. 1285–1289.

Degani, Y., et al., "Direct Electrical Communication Between Chemically Modified Enzymes and Metal Electrodes. 2. Methods for Bonding Electron–Transfer Relays to Glucose Oxidase and D–Amino–Acid Oxidase", *Journal of the American Chemical Society, vol. 110, No. 8,* 1988, pp. 2615–2620.

Degani, Y., et al., "Electrical Communication Between Redox Centers of Glucose Oxidase and Electrodes via Electrostatically Bound Redox Polymers", *Journal of the American Chemical Society, vol. 111,* 1989, pp. 2357–2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society, vol. 103,* 1981, pp. 4727–4737.

Dicks, J. M., et al., "Ferrocene Modified Polypyrrole with Immobilised Glucose Oxidase and its Application in Amperometric Glucose Microbiosensors", *Annales de Biologie Clinique, vol. 47,* 1989, pp. 607–619.

Dixon, B. M., et al., "Characterization In Vitro and In Vivo of the Oxygen Dependence of an Enzyme/Polymer Biosensors for Monitoring Brain Glucose", *Journal of Neuroscience Methods, vol. 119,* 2002, pp. 135–142.

Ellis, C. D., et al., "Selectivity and Directed Charge Transfer through an Electroactive Metallopolymer Film", *Journal of the American Chemical Society, vol. 103, No. 25,* 1981, pp. 7480–7483.

El–Sa'ad, L., et al., "Moisture Absorption by Epoxy Resins: The Reverse Thermal Effect", *Journal of Materials Science, vol. 25, No. 8,* 1990, pp. 3577–3582.

Engstrom, R. C., "Electrochemical Pretreatment of Glassy Carbon Electrodes", *Analytical Chemistry, vol. 54, No. 13,* 1982, pp. 2310–2314.

Engstrom, R. C., "Characterization of Electrochemically Pretreated Glassy Carbon Electrodes", *Analytical Chemistry, vol. 56, No. 2,* 1984, pp. 136–141.

Ernst, H. et al., "Reliable Glucose Monitoring Through the Use of Microsystem Technology", *Analytical and Bioanalytical Chemistry, vol. 373,* 2002, pp. 758–761.

Fare, T. L., et al., "Functional Characterization of a Conducting Polymer–Based Immunoassay System", *Biosensors & Bioelectronics, vol. 13, No. 3–4,* 1998, pp. 459–470.

Feldman, B., et al., "A Continuous Glucose Sensor Based on Wired Enzyme™ Technology—Results from a 3–Day Trial in Patients with Type 1 Diabetes", *Diabetes Technology & Therapeutics, vol. 5, No. 5,* 2003, pp. 769–779.

Feldman, B., et al., "Correlation of Glucose Concentrations in Interstitial Fluid Venous Blood During Periods of Rapid Glucose Change", *Abbott Diabetes Care, Inc. Freestyle Navigator Continuous Glucose Monitor Pamphlet.*

Feldman, B., et al., "Electron Transfer Kinetics at Redox Polymer/Solution Interfaces Using Microelectrodes and Twin Electrode Thin Layer Cells", *Journal of ElectroAnalytical Chemistry, vol. 194,* 1985, pp. 63–81.

Fischer, H., et al., "Intramolecular Electron Transfer Medicated by 4,4'–Bypyridine and Related Bridging Groups", *Journal of the American Chemical Society, vol. 98, No. 18,* 1976, pp. 5512–5517.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1, vol. 82,* 1986, pp. 1259–1264.

Foulds, N. C., et al., "Immobilization of Glucose Oxidase in Ferrocene–Modified Pyrrole Polymers", *Analytical Chemistry, vol. 60, No. 22,* 1988, pp. 2473–2478.

Frew, J. E., et al., "Electron–Transfer Biosensors", *Philosophical Transactions of The Royal Society of London, vol. 316,* 1987, pp. 95–106.

Frohnauer, M. K., et al., "Graphical Human Insulin Time–Activity Profiles Using Standardized Definitions", *Diabetes Technology & Therapeutics, vol. 3, No. 3,* 2001, pp. 419–429.

Frost, M. C., et al., "Implantable Chemical Sensors for Real–Time Clinical Monitoring: Progress and Challenges", *Current Opinion in Chemical Biology, vol. 6,* 2002, pp. 633–641.

Garg, S. K., et al., "Correlation of Fingerstick Blood Glucose Measurements with GlucoWatch Biographer Glucose Results in Young Subjects with Type 1 Diabetes", *Diabetes Care, vol. 22, No. 10,* 1999, pp. 1708–1714.

Garg, S. K., et al., "Improved Glucose Excursions Using an Implantable Real–Time Continuous Glucose Sensor in Adults with Type 1 Diabetes", *Diabetes Care, vol. 27, No. 3,* 2004, pp. 734–738.

Geller, R. L., et al., "Use of an Immunoisolation Device for Cell Transplantation and Tumor Immunotherapy", *Annals of the New York Academy of Sciences, vol. 831,* 1997, pp. 438–451.

Gerritsen, M., "Problems Associated with Subcutaneously Implanted Glucose Sensors", *Diabetes Care, vol. 23, No. 2,* 2000, pp. 143–145.

Gerritsen, M., "Influence of Inflammatory Cells and Serum on the Performance of Implantable Glucose Sensors", *Journal of Biomedical materials Research, vol. 54,* 2001, pp. 69–75.

Gerritsen, M., "Performance of Subcutaneously Implanted glucose Sensors for Continuous Monitoring", *The Netherlands Journal of Medicine, vol. 54,* 1999, pp. 167–179.

Gilligan, B. J., et al., "Evaluation of a Subcutaneous Glucose Sensor Out to 3 Months in a Dog Model", *Diabetes Care, vol. 17, No. 8,* 1994, pp. 882–887.

Gilligan, B. J., et al., "Feasibility of Continuous Long–Term Glucose Monitoring from a Subcutaneous Glucose Sensor in Humans", *Diabetes Technology & Therapeutics, vol. 6, No. 3,* 2004, pp. 378–386.

Gorton, L., et al., "Selective Detection in Flow Analysis Based on the Combination of Immobilized Enzymes and Chemically Modified Electrodes", *Analytica Chimica Acta, vol. 250,* 1991, pp. 203–248.

Gough, D. A., et al., "Immobilized Glucose Oxidase in Implantable Glucose Sensor Technology", *Diabetes Technology & Therapeutics, vol. 2, No. 3,* 2000, pp. 377–380.

Grant, R., et al., *Grant & Hackh's Chemical Dictionary,* 1987, pp. 88, 89, 389, 390, 398.

Gregg, B. A., et al., "Cross–Linked Redox Gels Containing Glucose Oxidase for Amperometric Biosensor Applications", *Analytical Chemistry, vol. 62, No. 3,* 1990, pp. 258–263.

Gregg, B. A., et al., "Redox Polymer Films Containing Enzymes. 1. A Redox–Conducting Epoxy Cement: Synthesis, Characterization, and Electrocatalytic Oxidation of Hydroquinone", *Journal of Physical Chemistry, vol. 95, No. 15,* 1991, 5970–5975.

Gross, T. M., et al., "Efficacy and Reliability of the Continuous Glucose Monitoring System", *Diabetes Technology & Therapeutics, vol. 2, Sup. 1,* 2000, pp. S19–S26.

Gross, T. M., et al., "Performance Evaluation of the MiniMed® Continuous Glucose Monitoring System During Patient Home Use", *Diabetes Technology & Therapeutics, vol. 2, No. 2,* 2000, pp. 49–56.

Hale, P. D., et al., "A New Class of Amperometric Biosensor Incorporating a Polymeric Electron–Transfer Mediator", *Journal of the American Chemical Society, vol. 111, No. 9,* 1989, pp. 3482–3484.

Hall, S. B., et al., "Electrochemical Oxidation of Hydrogen Peroxide at Platinum Electrodes: Part I: An Absorption–Controlled Mechanism", *Electrochimica Acta, vol. 43, No. 5–6,* 1998, pp. 579–588.

Hall, S. B., et al., "Electrochemical Oxidation of Hydrogen Peroxide at Platinum Electrodes: Part II: Effect of Potential", *Electrochimica Acta, vol. 43, No. 14–15,* 1998, 2015–2024.

Hall, S. B., et al., "Electrochemical Oxidation of Hydrogen Peroxide at Platinum Electrodes: Part III: Effect of Temperature", *Electrochimica Acta, vol. 44,* 1999, pp. 2455–2462.

Hall, S. B., et al., "Electrochemical Oxidation of Hydrogen Peroxide at Platinum Electrodes: Part IV: Phosphate Buffer Dependence", *Electrochimica Acta, vol. 44,* 1999, pp. 4573–4582.

Hall, S. B., et al., "Electrochemical Oxidation of Hydrogen Peroxide at Platinum Electrodes: Part V: Inhibition By Chloride", *Electrochimica Acta, vol. 45,* 2000, pp. 3573–3579.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry, vol. 60, No. 19,* 1988, pp. 2002–2007.

Hawkridge, F. M., et al., "Indirect Coulometric Titration of Biological Electron Transport Components", *Analytical Chemistry, vol. 45, No. 7,* 1973, pp. 1021–1027.

Heise, T. et al., "Hypoglycemia Warning Signal and Glucose Sensors: Requirements and Concepts", *Diabetes Technology & Therapeutics, vol. 5, No. 4,* 2003, pp. 563–571.

Heller, A., "Electrical Connection Enzyme Redox Centers to Electrodes", *Journal of Physical Chemistry, vol. 96, No. 9,* 1990, pp. 3579–3587.

Heller, A., "Electrical Wiring of Redox Enzymes", *Accounts of Chemical Research vol. 23, No. 5,* 1990, 128–134.

Heller, A., "Implanted Electrochemical Glucose Sensors for the Management of Diabetes", *Annual Review of Biomedical Engineering, vol. 1,* 1999, pp. 153–175.

Heller, A., "Plugging Metal Connectors into Enzymes", *Nature Biotechnology, vol. 21, No. 6,* 2003, pp. 631–632.

Heller, A., et al., "Amperometric Biosensors Based on Three–Dimensional Hydrogel–Forming Epoxy Networks", *Sensors and Actuators B, vol. 13–14,* 1993, pp. 180–183.

Hitchman, M. L., "Measurement of Dissolved Oxygen: Chapter 3: Principles of Voltammetry", *Chemical Analysis, vol. 49,* 1978, pp. 34–123.

Hrapovic, S. et al., "Picoamperometric Detection of Glucose at Ultrasmall Platinum–Based Biosensors: Preparation and Characterization", *Analytical Chemistry, vol. 75, No. 14,* 2003, pp. 3308–3315.

Huang, C. J., et al., "Electrochemical Generation of Oxygen", *Electrochemistry Research laboratory,* 1972, pp. 1–115.

Iannniello, R. M., et al., "Differential Pulse Voltammetric Study of Direct Electron Transfer in Glucose Oxidase Chemically Modified Graphite Electrodes", *Analytical Chemistry, vol. 54, No. 7,* 1982, pp. 1098–1101.

Ianniello, R. M., et al., "Immobilized Enzyme Chemically Modified Electrode as an Amperometric Sensor", *Analytical Chemistry, vol. 53, No. 13,* 1981, pp. 2090–2095.

Ikeda, T., et al., "Glucose Oxidase–Immobilized Benzoquinone–Carbon Paste Electrode as a Glucose Sensor", *Agricultural and Biological Chemistry, vol. 49, No. 2,* 1985, pp. 541–543.

Ikeda, T., et al., "Kinetics of Outer–Sphere Electron Transfers Between Metal Complexes in Solutions and Polymeric Films on Modified Electrodes", *Journal of the American Chemical Society, vol. 103, No. 25,* 1981, pp. 7422–7425.

Ishikawa, M., et al., "Initial Evaluation of a 290–μm Diameter Subcutaneous Glucose Sensor: Glucose Monitoring with a Biocompatible, Flexible–Wire, Enzyme–Based Amperometric Microsensor in Diabetic and Nondiabetic Humans", *Journal of Diabetes and Its Complications, vol. 12,* 1998, pp. 295–301.

Jablecki, M., et al., "Simulations of the Frequency Response of Implantable Glucose Sensors", *Analytical Chemistry, vol. 72, No. 8,* 2000, pp. 1853–1859.

Jaremko, J., et al., "Advances Toward the Implantable Artificial Pancreas for Treatment of Diabetes", *Diabetes Care, vol. 21, No. 3,* 1998, pp. 444–450.

Jensen, M. B., et al., "Fast Wave Forms for Pulsed Electrochemical Detection of Glucose by Incorporation of Reductive Desorption of Oxidation Products", *Analytical Chemistry, vol. 69, No. 9,* 1997, pp. 1776–1781.

Jeutter, D. C., "A Transcutaneous Implanted Battery Recharging and Biotelemeter Power Switching System", *IEEE Transactions on Biomedical Engineering, vol. 29, No. 5,* 1982, pp. 314–321.

Johnson, J. M., et al., "Potential–Dependent Enzymatic Activity in an Enzyme Thin–Layer Cell", *Analytical Chemistry, vol. 54, No. 8,* 1982, pp. 1377–1383.

Johnson, K. W., "Reproducible Electrodeposition of Biomolecules for the Fabrication of Miniature Electroenzymatic Biosensors", *Sensors and Actuators B, vol. 5,* 1991, pp. 85–89.

Johnson, P. C., "Peripheral Circulation", *John Wiley & Sons,* 1978, pp. 198.

Jonsson, G., et al., "An Amperometric Glucose Sensor Made by Modification of a Graphite Electrode Surface With Immobilized Glucose Oxidase and Adsorbed Mediator", *Biosensors, vol. 1,* 1985, pp. 355–368.

Josowicz, M., et al., "Electrochemical Pretreatment of Thin Film Platinum Electrodes", *Journal of the Electrochemical Society, vol. 135 No. 1,* 1988, pp. 112–115.

Jovanovic, L., "The Role of Continuous Glucose Monitoring in Gestational Diabetes Mellitus", *Diabetes Technology & Therapeutics, vol. 2, Sup. 1,* 2000, pp. S67–S71.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care, vol. 24, No. 7,* 2001, pp. 1303–1304.

Kang, S. K., et al., "In Vitro and Short–Term In Vivo Characteristics of a Kel–F Thin Film Modified Glucose Sensor", *Analytical Sciences, vol. 19,* 2003, pp. 1481–1486.

Kaplan, S. M., "Wiley Electrical and Electronics Engineering Dictionary", *IEEE Press,* 2004, pp. 141, 142, 548, 549.

Kargol, M., et al., "Studies on the Structural Properties of Porous Membranes: Measurement of Linear Dimensions of Solutes", *Biophysical Chemistry, vol. 91,* 2001, pp. 263–271.

Katakis, I., et al., "Electrostatic Control of the Electron Transfer Enabling Binding of Recombinant Glucose Oxidase and Redox Polyelectrolytes", *Journal of the American Chemical Society, vol. 116, No. 8,* 1994, pp. 3617–3618.

Katakis, I., et al., "L–α–Glycerophosphate and L–Lactate Electrodes Based on the Electrochemical 'Wiring' of Oxidases", *Analytical Chemistry, vol. 64, No. 9,* 1992, pp. 1008–1013.

Kaufman, F. R., et al., "Role of the Continuous Glucose Monitoring System in Pediatric Patients", *Diabetes Technology & Therapeutics, vol. 2, Sup. 1,* 2000, pp. S49–S52.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/+}$", *Journal of the Chemical Society, Faraday Transactions, vol. 92, No. 20,* 1996, pp. 4131–4136.

Kerner, W., "Implantable Glucose Sensors: Present Status and Future Developments", *Experimental and Clinical Endocrinology & Diabetes, vol. 109, Supplement 2,* 2001, pp. S341–S346.

Koschinsky, T., et al., "New Approach to Technical and Clinical Evaluation of Devices for Self–Monitoring of Blood Glucose", *Diabetes Care, vol. 11, No. 9,* 1988, pp. 619–629.

Koschinsky, T., et al., "Sensors for Glucose Monitoring: Technical and Clinical Aspects", *Diabetes Metabolism Research and Reviews, vol. 17,* 2001, pp. 113–123.

Koudelka, M., et al., "In–Vivo Behaviour of Hypodermically Implanted Microfabricated Glucose Sensors", *Biosensors & Bioelectronics, vol. 6,* 1991, pp. 31–36.

Kovatchev, B. P., et al., "Evaluating the Accuracy of Continuous Glucose–Monitoring Sensors", *Diabetes Care, vol. 27, No. 8,* 2004, pp. 1922–1928.

Kraver, K. L., et al., "A Mixed–Signal Sensor Interface Microinstrument", *Sensors and Actuators A, vol. 91,* 2001, pp. 266–277.

Krouwer, J. S., "Setting Performance Goals and Evaluating Total Analytical error for Diagnostic Assays", *Clinical Chemistry, vol. 48, No. 6,* 2002, pp. 919–927.

Kruger, D., et al., "Psychological Motivation and Patient Education: A Role for Continuous Glucose Monitoring", *Diabetes Technology & Therapeutics, vol. 2, Sup. 1,* 2000, pp. S93–S97.

Kulys, J., et al., "Mediatorless Peroxidase Electrode and Praparation of Bienzyme Sensors", *Bioelectrochemistry and Bioenergetics, vol. 24,* 1990, pp. 305–311.

Kurnik, R. T., et al., "Application of the Mixture of Experts Algorithm for Signal Processing in a Noninvasive Glucose Monitoring System" *Sensors and Actuators B, vol. 60,* 1990, pp. 19–26.

Lacourse, W. R., et al., "Optimization of Waveforms for Pulsed Amperometric Detection of Carbohydrates Based on Pulsed Voltammetry", *Analytical Chemistry, vol. 65, No. 1,* 1993, pp. 50–55.

Lager, W., et al., "Implantable Electrocatalytic Glucose Sensor", *Hormone Metabolic Research, vol. 26,* 1994, pp. 526–530.

Lee, E., et al., "Effects of Pore Size, Void Volume, and Pore Connectivity on Tissue Responses to Porous Silicone Implants", *Transactions on the Twenty–Fifth Annual Meeting of the Society for Biomaterials, vol. 22,* 1999, pp. 171.

Lerner, H., et al., "An Implantable Electrochemical Glucose Sensor", *Annals of the New York Academy of Sciences, vol. 428,* 1984, pp. 263–278.

Leypoldt, J. K., et al., "Model of a Two–Substrate Enzyme Electrode for Glucose", *Analytical Chemistry, vol. 56, No. 14,* 1984, pp. 2896–2904.

Lindner, E., et al., "Flexible (Kapton–Based) Microsensor Arrays of High Stability for Cardiovascular Applications", *Journal of the Chemical Society, Faraday Transactions, vol. 89, No. 2,* 1993, pp. 361–367.

Liu, W., et al., "A Neuro–Stimulus Chip with Telemetry Unit for Retinal Prosthetic Device", *IEEE Journal of Solid–State Circuits, vol. 35, No. 10,* 2000, pp. 1487–1497.

Lortz, J., et al., "What is Bluetooth? We Explain The Newest Short–Range Connectivity Technology", *Smart Computing Learning Series, Wireless Computing, vol. 8, Issue 5,* 2002, pp. 72–74.

Luong, J. H. T., et al., "Solubilization of Multiwall Carbon Nanotubes by 3–Aminopropyltriethoxysilane Towards the Fabrication of Electrochemical Biosensors with Promoted Electron Transfer". *Electroanalysis, vol. 16, No. 1–2,* 2004, pp. 132–139.

Lynch, S. M., et al., "Estimation–Based Model Predictive Control of Blood Glucose in Type 1 Diabetics: A Simulation Study", *Proceedings of the IEEE 27th Annual Norhteast Bioengineering Conference,* 2001, pp. 79–80.

Lynn, P. A., "Recursive Digital Filters for Biological Signals", *Medical and Biological Engineering, vol. 9,* 1971, pp. 37–43.

Maidan, R., et al., "Elimination of Electrooxidizable Interfernat–Produced Currents in Amperometric Biosensors", *Analytical Chemistry, vol. 64, No. 23,* 1992, pp. 2889–2896.

Makale, M. T., et al., "Tissue Window Chamber System for Validation of Implanted Oxygen Sensors", *American Journal of Physiology: Heart and Circulatory Physiology, vol. 284,* 2003, pp. H2288–H2294.

Malin, S. F., et al., "Noninvasive Prediction of Glucose by Near–Infrared Diffuse Reflectance Spectroscopy", *Clinical Chemistry, vol. 45, No. 9,* 1999, pp. 1651–1658.

Mancy, K. H., et al., "A Galvanic Cell Oxygen Analyzer", *Journal of Electroanalytical Chemistry, vol. 4,* 1962, pp. 65–92.

Maran, A., et al., "Continuous Glucose Monitoring in Diabetic Patients", *Diabetes Care, vol. 25, No. 2,* 2002, pp. 347–352.

March, W. F., "Dealing with the Delay", *Diabetes Technology & Therapeutics, vol. 4, No. 1,* 2002, pp. 49–50.

Martin, R. F., "General Deming Regression for Estimating Systematic Bias and Its Confidence Interval in Method–Comparison Studies", *Clinical Chemistry, vol. 46, No. 1,* 2000, pp. 100–104.

Mastrototaro, J. J., "The MiniMed Continuous Glucose Monitoring System", *Diabetes Technology & Therapeutics*, vol. 2, Sup. 1, 2000, pp. S13–S18.

Mastrototaro, J. J., "An Electroenzymatic Glucose Sensor Fabricated on a Flexible Substrate", *Sensors and Actuators B*, vol. 5, 1991, pp. 139–144.

Mastrototaro, J. J., "Reproducibility of the Continuous Glucose Monitoring System Matches Previous Reports and the Intended Use of the Product" and "Response to Matrototaro and Gross", *Diabetes Care*, vol. 26, No. 1, 2003, pp. 256–257.

McCartney, L. J., et al., "Near–Infrared Fluorescence Lifetime Assay for Serum Glucose Based on Allophycocyanin–Labeled Concanavalin A", *Analytical Biochemistry*, vol. 292, 2001, pp. 216–221.

McGarraugh, G., et al., "Glucose Measurements Using Blood Extracted from the Forearm and the Finger", *TheraSense, Inc.*, 16 Pages.

McGarraugh, G., et al., "Physiological Influences on Off–Finger Glucose Testing", *Diabetes Technology & Therapeutics*, vol. 3, No. 3, 2001, pp. 367–376.

McGrath, M. J., et al., "The Use of Differential Measurements with a Glucose Biosensor for Interference Compensation During Glucose Determinations by Flow Injection Analysis", *Biosensors & Bioelectronics*, vol. 10, 1995, pp. 937–943.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25–29.

Memoli, A., et al., "A Comparison Between Different Immobilized Glucoseoxidase–Based Electrodes", *Jorunal of Pharmaceutical and Biomedical Analysis*, vol. 29, 2002, pp. 1045–1052.

Metzger, M., et al., "Reproducibility of Glucose Measurements Using the Glucose Sensor", *Diabetes Care*, vol. 25, No. 6, 2002, pp. 1185–1191.

Miller, K. M., et al., "Generation of ILI–like Activity in Response to Biomedical Polymer Implants: A Comparison of In Vitro and In Vivo Models", *Journal of Biomedical Materials Research*, vol. 23, 1989, pp. 1007–1026.

Miller, K. M., et al., "Human Monocyte/Macrophage Activation and Interleukin 1 Generation by Biomedical Polymers", *Journal of Biomedical Materials Research*, vol. 22, 1988, pp. 713–731.

Miller, K. M., et al., "In Vitro Stimulation of Fibroblast Activity by Factors Generated from Human Monocytes Activated by Biomedical Polymers", *Journal of Biomedical Materials Research*, vol. 23, 1989, pp. 911–930.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60–68.

Moatti–Sirat, D., et al., "Evaluating In Vitro and In Vivo the Interference of Ascorbate and Acetaminophen on Glucose Detection by a Needle–Type Glucose Sensor", *Biosensors & Bioelectronics*, vol. 7, 1992, pp. 345–352.

Moatti–Sirat, D., et al., "Reduction of Acetaminophen Interference in Glucose Sensors by a Composite Nafion Membrane: Demonstration in Rats and Man", *Diabetologia*, vol. 37, 1994, pp. 610–616.

Moatti–Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224–330.

Monsod, T. P., et al., "Do Sensor Glucose Levels Accurately Predict Plasma Glucose Concentrations During Hypoglycemia and Hyperinsulinemia?" *Diabetes Care*, vol. 25, No. 5, 2002, pp. 889–893.

Moussy, F., et al., "A Miniaturized Nafion–Based Glucose Sensor: In Vitro and In Vivo Evaluation in Dogs", *The International Journal of Artificial Organs*, vol. 17, No. 2, 1994, pp. 88–94.

Mowery, K. A., et al., "Preparation and Characterization of Hydrophobic Polymeric Films tht are Thromboresistant via Nitric Oxide Release", *Biomaterials*, vol. 21, 2000, pp. 9–21.

Nagy, G., et al., "A New Type of Enzyme Electrode: The Ascorbic Acid Eliminator Electrode", *Life Sciences*, vol. 31, No. 23, 1982, pp. 2611–2616.

Nakamura, S., et al., "Effect of Periodate Oxidation on the Structure and Properties of Glucose Oxidase", *Biochimica et Biophysica Acta.*, vol. 445, 1976, pp. 294–308.

Nam, Y. S., et al., "A Novel Fabrication Method of Macroporous Biodegradable Polymer Scaffolds Using Gas Foaming Salt as a Porogen Additive", *Journal of Biomedical Materials Research*, vol. 53, 2000, pp. 1–7.

Nappholz, T. A., "Programmers for Implants: A Need for Radical Change", $18^{th}$ *Annual International Conference of the IEEE Engineering in Medicine and Biology Society*, Amsterdam, 1996, pp. 1274–1275.

Narasimham, K., et al., "p–Benzoquinone Activation of Metal Oxide Electrodes for Attachment of Enzymes", *Enzyme and Microbial Technology*, vol. 7, 1985, pp. 283–286.

Neuburger, G. G., et al., "Pulsed Amperometric Detection of Carbohydrates at Gold Electrodes with a Two–Step Potential Waveform", *Analytical Chemistry*, vol. 59, No. 1, 1987, pp. 150–154.

Ohara, T. J., "Osmium Bipyridyl Redox Polymers Used in Enzyme Electrodes", *Platinum Metals Review*, vol. 39, No. 2, 1995, pp. 54–62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451–2457.

Ohara, T. J., et al., "Glucose Electrodes Based on Cross–Linked $[Os(bpy)_2Cl]^{+/2+}$ Complexed Poly(1–Vinylimidazole) Films", *Analytical Chemistry*, vol. 65, No. 23, 1993, pp. 3512–3517.

Okuda, J., et al., "Mutarotase Effect on Micro Determinations of D–Glucose and Its Anomers with β–D–Glucose Oxidase", *Analytical Biochemistry*, vol. 43, 1971, pp. 312–315.

Olievier, C. N., et al., "In Vivo Measurement of Carbon Dioxide Tension with a Miniature Electrodes", *Pflugers Archiv: European Journal of Physiology*, vol. 373, 1978, pp. 269–272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487–494.

Palleschi, G., et al., "A Study of Interferences in Glucose Measurements in Blood by Hydrogen Peroxide Based Glucose Probes", *Analytical Biochemistry, vol. 159,* 1986, pp. 114–121.

Palmisano, F., et al., "Simultaneous Monitoring of Glucose and Lactate by an Interference and Cross–Talk Free Dual Electrode Amperometric Biosensor Based on Electropolymerized Thin Films", *Biosensors & Bioelectronics, vol. 15,* 2000, pp. 531–539.

Pankratov, I., et al., "Sol–Gel Derived Renewable–Surface Biosensors", *Journal of ElectroAnalyrical Chemistry, vol. 393,* 1995, pp. 35–41.

Panteleon, A. E., et al., "The Role of the Independent Variable to Glucose Sensor Calibration", *Diabetes Technology & Therapeutics, vol. 5, No. 3,* 2003, pp. 401–410.

Parker, R. S., et al., "A Model–Based Algorithm for Blood Glucose Control in Type 1 Diabetic Patients", *IEEE Transactions on Biomedical Engineering, vol. 46, No. 2,* 1999, pp. 148–157.

Patel, H., et al., "Amperometric Glucose Sensors Based on Ferrocene Containing Polymeric Electron Transfer Systems—A Preliminary Report", *Biosensors and Bioelectronics, vol. 18,* 2003, pp. 1073–1076.

Pathak, C., et al., "Rapid Photopolymerization of Immunoprotective Gels in Contact with Cells and Tissue", *Journal of the American Chemical Society, vol. 114, No. 21,* 1992, pp. 8311–8312.

Pichert, J. W., et al., "Issues for the Coming Age of Continuous Glucose Monitoring", *The Diabetic Educator, vol. 26, No. 6,* 2000, pp. 969–980.

Pickup, J. C., et al., "Responses and Calibration of Amperometric Glucose Sensors Implanted in the Subcutaneous Tissue of Man", *Acta Diabetologica, vol. 30,* 1993, pp. 143–148.

Pickup, J., "Developing Glucose Sensors for In Vivo Use", *Tibtech, vol. 11,* 1993, pp. 285–291.

Pickup, J., et al., "In Vivo Molecular Sensing in Diabetes Mellitus: An Implantable Glucose Sensor with Direct Electron Transfer", *Diabetologica, vol. 32,* 1989, pp. 213–217.

Pickup, J. C., et al., "Potentially–Implantable, Amperometric Glucose Sensors with Mediated Electron Transfer: Improving the Operating Stability", *Biosensors, vol. 4,* 1989, pp. 109–119.

Pishko, M. V., et al., "Amperometric Glucose Microelectrodes Prepared Through Immobilization of Glucose Oxidase in Redox Hydrogels", *Analytical Chemistry, vol. 63, No. 20,* 1991, pp. 2268–2272.

Pitzer, K. R., et al., "Detection of Hypoglycemia with the GlucoWatch Biographer", *Diabetes Care, vol. 24, No. 5,* 2001, pp. 881–885.

Poirier, J. Y., et al., "Clinical and Statistical Evaluation of Self–Monitoring Blood Glucose Meters", *Diabetes Care, vol. 21, No. 11,* 1998, pp. 1919–1924.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia, vol. 36,* 1993, pp. 658–663.

Poitout, V., et al., "Calibration in Dogs of a Subcutaneous Miniaturized Glucose Sensor Using a Glucose Meter for Blood Glucose Determination", *Biosensors & Bioelectronics, vol. 7,* 1992, pp. 587–592.

Poitout, V., et al., "In Vitro and In Vivo Evaluation in Dogs of a Miniaturized Glucose Sensor", *ASAIO Transactions, vol. 37, No. 3,* 1991, pp. M298–M300.

Pollak, A., et al., "Enzyme Immobilization by Condensation Copolymerization into Cross–Linked Polyacrylamide Gels", *Journal of the American Chemical Society, vol. 102, No. 20,* 1980, pp. 6324–6336.

Postlethwaite, T. A., et al., "Interdigitated Array Electrode as an Alternative to the Rotated Ring—Disk Electrode for Determination of the Reaction Products of Dioxygen Reduction", *Analytical Chemistry, vol. 68, No. 17,* 1996, pp. 2951–2958.

Quinn, C. P., et al., "Biocompatible, Glucose–Permeable Hydrogel for In Situ Coating of Implantable Biosensors", *Biomaterials, vol. 18, No. 24,* 1997, pp. 1665–1670.

Quinn, C. A. P., et al., "Kinetics of Glucose Delivery to Subcutaneous Tissue in Rats Measured with 0.3–mm Amperometric Microsensors", *The American Physiological Society,* 1995, E155–E161.

Ratner, B. D., "Reducing Capsular Thickness and Enhancing Angeiogenesis Around Implant Drug Release Systems", *Journal of Controlled Release, vol. 78,* 2002, pp. 211–218.

Reach, G., "Which Threshold to Detect Hypoglycemia?", *Diabetes Care, vol. 24, No. 5,* 2001, pp. 803–804.

Reach, G., et al., "A Method of Evaluating In Vivo the Functional Characteristics of Glucose Sensors", *Biosensors 2,* 1986, pp. 211–220.

Reach, G., et al., "Can Continuous Glucose Monitoring Be Used for the Treatment of Diabetes?", *Analytical Chemistry, vol. 64, No. 6,* 1992, pp. 381–386.

Reach, G., et al., "Letters to the Editor: Re: Diabetes Technology & Therapeutics, 2000, 2:49–56", *Diabetes Technology & Therapeutics, vol. 3, No. 1,* 2001, pp. 129–131.

Rebrin, K., et al., "Automated Feedback Control of Subcutaneous Glucose Concentration in Diabetic Dogs", *Diabetologia, vol. 32,* 1989, pp. 573–576.

Rebrin, K., et al., "Subcutaneous Glucose Predicts Plasma Glucose Independent of Insulin: Implications for Continuous Monitoring", *The American Physiological Society,* 1999, pp. E561–E571.

Rhodes, R. K., et al., "Prediction of Pocket–Portable and Implantable Glucose Enzyme Electrode Performance from Combined Species Permeability and Digital Simulation Analysis", *Analytical Chemistry, vol. 66, No. 9,* 1994, pp. 1520–1529.

Rinken, T., et al., "Calibration of Glucose Biosensors By Using Pre–Study State Kinetic Data", *Biosensors & Bioelectronics, vol. 13,* 1998, pp. 801–807.

Roe, J. N., et al., "Bloodless Glucose Measurements", *Critical Review in Therapeutics Drug Carrier Systems, vol. 15, Issue 3,* 1998, pp. 199–241.

Sakakida, M., et al., "Ferrocene–Mediated Needle–Type Glucose Sensor Covered with Newly Designed Biocompatible Membrane", *Sensors and Actuators B, vol. 13–14,* 1993, pp. 319–322.

Salehi, C., et al., "A Telemetry–Instrumentation System for Long–Term Implantable Glucose and Oxygen Sensors", *Analytical Letters, vol. 29, No. 13,* 1996, pp. 2289–2308.

Samuels, G. J., et al., "An Electrode–Supported Oxidation Catalyst Based on Ruthenium (IV). pH 'Encapsulation' in a Polymer Film", *Journal of the American Chemical Society, vol. 103, No. 2,* 1981, pp. 307–312.

Sansen, W., et al., "A Smart Sensor for the Voltammetric Measurement of Oxygen or Glucose Concentrations", *Sensors and Actuators B1*, 1990, pp. 298–302.

Sansen, W., et al., "Chapter 12: Glucose Sensor with Telemetry System", *Implantable Sensors for Closed–Loop Prosthetic Systems*, 1985, pp. 167–175.

Sasso, S. V., et al., "Electropolymerized 1,2–Diaminobenzene as a Means to Prevent Interferences and Fouling and to Stabilize Immobilized Enzyme in Electrochemical Biosensors", *Analytical Chemistry*, vol. 62, No. 11, 1990, pp. 1111–1117.

Scheller, F., et al., "Enzyme Electrodes and Their Application", *Philosophical Transactions of The Royal Society of London B*, vol. 316, 1987, pp. 85–94.

Schmehl, R. H., et al., "The Effect of Redox Site Connection on the Rate of Mediated Oxidation of Solution Substrates by a Redox Copolymer Film", *Journal of ElectroAnalytical Chemistry*, vol. 152, 1983, pp. 97–109.

Schmidt, F. J., et al., "Glucose Concentration in Subcutaneous Extracellular Space", *Diabetes Care*, vol. 16, No. 5, 1993, pp. 695–700.

Schmidtke, D. W., et al., "Accuracy of the One–Point In Vivo Calibration of 'Wired' Glucose Oxidase Electrodes Implanted in Jugular Veins of Rats in Periods of Rapid Rise and Decline of the Glucose Concentration", *Analytical Chemistry*, vol. 70, No. 10, 1998, pp. 2149–2155.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294–299.

Schoemaker, M., et al., "The SCHMI System: Subcutaneous Continiuous Glucose Monitoring Based on Microdialysis Technique", *Diabetes Technology & Therapeutics*, vol. 5, No. 4, 2003, pp. 599–608.

Schwarz, M., et al., "Micro Implantable Visual Prostheses", *1st Annual International IEEE–EMBS Special Topic Conference on Microtechnologies in Medicine & Biology, Lyon, France*, 2000, pp. 461–465.

Selam, J. L., "Management of Diabetes with Glucose Sensors and Implantable Insulin Pumps: From the Dream of the 60s to the Realities of the 90s", *American Society for Artificial Internal Organs Journal*, 1997, pp. 137–142.

Service, R. F., "Can Sensors Make a Home in the Body?", *Science*, vol. 297, 2002, pp. 962–963.

Sieminski, A. L., et al., "Biomaterial–Microvasculature Interactions", *Biomaterials*, vol. 21, 2000, pp. 2233–2241.

Sittampalam, G., et al., "Surface–Modified Electrochemical Detector for Liquid Chromatography", *Analytical Chemistry*, vol. 55, No. 9, 1983, pp. 1608–1610.

Skyler, J. S., "The Economic Burden of Diabetes and the Benefits of Improved Glycenic Control: The Potential Role of a Continuous Glucose Monitoring System", *Diabetes Technology & Therapeutics*, vol. 2, Sup. 1, 2000, pp. S7–S12.

Soegijoko, S., et al., "External Artificial Pancreas: A New Control Unit Using Microprocessor", *Hormone and Metabolic Research Supplement Series*, vol. 12, 1982, pp. 165–169.

Sokolov, S., et al., "Metrological Opportunities of the Dynamic Mode of Operating an Enzyme Amperometric Biosensor", *Medical Engineering and Physics*, vol. 17, No. 6, 1995, pp. 471–476.

Sproule, B. A., et al., "Fuzzy Pharmacology: Theory and Applications", *Trends in Pharmacological Sciences* vol. 23, No. 9, 2002, pp. 412–417.

Sprules, S. D., et al., "Evaluation of a New Disposable Screen–Printed Sensor Strip for the Measurement of NADH and Its Modification to Produce a Lactate Biosensor Employing Microliter Volumes", *Electroanalysis*, vol. 8, No. 6, 1996, pp. 539–543.

Sriyudthsak, M., et al., "Enzyme–Epoxy Membrane Based Glucose Analyzing System and Medical Applications", *Biosensors & Bioelectronics*, vol. 11, No. 8, 1996, pp. 735–742.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27–31.

Sternberg, F., et al., "Calibration Problems of Subcutaneous Glucosensors when Applied 'In–Situ' in Man", *Hormone and Metabolic Research*, vol. 26, 1994, pp. 523–526.

Sternberg, F., et al., "Does Fall In Tissue Glucose Precede Fall In Blood Glucose?" *Diabetologia*, vol. 29, 1996, pp. 609–612.

Sternberg, R., et al., "Covalent Enzyme Coupling on Cellulose Acetate Membranes for Glucose Sensor Development", *Analytical Chemistry*, vol. 60, No. 24, 1988, pp. 2781–2786.

Sternberg, R., et al., "Study and Development of Multilayer Needle–Type Enzyme–Based Glucose Microsensors", *Biosensors*, vol. 4, 1988, pp. 27–40.

Street, J. O., et al., "A Note on Computing Robust Regression Estimates Via Interactively Reweighted Least Squares", *The American Statistician*, vol. 42, No. 2, 1988, pp. 152–154.

Suaning, G. J., et al., "CMOS Neurostimulation ASIC with 100 Channels, Scaleable Output, and Bidirectional Radio–Frequency Telemetry" *IEEE Transactions on Biomedical Engineering*, vol. 48, No. 2, 2001, pp. 248–260.

Suekane, M., "Immobilization of Glucose Isomerase", *Zettschrift fur Allgemeine Mikrobiologie*, vol. 22, No. 8, 1982, pp. 565–576.

Tajima, S., et al., "Simultaneous Determination of Glucose and 1,5–Anydroglucitol", *Chemical Abstracts*, vol. 111, No. 25, 1989, pp. 394.

Tamura, T., et al., "Preliminary Study of Continuous Glucose Monitoring with a Microdialysis Technique and a Null Method—a Numerical Analysis", *Frontiers Medical and Biological Engineering*, vol. 10, No. 2, 2000, pp. 147–156.

Tanenberg, R. J., et al., "Continuous Glucose Monitoring System: A New Approach to the Diagnosis of Diabetic Gastroparesis", *Diabetes Technology & Therapeutics*, vol. 2, Sup. 1, 2000, pp. S73–S80.

Tang, L., et al., "Fibrin(ogen) Mediates Acute Inflammatory Responses to Biomaterials", *Journal of Experimental Medicine*, vol. 178, 1993, pp. 2147–2156.

Tang, L., et al., "Inflammatory Responses to Biomaterials", *American Journal of Clinical Pathology*, vol. 103, No. 4, 1995, pp. 466–471.

Tang, L., et al., "Mast Cells Mediate Acute Inflammatory Responses to Implanted Biomaterials", *Proceedings of the National Academy of Sciences USA*, vol. 95, 1998, pp. 8841–8846.

Tang, L., et al., "Molecular Determinants of Acute Inflammatory Responses to Biomaterials", *Journal of Clinical Investigation*, vol. 97, No. 5, 1996, pp. 1329–1334.

Tang, Z., et al., "Data Transmission from an Implantable Biotelemetry by Load–Shift Keying Using Circuit Configuration Modulator", *IEEE Transactions on Biomedical Engineering, vol. 42, No. 5,* 1995, pp. 524–528.

Tarasevich, M. R., "Bioelectrocatalysis", *Comprehensive Treatise of Electrochemistry, vol. 10,* 1985, pp. 231–295.

Tatsuma, T., et al., "Enzyme Monolayer—and Bilayer–Modified Tin Oxide Electrodes for the Determination of Hydrogen Peroxide and Glucose", *Analytical Chemistry, vol. 61, No. 21,* 1989, pp. 2352–2355.

Taylor, C., et al., "'Wiring' of Glucose Oxidase Within a Hydrogel Made with Polyvinyl Imidazole Complexed with [(Os–4,4'–dimethoxy–2,2'–bipyridine)Cl]$^{+/2+}$", *Journal of ElectroAnalytical Chemistry, vol. 396,* 1995, pp. 511–515.

Thome–Duret, V., et al., "Continuous Glucose Monitoring in the Free–Moving Rat", *Metabolism, vol. 47, No. 7,* 1998, pp. 799–803.

Thome–Duret, V., et al., "Modification of the Sensitivity of Glucose Sensor Implanted into Subcutaneous Tissue", *Diabetes & Metabolism, vol. 22, No. 3,* 1996, pp. 174–178.

Tibell, A., et al., "Survival of Macroencapsulated Allogeneic Parathyroid Tissue One Year After Transplantation in Non-immunosuppressed Humans", *Cell Transplantation, vol. 10, No. 7,* 2001, pp. 591–599.

Tierney, M. J., "The GlucoWatch® Biographer: A Frequent, Automatic and Noninvasive Glucose Monitor", *Annals of Medicine, vol. 32,* 2000, pp. 632–641.

Tierney, M. J., et al., "Effect of Acetaminophen on the Accuracy of Glucose Measurements Obtained with the GlucoWatch Biographer", *Diabetes Technology & Therapeutics, vol. 2, No. 2,* 2000, pp. 199–207.

Tilbury, J. B., et al., "Receiver Operating Characteristic Analysis for Intelligent Medical Systems—A New Approach for Finding Confidence Intervals", *IEEE Transactions on Biomedical Engineering, vol. 47, No. 7,* 2000, pp. 952–963.

Trajanoski, Z., et al., "Neural Predictive Controller for Insulin Delivery Using the Subcutaneous Route", *IEEE Transactions on Biomedical Engineering, vol. 45, No. 9,* 1999, pp. 1122–1134.

Trecroci, D., "A Glimpse Into the Future: Continuous Monitoring of Glucose with a Microfiber", *Diabetes Interview,* 2002, pp. 42–43.

Trojanowicz, M., et al., "Enzyme Entrapped Polypyrrole Modified Electrode for Flow–Injection Determination of Glucose", *Biosensors & Bioelectronics, vol. 5,* 1990, pp. 149–156.

Turner, A., et al., "Diabetes Mellitus: Biosensors for Research and Management", *Biosensors, vol. 1,* 1985, pp. 85–115.

Turner, R. F., et al., "A Biocompatible Enzyme Electrode for Continuous in vivo Glucose Monitoring in Whole Blood", *Sensors and Actuators B, vol. 1,* 1990, pp. 561–564.

Tuzhi, P., et al., "Constant Potential Pretreatment of Carbon Fiber Electrodes for In Vivo Electrochemistry", *Analytical Letters, vol. 24, No. 6,* 1991, pp. 935–945.

U.S. Department of Health and Human Services, "Off–The–Shelf–Software Use in Medical Devices", *Guidance for Industry, FDA Reviewers and Compliance on,* 1999, pp. 1–26.

Umana, M., "Protein–Modified Electrochemically Active Biomaterial Surface", *U.S. Army Research Office, Analytical and Chemical Sciences Research Triangle Institute,* 1988, pp. 1–9.

Updike, S. J., et al., "A Subcutaneous Glucose Sensor with Improved Longevity, Dynamic Range, and Stability of Calibration", *Diabetes Care, vol. 23, No. 2,* 2000, pp. 208–214.

Updike, S. J., et al., "Continuous Glucose Monitor Based on an Immobilized Enzyme Electrode Detector", *The Journal of Laboratory and Clinical Medicine, vol. 93, No. 4,* 1979, pp. 518–527.

Updike, S. J., et al., "Enzymatic Glucose Sensors: Improved Long–Term Performance In Vitro and In Vivo", *American Society for Artificial Internal Organs Journal,* 1994, pp. 157–163.

Updike, S. J., et al., "Implanting the Glucose Enzyme Electrode: Problems, Progress, and Alternative Solutions", *Diabetes Care, vol. 5, No. 3,* 1982, pp. 207–212.

Updike, S. J., et al., "The Enzyme Electrode", *Nature, vol. 214,* 1967, pp. 986–988.

Urban, G., et al., "Miniaturized Thin–Film Biosensors Using Covalently Immobilized Glucose Oxidase", *Biosensors & Bioelectronics, vol. 6,* 1991, pp. 555–562.

Valdes, T. I., et al., "In Vitro and In Vivo Degradation of Glucose Oxidase Enzyme Used for an Implantable Glucose Biosensor", *Diabetes Technology & Therapeutics, vol. 2, No. 3,* 2000, pp. 367–376.

Velho, G., et al., "In Vitro and In Vivo Stability of Electrode Potentials in Needle–Type Glucose Sensors", *Diabetes, vol. 38, No. 2,* 1989, pp. 164–171.

Von Woedtke, T., et al., "In Situ Calibration of Implanted Electrochemical Glucose Sensors", *Biomedica Biochimica Acta, vol. 48,* 1989, pp. 943–952.

Vreeke, M. S., et al., "Hydrogen Peroxide Electrodes Based on Electrical Connection of Redox Centers of Various Peroxidases to Electrodes through a Three–Dimensional Electron–Relaying Polymer Network", *Diagnostic Biosensors Polymers, Chapter 15,* 1993, pp. 180–193.

Vreeke, M., et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network", *Analytical Chemistry, vol. 64, No. 24,* 1992, pp. 3084–3090.

Wade Jr., L. G., "Chapter 17: Reactions of Aromatic Compounds", *Organic Chemistry, Sixth Edition,* 2006, pp. 762–763.

Wagner, J. G., et al., "Continuous Amperometric Monitoring of Glucose in a Brittle Diabetic Chimpanzee with a Miniature Subcutaneous Electrode", *Proceedings of the National Academy of Sciences USA,* 1998, pp. 6379–6382.

Wang, D. L., et al., "Miniaturized Flexible Amperometric Lactate Probe", *Analytical Chemistry, vol. 65, No. 8,* 1993, pp. 1069–1073.

Wang, J., et al., "Activation of Glassy Carbon Electrodes by Alternating Current Electrochemical Treatment", *Analytica Chimica Acta, vol. 167,* 1985, pp. 325–334.

Wang, J., et al., "Amperometric Biosensing of Organic Peroxides with Peroxidase–Modified Electrodes", *Analytica Chimica Acta, vol. 254,* 1991, pp. 81–88.

Wang, J., et al., "Highly Selective Membrane–Free, Mediator–Free Glucose Biosensor", *Analytical Chemistry, vol. 66, No. 21,* 1994, pp. 3600–3606.

Wang, J., et al., "Screen–Printable Sol–Gel Enzyme–Containing Carbon Inks", *Analytical Chemistry, vol. 68, No. 15,* 1996, pp. 2705–2708.

Wang, J., et al., "Sol–Gel–Derived Metal–Dispersed Carbon Composite Amperometric Biosensors", *Electroanalysis, vol. 9, No. 1,* 1997, pp. 52–55.

Wang, X., et al., "Improved Ruggedness for Membrane–Based Amperometric Sensors Using a Pulsed Amperometric Method", *Analytical Chemistry, vol. 69, No. 21,* 1997, pp. 4482–4489.

Ward, W. K., et al., "A New Amperometric Glucose Microsensor: In Vitro and Short–Term In Vivo Evaluation", *Biosensors & Bioelectronics, vol. 17,* 2002, pp. 181–189.

Ward, W. K., et al., "Assessment of Chronically Implanted Subcutaneous Glucose Sensors in Dogs: The Effect of Surrounding Fluid Masses", *American Society for Artificial Internal Organs Journal,* 1999, pp. 555–561.

Ward, W. K., et al., "Rise in Background Current Over Time in a Subcutaneous Glucose Sensor in the Rabbit: Relevance to Calibration and Accuracy", *Biosensors & Bioelectronics, vol. 15,* 2000, pp. 53–61.

Ward, W. K., et al., "Understanding Spontaneous Output Fluctuations of an Amperometric Glucose Sensor: Effect of Inhalation Anesthesia and Use of a Nonenzyme Containing Electrode", *American Society for Artificial Internal Organs Journal,* 2000, pp. 540–546.

Wientjes, K. J. C., *Development of a Glucose Sensor for Diabetic Patients,* 2000, pp. vii–xiii.

Wilkins, E., et al., "Glucose Monitoring: State of the Art and Future Possibilities", *Medical Engineering and Physics, vol. 18, No. 4,* 1995, pp. 273–288.

Wilkins, E., et al., "Integrated Implantable Device for Long–Term Glucose Monitoring", *Biosensors & Bioelectronics, vol. 10,* 1995, pp. 485–494.

Williams, D. L., et al., "Electrochemical–Enzymatic Analysis of Blood Glucose and Lactate", *Analytical Chemistry, vol. 42, No. 1,* 1970, pp. 118–121.

Wilson, G. S., et al., "Enzyme–Based Biosensors for In Vivo Measurements", *Chemical Reviews, vol. 100, No. 7,* 2000, pp. 2693–2704.

Wilson, G. S., et al., "Progress Toward the Development of an Implantable Sensor for Glucose", *Clinical Chemistry, vol. 38, No. 9,* 1992, pp. 1613–1617.

Wood, W. D., et al., "Hermetic Sealing with Epoxy", *Mechanical Engineering,* 1990, pp. 46–48.

Wu, H., et al., "In Situ Electrochemical Oxygen Generation with an Immunoisolation Device", *Annals of the new York Academy of Sciences, vol. 875,* 1999, pp. 105–125.

Yabuki, S., et al., "Electro–Conductive Enzyme Membrane", *Journal of the Chemical Society, Chemical Communications,* 1989, pp. 945–946.

Yang, L., et al., "Determination of Oxidase Enzyme Substrate Using Cross–Flow Thin–Layer Amperometry", *Electroanalysis, vol. 8, No. 8–9,* 1996, pp. 716–721.

Yang, Q., et al., "Development of Needle–Type Glucose Sensor with High Selectivity", *Sensors and Actuators B, vol. 46,* 1998, pp. 249–256.

Yao, S. J., et al., "The Interference of Ascorbate and Urea in Low–Potential Electrochemical Glucose Sensing", *Proceedings of the Twelfth Annual International Conference of the IEEE Engineering in Medicine and Biology Society, vol. 12, Part 2,* 1990, pp. 487–489.

Yao, T., "A Chemically–Modified Enzyme Membrane Electrode as an Amperometric Glucose Sensor", *Analytica Chimica Acta, vol. 148,* 1983, pp. 27–33.

Ye, L., et al., "High Current Density 'Wired' Quinoprotein Glucose Dehydrogenase Electrode", *Analytical Chemistry, vol. 65, No. 3,* 1993, pp. 238–241.

Yildiz, A., et al., "Evaluation of an Improved Thin–Layer Electrode", *Analytical Chemistry, vol. 40, No. 7,* 1968, pp. 1018–1024.

Zamzow, K., et al., "New Wearable Continuous Blood Glucose Monitor (BGM) and Artificial Pancreas (AP)", *Diabetes, vol. 39,* 1990, pp. 5A–20.

Zavalkoff, S. R., et al., "Evaluation of Conventional Blood Glucose Monitoring as an Indicator of Integrated Glucose Values Using a Continuous Subcutaneous Sensor", *Diabetes Care, vol. 25, No. 9,* 2002, pp. 1603–1606.

Zhang, Y., et al., "Application of Cell Culture Toxicity Tests to the Development of Implantable Biosensors", *Biosensors & Bioelectronics, vol. 6,* 1991, pp. 653–661.

Zhang, Y., et al., "Elimination of the Acetaminophen Interference in an Implantable Glucose Sensor", *Analytical Chemistry, vol. 66, No. 7,* 1994, pp. 1183–1188.

Zhu, J., et al., "Planar Amperometric Glucose Sensor Based on Glucose Oxidase Immobilized by Chitosan Film on Prussian Blue Layer", *Sensors, vol. 2,* 2002, pp. 127–136.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–12, 14 and 16–29 is confirmed.

Claims 13, 15, 30, 31, 34 and 42 are determined to be patentable as amended.

Claims 32, 33, 35–41 and 43–48, dependent on an amended claim, are determined to be patentable.

New claims 49–57 are added and determined to be patentable.

13. The analyte sensor of claim 2, wherein the working electrode [in] *is* adapted to provide a signal of current density of at least about 69 μA/cm² at 37° C. at a glucose concentration of 10 mM.

15. The [analytic] *analyte* sensor of claim 2, wherein the sensor is adapted to provide a current signal deviating not more than about 5% form its average value for at least 72 hours after equilibration when glucose concentration is maintained at 10 mM.

30. A method of measuring the concentration of glucose in an animal tissue, the method comprising the steps of:
  (a) subcutaneously implanting into the animal a flexible sensor configured to generate a signal indicative of the glucose concentration, the sensor comprising:
    a non-corroding working electrode adapted for subcutaneous implantation in an animal;
    a sensing layer comprising a non-leachable glucose-responsive enzyme disposed on the working electrode; and
    a glucose diffusion-limiting layer disposed on the sensing layer;
    *wherein the sensor is adapted to provide an electrical signal that is substantially insensitive to relative motion between the implanted portion of the sensor and tissue surrounding the implanted portion of the sensor;*
  (b) allowing the glucose to reach the working electrode; and
  (c) limiting the rate of glucose transport to the sensing layer to a level substantially lower that the rate of glucose transport to the tissue surrounding the sensor.

31. A method for inserting a flexible glucose sensor, comprising:
  (a) providing an introducer having a width of not more than [about] 22 gauge adapted to subcutaneous placement of a portion of a flexible, glucose sensor in an animal;
  (b) placing within the introducer a portion of a flexible, glucose sensor, the portion of a flexible, glucose sensor comprising:
    a non-corroding working electrode adapted for subcutaneous implantation in an animal; and
    a sensing layer comprising a non-leachable, glucose-responsive enzyme disposed on the working electrode;
  (c) inserting the introducer into the animal so that the portion of the flexible, glucose sensor is carried into the subcutaneous tissue;
  (d) withdrawing the introducer from the animal while leaving the portion of a flexible glucose sensor implanted within the subcutaneous tissue of the animal; and
  (e) connecting a signal measuring device to a portion of the sensor exterior to the animal.

34. A flexible glucose sensor comprising:
  a portion of the sensor that is adapted for positioning external to the animal and for electrical contact with a device for measurement of the electrical signal generated by the sensor;
  a portion of the sensor that is adapted for subcutaneous implantation in an animal; comprising:
    at least one non-corroding, glucose-responsive working electrode; and
    a sensing layer coupled to the working electrode;
  wherein the sensor is flexible *and is adapted to provide an electrical signal that is substantially insensitive to relative motion between the implanted portion of the sensor and tissue surrounding the implanted portion of the sensor* and the width of the portion of the sensor that is adapted for subcutaneous implantation is less than about 0.29 mm.

42. The flexible glucose sensor of claim [39] *41*, wherein the biocompatible layer comprises poly (ethylene oxide).

*49. The glucose measurement system of claim 18, further comprising an introducer adapted for subcutaneous placement of a portion of a flexible glucose sensor in an animal:*
  *wherein a portion of the sensor is carried within the sensor introducer; and*
  *wherein the introducer can be withdrawn from the animal while leaving the portion of a flexible glucose sensor implanted with the subcutaneous tissue of the animal.*

*50. The glucose measurement system of claim 49, wherein the introducer has a width of not more than about 22 gauge.*

*51. An introduction system of claim 25, wherein the introducer has a width of not more than about 22 gauge.*

*52. The method of claim 29, further comprising providing an introducer adapted for subcutaneous placement of a portion of a flexible glucose sensor in an animal: and wherein a portion of the sensor is carried within the sensor introducer; and wherein the introducer can be withdrawn from the animal while leaving the portion of a flexible glucose sensor implanted with the subcutaneous tissue of the animal.*

*53. The method of claim 52, wherein the introducer has a width of not more than about 22 gauge.*

*54. The method of claim 30, further comprising providing an introducer adapted for subcutaneous placement of a portion of a flexible glucose sensor in an animal; and wherein a portion of the sensor is carried within the sensor introducer; and wherein the introducer can be withdrawn from the animal while leaving the portion of a flexible glucose sensor implanted with the subcutaneous tissue of the animal.*

*55. The method of claim 54, wherein the introducer has a width of not more than about 22 gauge.*

*56. The glucose measurement system of claim 18, wherein the sensor is flexible and is adapted to provide an electrical signal that is substantially insensitive to relative motion* between the implanted portion of the sensor and tissue surrounding the implanted portion of the sensor.

57. The method of claim 29, wherein implanting into the animal a flexible sensor further comprises the sensor being adapted to provide an electrical signal that is substantially insensitive to relative motion between the implanted portion of the sensor and tissue surrounding the implanted portion of the sensor.

\* \* \* \* \*

(12) EX PARTE REEXAMINATION CERTIFICATE (10610th)
United States Patent
Heller et al.

(10) Number: US 6,329,161 C2
(45) Certificate Issued: May 28, 2015

(54) SUBCUTANEOUS GLUCOSE ELECTRODE

(76) Inventors: Adam Heller, Austin, TX (US); Michael V. Pishko, Austin, TX (US)

Reexamination Request:
No. 90/009,620, Oct. 27, 2009

Reexamination Certificate for:
Patent No.: 6,329,161
Issued: Dec. 11, 2001
Appl. No.: 09/668,221
Filed: Sep. 22, 2000

Reexamination Certificate C1 6,329,161 issued Sep. 29, 2009

Related U.S. Application Data

(63) Continuation of application No. 09/477,053, filed on Jan. 3, 2000, now Pat. No. 6,162,611, which is a continuation of application No. 09/356,102, filed on Jul. 16, 1999, now Pat. No. 6,121,009, which is a continuation of application No. 08/767,110, filed on Dec. 4, 1996, now Pat. No. 6,284,478, which is a continuation of application No. 08/299,526, filed on Sep. 1, 1994, now Pat. No. 5,593,852, and a continuation-in-part of application No. 08/161,682, filed on Dec. 2, 1993, now Pat. No. 5,356,786.

(51) Int. Cl.
*C12Q 1/00* (2006.01)
*C12Q 1/54* (2006.01)

(52) U.S. Cl.
CPC ...... *C12Q 1/006* (2013.01); *C12Q 1/54* (2013.01); *Y10S 435/917* (2013.01); *Y10S 435/962* (2013.01); *Y10S 435/817* (2013.01)

(58) Field of Classification Search
USPC .................................................. 435/14
See application file for complete search history.

(56) References Cited

To view the complete listing of prior art documents cited during the proceeding for Reexamination Control Number 90/009,620, please refer to the USPTO's public Patent Application Information Retrieval (PAIR) system under the Display References tab.

*Primary Examiner* — Gary Kunz

(57) ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 5, 27 and 37 is confirmed.

Claims 1-4, 6-26, 28-36 and 38-57 are cancelled.

\* \* \* \* \*